(12) United States Patent
Danielov

(10) Patent No.: US 6,303,588 B1
(45) Date of Patent: Oct. 16, 2001

(54) THERAPEUTIC METHODS UTILIZING NATURALLY DERIVED BIO-ACTIVE COMPLEXES AND DELIVERY SYSTEMS THEREFOR

(75) Inventor: Michael M. Danielov, 98-25 65th Rd., Apt. 2E, Rego Park, NY (US) 11374

(73) Assignee: Michael M. Danielov, Rego Park, NY (US)

(*) Notice: Subject to any disclaimer, the term of this patent is extended or adjusted under 35 U.S.C. 154(b) by 0 days.

(21) Appl. No.: 09/228,384

(22) Filed: Jan. 12, 1999

Related U.S. Application Data

(62) Division of application No. 08/350,234, filed on Dec. 6, 1994, now Pat. No. 5,885,974.

(51) Int. Cl.[7] .............. A61K 31/66; A61K 31/045; A61K 31/59; A61K 31/557

(52) U.S. Cl. ............. 514/109; 514/103; 514/305; 514/224; 514/167; 514/171; 514/573; 514/182

(58) Field of Search .................. 514/109, 305, 514/103, 724, 167, 171, 573, 182

Primary Examiner—Theodore J. Criares
(74) Attorney, Agent, or Firm—Helfgott & Karas, P. C.

(57) ABSTRACT

Methods are disclosed for correcting biological information transfer in a patient in need of such therapy which comprise administration to a patient of a composition comprising a therapeutically effective amount of a biocomplex comprising at least one bioactive agent from each of the three informational blocks of biological information transfer, each agent being present in an amount sufficient to correct the biological information transfer of the patient under treatment and resulting in the resumption of normal cell metabolism, said amount being less than the buffering amount of said agent; together with a carrier therefor.

9 Claims, 30 Drawing Sheets

THERAPEUTIC METHODS UTILIZING NATURALLY DERIVED BIO-ACTIVE COMPLEXES AND DELIVERY SYSTEMS THEREFOR

This is a division of application Ser. No. 08/350,234, filed Dec. 6, 1994, now U.S. Pat. No. 5,885,974.

BACKGROUND OF THE INVENTION

Normalcy and stability in the functional activity of living organisms and adaptation by the organism to newly developing situations is possible only with the stability of internal informational links within the organism, i.e., only with the informational stability of a living organism. The transfer of biological information and realization of its effects in living organisms has a complex multi-step character and includes vertical and horizontal links with a multitude of feedbacks at various stages.

Structurally, this complex multi-step biological information transfer can be subdivided into three basic levels: the generation and transfer of information; the recognition and decoding of initial information; and intracellular transformation of decoded information into a new external/outgoing signal. This information transfer is shown schematically in FIG. 1.

The generation of initial internal information takes place both within specialized organs synthesizing and secreting these or other biologically active substances and at the final stage of activity of the majority of cells in the living organism. The difference can consist only in the strength, character, concentration, and informational value of the information being generated. The information being generated represents only the first degree messengers. In other words, the carriers of the initial internal information are the various information substances modulating the final effects that are necessary at the output of the entire information chain.

The majority of biologically active substances, hormones etc. that have specific receptors in cells and target organs belong to this group of first degree messengers. Very often the place of synthesis and secretion of first degree messengers is at a considerable distance from the place of their final realization (cells and target organs). The most frequent (although not the only) way of transporting these substances to the cells and target organs is via the blood circulatory system. Another type of first degree messenger is the typical medicament, which due to its stereochemical structure, functions by acting upon various specific receptors in the cells and/or in target organs.

At the second level of biological information transfer is the recognition and decoding of initial information. This important element of information regulation involves the recognition of the first degree information substances and is carried out by strictly specific cell receptors. These receptors are typically located on the cell membrane (membrane receptors) or within the cells (cytosol or nuclear receptors), and included in their structure a polymeric molecule as a carrier of biological specificity. Any biomolecule specifically joining chemical compounds (ligand, agonist, antagonist, medication etc.) on the surface or within the cell and transforming received information into the cell's biological response can serve as a receptor. After the initial information is recognized by cellular receptors, it is processed by being decoded. Decoding of the incoming signal is possible due to conformational changes of the receptor structure and the activation of cell membrane and or intracellular decoding systems. Both decoding factors are strictly specific and are activated only after the complex of first degree messengers and cell receptors has been formed.

The effective realization of the process of this second level, as well as the regulation and stability thereof, depends to a great extent on the functional state and activity of transmembrane and intracellular conjunction agents, such as lipids, phospholipids, and other cell membrane structural components, etc.

At the third level, decoded information is transformed intracellularly into a new external/outgoing signal. This transformation of a molecular signal into a biochemical reaction consists in the synthesis of new information substances. It is important to point out that the intracellular information transfer has a more unified nature than the transfer of information at the previous two levels. More precisely, for each informational substance of the first degree and its corresponding receptor there is no specific agent responsible for the further transfer of intracellular information.

Thus, there are only a few universal ways of intracellular information transfer, which fall into one of the two following groups: extended notion of intracellular second degree messengers—signal transformation and transfer by means of cyclic nucleotides, inositol triphosphate-diacylglycerol line, Ca++—calmodulin way, etc; or multifactor activators—translocation and intramolecular tie up of receptors with cell acceptors, temperature activation of first degree messenger-receptor complexes, ionic forces, intracellular cascade system, etc.

One can readily observe reduced diversity (but not intensity) of biological information transfer on the third level, which ensures the universal stability of the signal transfer and transformation structure on the intracellular level. All of this is expressed in the closed-system character of the intracellular information volume throughout the second degree messengers and their analogs.

Effective transformation of the decoded signal into the cell's biological response depends to a great extent on the functional activity of non-specific cell transmitters and trigger systems, particularly such as intracellular prostaglandins of various groups, i.e., $PGE_{1\&2}$, $PGF_{1\&2}$, PGA, PGB, prostacyclins, thromboxans, etc. Thus, normal functioning of intracellular information volume is ensured by the buffer concentration of intracellular prostaglandins. Intracellular information transformation and transfer leads to the activation of specific chromatin acceptor locations which initiate multiple specific effects, with transcription processes being initially modulated. The final effect of this complex chain of information transfer is stimulation/suppression of DNA synthesis, i.e., the final cellular response—information transformation from first degree messengers to a new cell output signal, which consists in the synthesis (generation) of new information substances. These newly-formed information substances, in their turn, influence the type and intensity of the signal which caused their stimulation/suppression by means of a feedback mechanism.

If structurally the transfer of biological information and the realization of its effects in living organisms is expressed in terms of three levels, it physically materializes itself in the form of informational blocks as shown in FIG. 2. It is important to point out that the transfer of biological information by blocks actually corresponds to the levels of information transfer.

The first informational block involves the formation of initial information, and includes two stages: synthesis and secretion of first degree messengers of natural origin, or introduction of artificial or non-naturally occurring substances; and the transporting of information substances to cells and target organs.

The second informational block involves the identification of information and includes two stages; strictly specific cell reception of the first degree messengers; and the decoding of a signal carried by the first degree messengers.

The third informational block involves the transformation of a molecular signal into a biochemical reaction and includes a set of intracellular transformers of decoded initial information and their transmitters into the cell final outgoing signal, which results in the synthesis of new information substances.

The informational stability of a living organism is thus affected by four factors: the intensity of influence (in terms of amount and concentration) of an entire group of antagonistically acting first degree informational substances (the first informational block); the presence (in terms of amount and activity) in cells and target organs of specific receptors for certain first degree information substances that initiate intracellular processes resulting in the synthesis of genetically determined new information substances (the second informational block); the functional state (in terms of amount and activity) of intracellular regulating mechanisms transforming the molecular signal into a biochemical reaction (the third informational block); and the genetic determination of the cell function.

When any of these factors are disturbed, a pathology results. Various pathologies have their basis in various stages of the biological information transfer. Thus, a common basis for therapy exists for all pathologies wherein this information transfer has been adversely affected.

Present methods of correction and/or treatment of the different pathologies (as well as skin dysfunctions) are aimed towards attempting to reconstruct the transfer of biological information both by means of interacting directly with the first degree messengers (peptides, steroids, lipids, etc.) and indirectly through the change in the activity and/or amount of the first degree information substances.

It is necessary to emphasize that such methods utilize the first degree informational substances in amounts greatly exceeding the endogenic production of these substances. For instance, prednisone, a commonly prescribed glucocorticosteroid hormone that is about 6–8 times more active that its endogenous analog hydrocortisone, is typically administered by injection in a dosage of 30 mg or orally, in a daily dosage of 12–16 mg. This is approximately equivalent to 40–60 days of the total production of the adrenal cortex gland (corticosuprarenal gland) of hydrocortisone. Taking into account the activity differential, one typical daily therapeutic dose of prednisone is similar to the amount produced by a normally functioning gland over a period of about ten months.

Additionally, the physiological and biochemical response from "therapeutic" and physiological" dosages of bioactive substances are very different. Frequently, unusual and non-physiological effects are observed when the same bioactive substance is used in amounts exceeding the physiological level.

These current therapeutic practices are not without consequences since the administration of such amounts exceed the organism's normal endogenous production, and as a result causes the loss of the control of the organism's buffering mechanism. This results in a failure of restoration of the disrupted metabolism (disrupted transfer of biological information). The new non-physiological regulation quickly gets out of order, thereby creating more and more disruptions in the normal biological information transfer and making the organism's informational transfer unstable.

By referring to FIGS. 1 and 2, which diagram normal biological information transfer, it can be seen to what degree present therapeutic methods of treatment are inadequate and inefficient to ensure the information stability of the organism.

A most important aspect of any therapeutic method is the delivery of the active to the target receptor or cell of the organism. The delivery system utilized must provide stability for the active therein, while still allowing the absorption/delivery thereof. To effect useful therapy it is necessary that both requirements be met by the drug delivery system. Especially in the areas of topical and parenteral administration, it is critical to efficacy to provide a delivery system which crosses the cell membrane and allows the active agent or agents to exert their effects.

Stratum corneum, the outer layer of skin, is a multi-cellular membrane of flattened, metabolically active cells. In living organisms, the membrane is dynamic, and the transfer or non-transfer of various agents across this membrane is an important basis of both drug and cosmetic therapy. In order to provide useful therapeutic and cosmetic formulations, it is necessary to utilize a delivery system which is both compatible with the skin, i.e., non-irritating, and which will allow and even facilitate the transfer of the active agent, whether cosmetic or therapeutic, across the skin membrane. It is additionally necessary to utilize a delivery system in which the bioactive components are physically and chemically stable, yet still available for absorption.

SUMMARY OF THE INVENTION

The present invention relates to therapeutic methods based on the correction of biological information transfer in organisms where various metabolic disruptions in the organism have occurred. By enabling the reconstruction of the transfer of biological information by restoration of genetically determined chain of biological information transfer by way of simultaneously acting on all levels of the multilevel information transfer, normal cell metabolism is restored.

In accordance with the present invention, restoration the natural biological information transfer is possible by means of creating natural biologically active complexes containing all the necessary information ensuring normal biological information transfer on all three levels. Thus, the informational stability of the organism is ensured by supporting all the basic elements responsible for biological information transfer.

This restoration of biological information transfer is possible by administration of the following types of natural biologically active complexes: vitamin and coenzyme biocomplexes (VCBs); natural bioactive complexes (NBCs); bioactive complexes modeling (BCMs); and multicomponent biologically active complexes (MBACs).

The quantity, concentration/activity of the agents utilized in the bioactive complexes of the present invention depends upon the particular pathology under treatment, and particularly upon the particular information chain in need of support or restoration to a state of normal biological information transfer.

The efficiency and safety of the bioactive complexes of the instant invention is ensured by selection of a concentration/activity of the information agents in the biocomplexes that are completely governed by the live organism buffering principle. This principle or mechanism functions by the principle of reserving information capacity and ensures that the extra quantity of informational substances in the organism will be eliminated by the buffering ability of the organism.

The present invention also provides therapeutic methods for the restoration of normal cell metabolism in patients in need of such treatment are provided which utilize multi-component biologically active complexes. These multi-component biologically active complexes can be utilized in the treatment of a wide variety of pathologies which have their origin in the disruption of normal biological information transfer thus resulting in a consequent alteration in cell metabolism. Specific complexes, which can be utilized to topically treat various conditions of both normal and diseased skin such as chapping (dry skin), oily skin, cellulite, atopic dermatitis, ichthyosis, psoriasis, acne, comedones, seborrhea, eczema, neurodermatitis, macular atrophies, skin aplasias, hyperkeratinizations, and alopecia, are provided. Also provided are parenterally administrable compositions suitable for administration to patients suffering from trauma or shock. These bioactive complexes are formulated in a natural delivery system which enhances the absorption of the bioactive complex into the cell, thereby providing a useful therapeutic tool for both cosmetic and medicinal applications.

The novel natural delivery system of the present invention (also referred to herein as a substitute cell membrane) is thus not only useful as a topical and parenteral vehicle for the aforementioned bioactive complexes, but may also be used as a vehicle for topical application of other skin treating agents, including such pharmaceutical compounds as steroids, anti-microbials, proteins, peptides, anti-inflammatory agents, sunscreens, etc., and as a vehicle for parenteral administration of similar therapeutic agents so administered.

OBJECTS OF THE INVENTION

It is thus an object of the invention to provide therapeutic methods based on the correction of biological information transfer in organisms where various metabolic disruptions in the organism have occurred using various types of bioactive complexes in a novel delivery system to restore normal cell metabolism.

It is further an object of the present invention to provides therapeutic methods based on the correction of various metabolic disruptions in the organism (during various pathologies) by means of creating specific bioactive complexes with or without the substitute cell membrane delivery system of the present invention.

It is further and object of the present invention to provide compositions useful in the treatment of various ailments of both normal and diseased skin and scalp, using bioactive complexes in a novel delivery system.

It is further an object of the invention to provide therapeutic and cosmetic methods of treating various conditions of normal skin and scalp, such as dry and oily conditions.

It is a still further object of the present invention to provide therapeutic and cosmetic methods of treating various conditions of diseased skin and scalp.

It is yet a further object of the present invention to provide novel delivery systems suitable as topical and parenteral carriers for the bioactive agents and complexes thereof.

It is a still further object of the present invention to provide compositions for parenteral administration, useful in the treatment of trauma or shock.

It is yet a still further object of the present invention to provide novel delivery systems for the delivery of therapeutic and cosmetic agents useful in the treatment of both normal and diseased skin and scalp.

DETAILED DESCRIPTION OF THE INVENTION

The present invention thus concerns a method of correcting biological information transfer in a patient in need of such therapy which comprises administration to said patient a composition comprising a therapeutically effective amount of a biocomplex comprising at least one bioactive agent from each of the three informational blocks of biological information transfer, each agent being present in an amount sufficient to correct the biological information transfer of the patient under treatment and resulting in the resumption of normal cell metabolism, said amount being less than the buffering amount of said agent; together with a carrier therefor.

Figure 1:
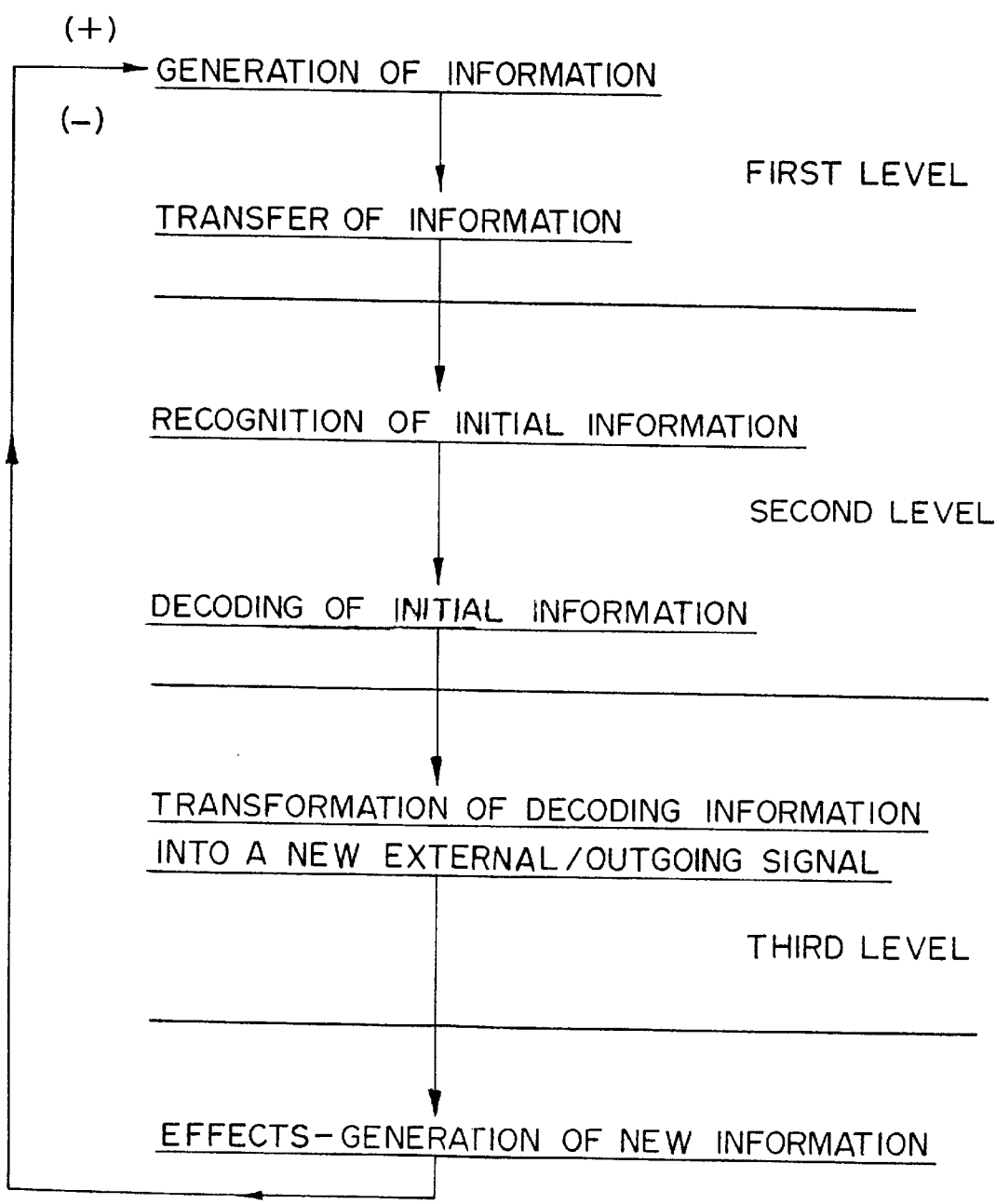
FIG. 1 is a diagram illustrating the general principle of information regulation in live organisms (informational levels).
Figure 2:
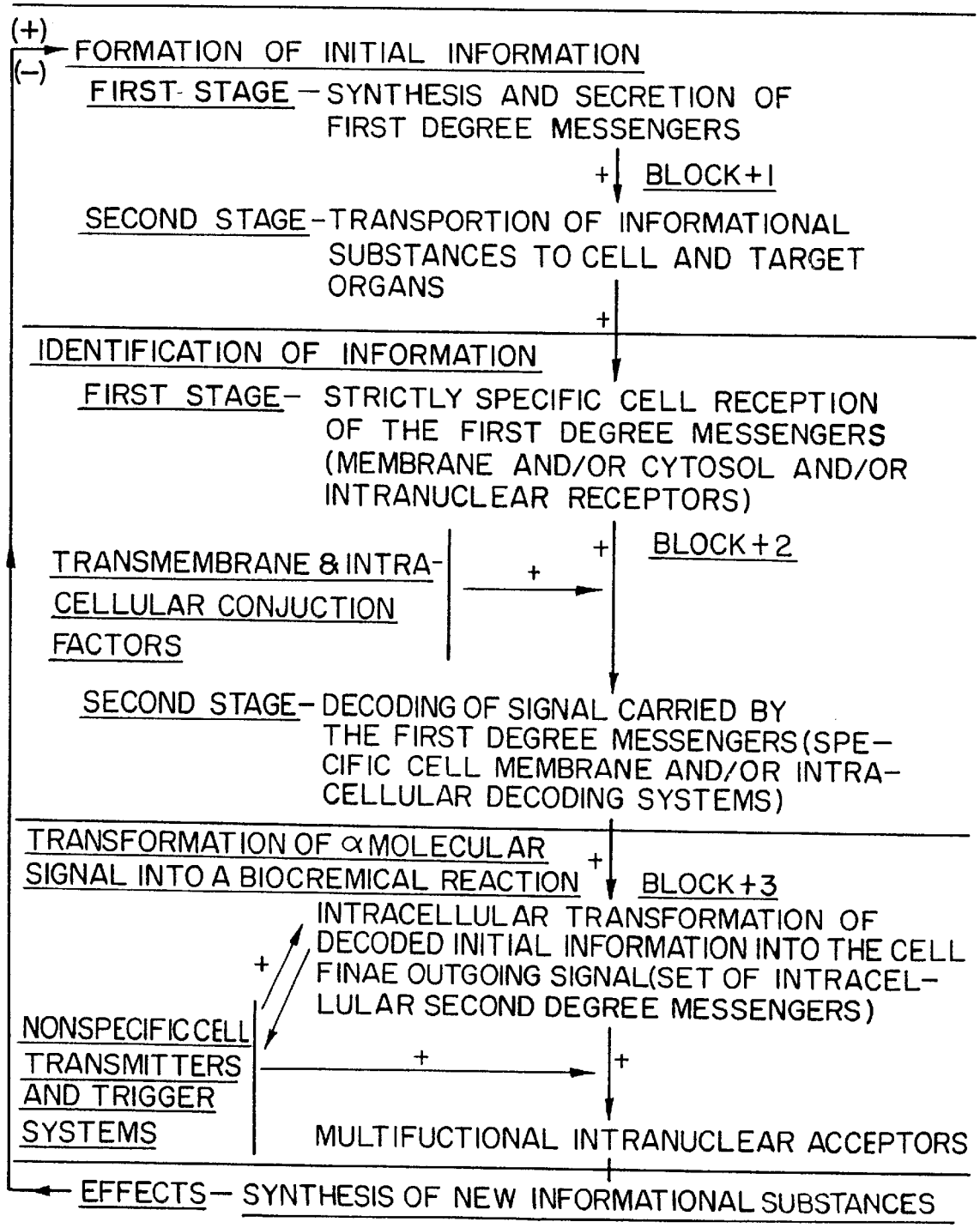
FIG. 2 is a diagram illustrating the structure of biological information transfer (informational blocks).
Figure 3:
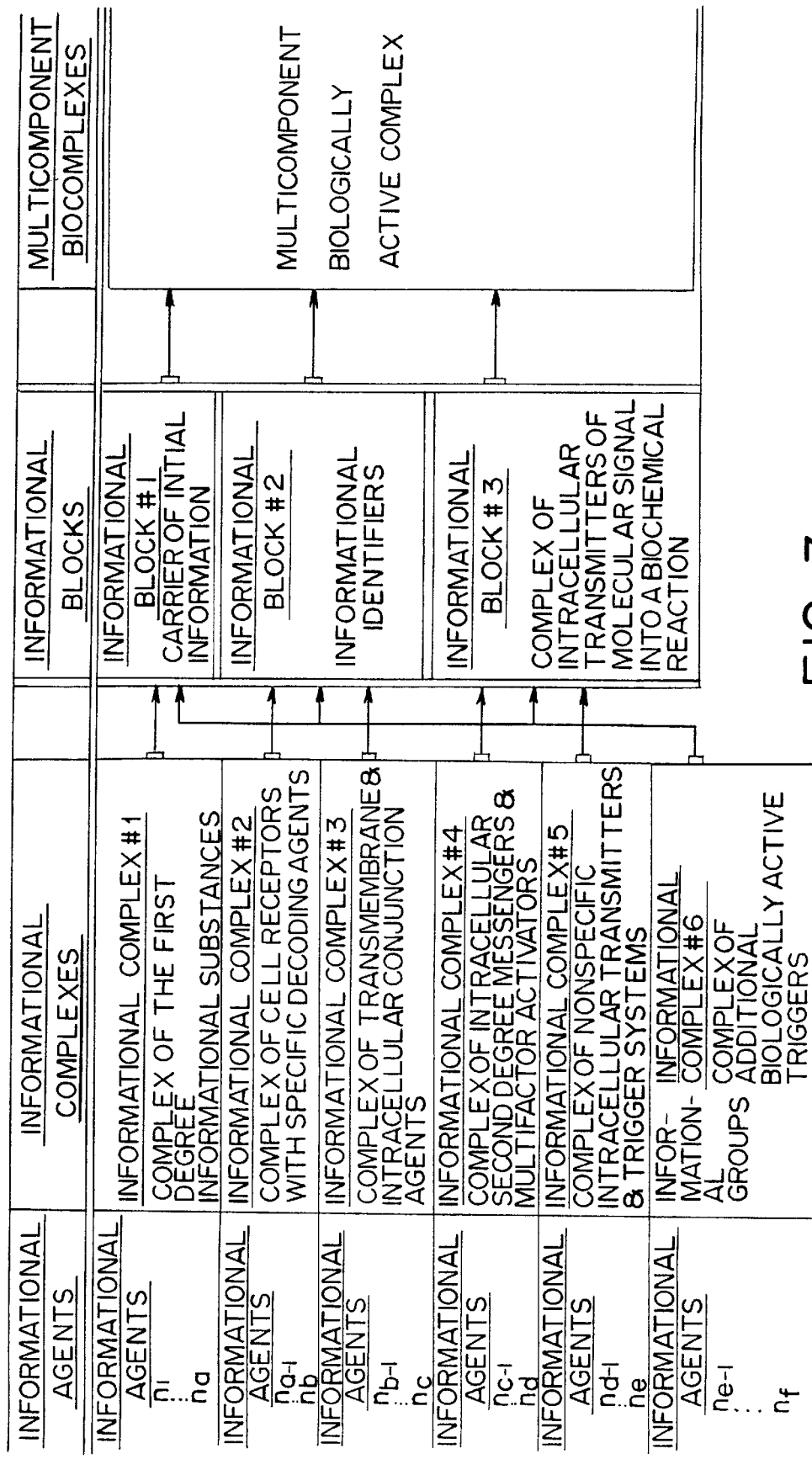
FIG. 3 is a diagram illustrating the structure of multi-component biologically active complexes.
Figure 4:
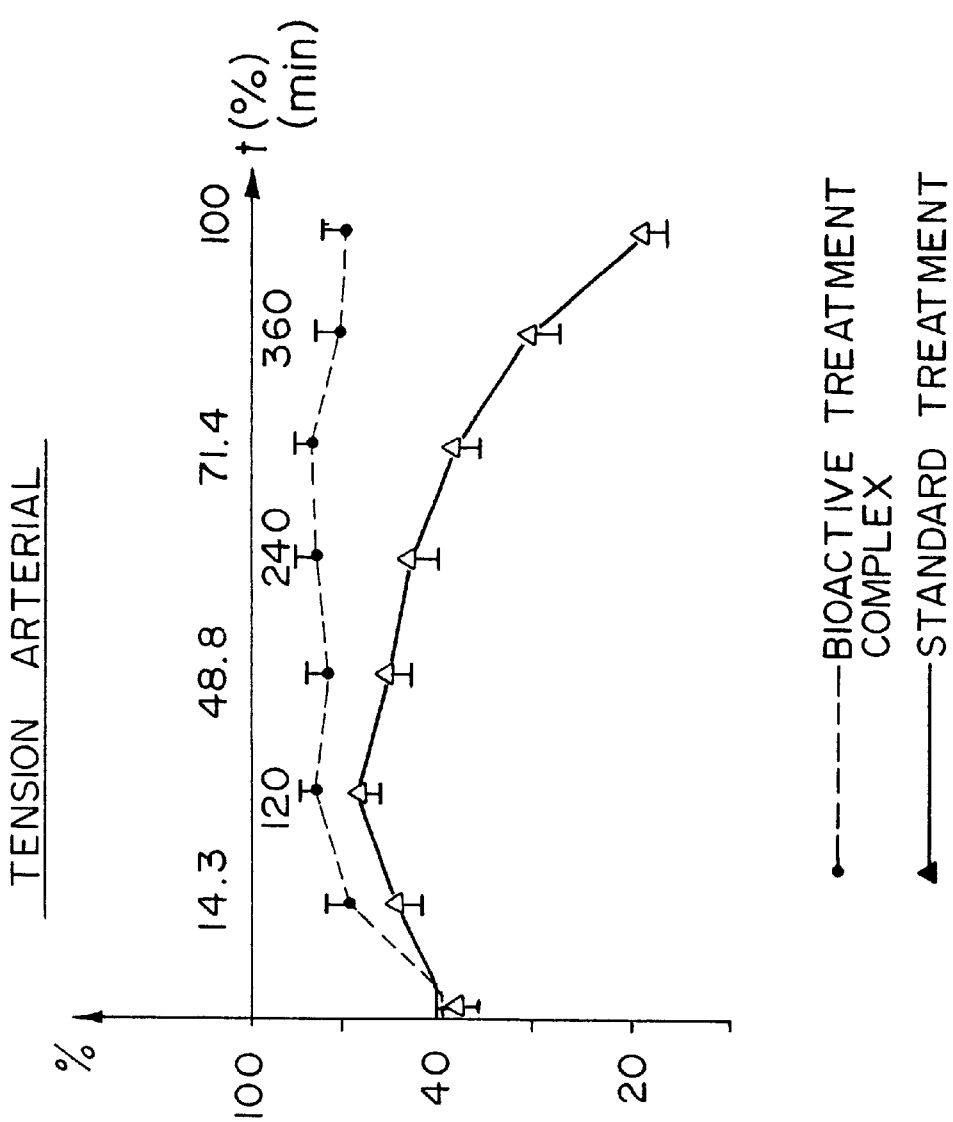
FIG. 4 is a graph showing the results of the effects of a composition of the instant invention versus the effect of standard treatment in anesthetized dogs post trauma on arterial tension.
Figure 5:
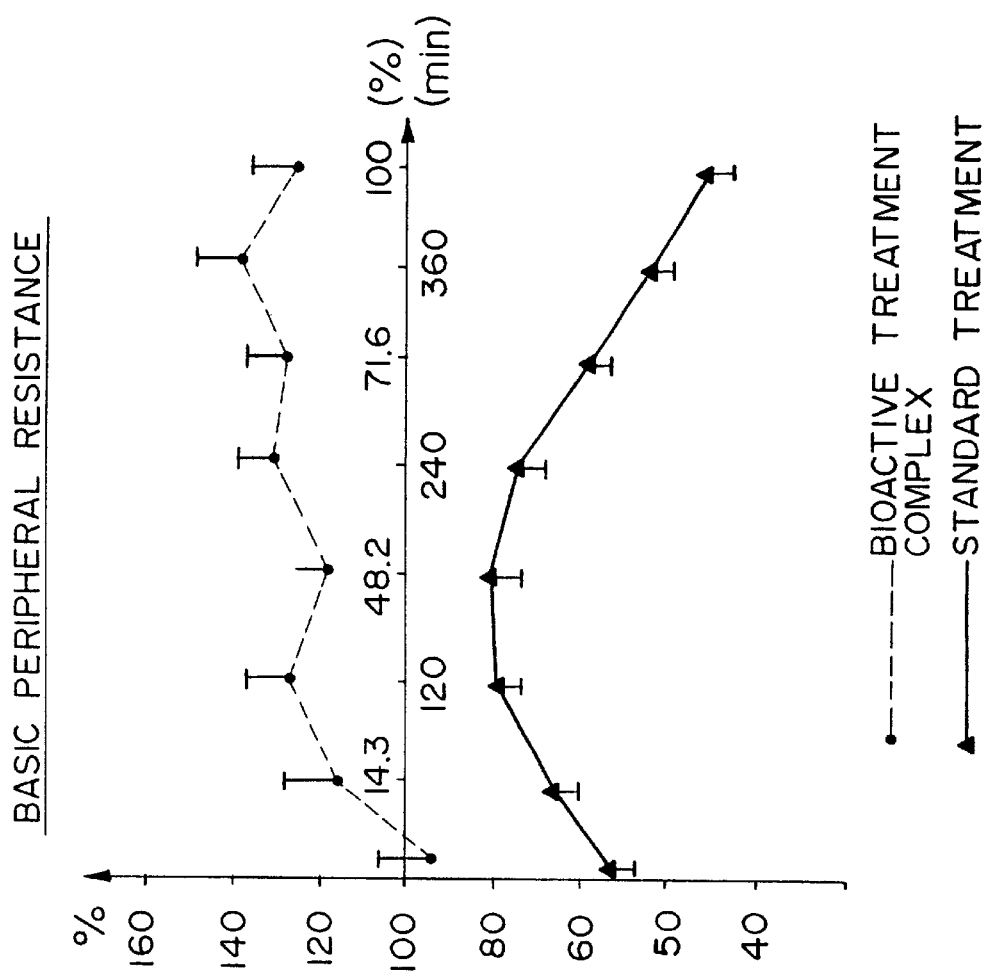
FIG. 5 is a graph showing the results of the effects of a composition of the instant invention versus the effect of standard treatment in anesthetized dogs post trauma on basic peripheral resistance.
Figure 6:
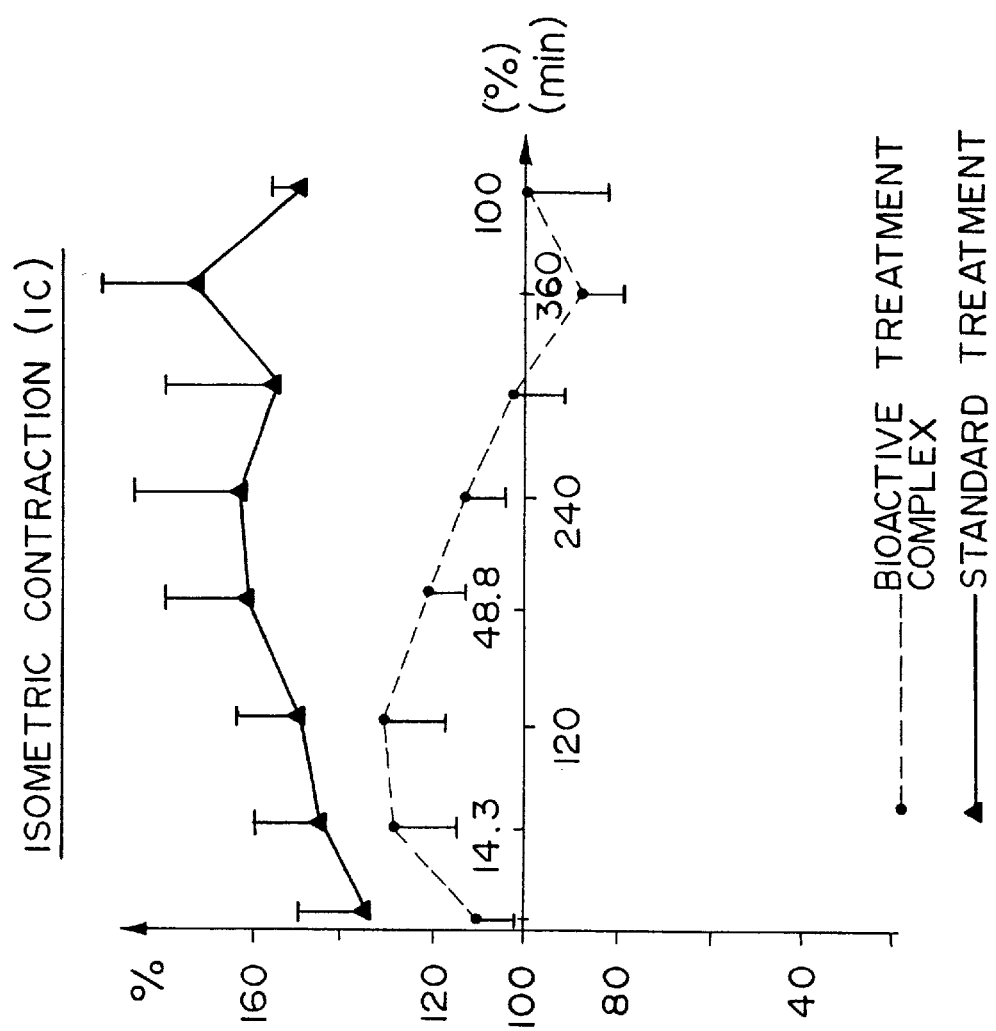
FIG. 6 is a graph showing the results of the effects of a composition of the instant invention versus the effect of standard treatment in anesthetized dogs post trauma on isometric contraction (IC).
Figure 7:
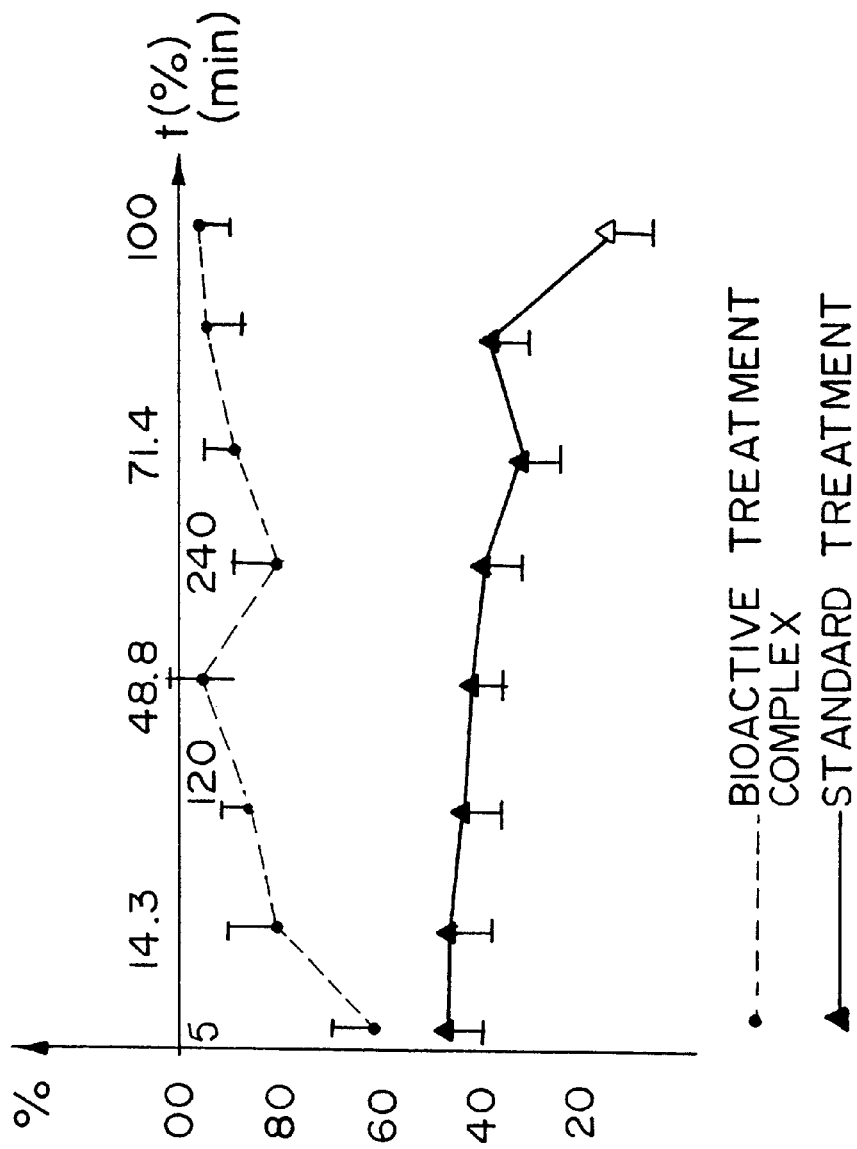
FIG. 7 is a graph showing the results of the effects of a composition of the instant invention versus the effect of standard treatment in anesthetized dogs post trauma on integral local microcirculation.
Figure 8:
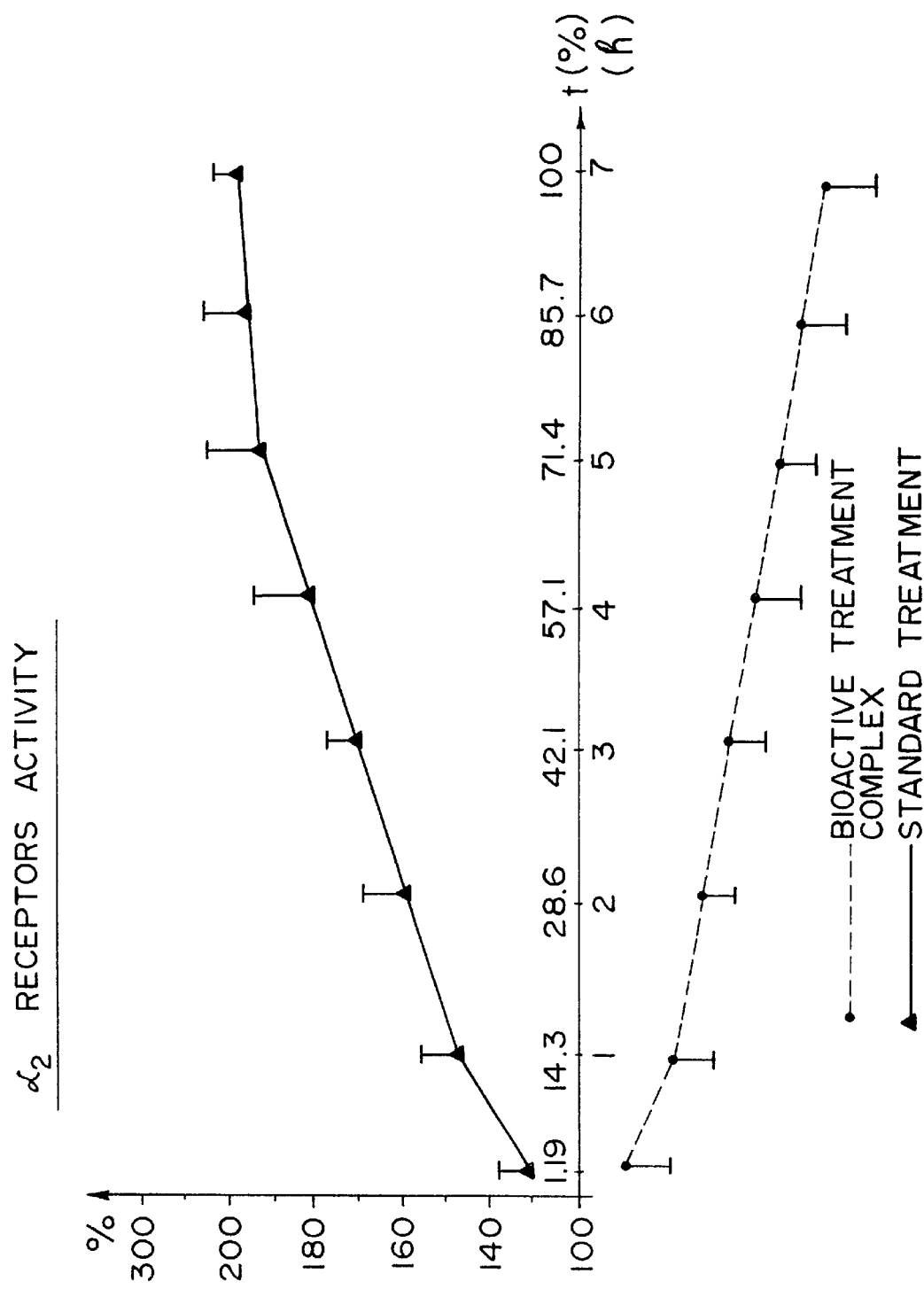
FIG. 8 is a graph showing the results of the effects of a composition of the instant invention versus the effect of standard treatment in anesthetized dogs post trauma on $\alpha_2$ receptors activity.
Figure 9:
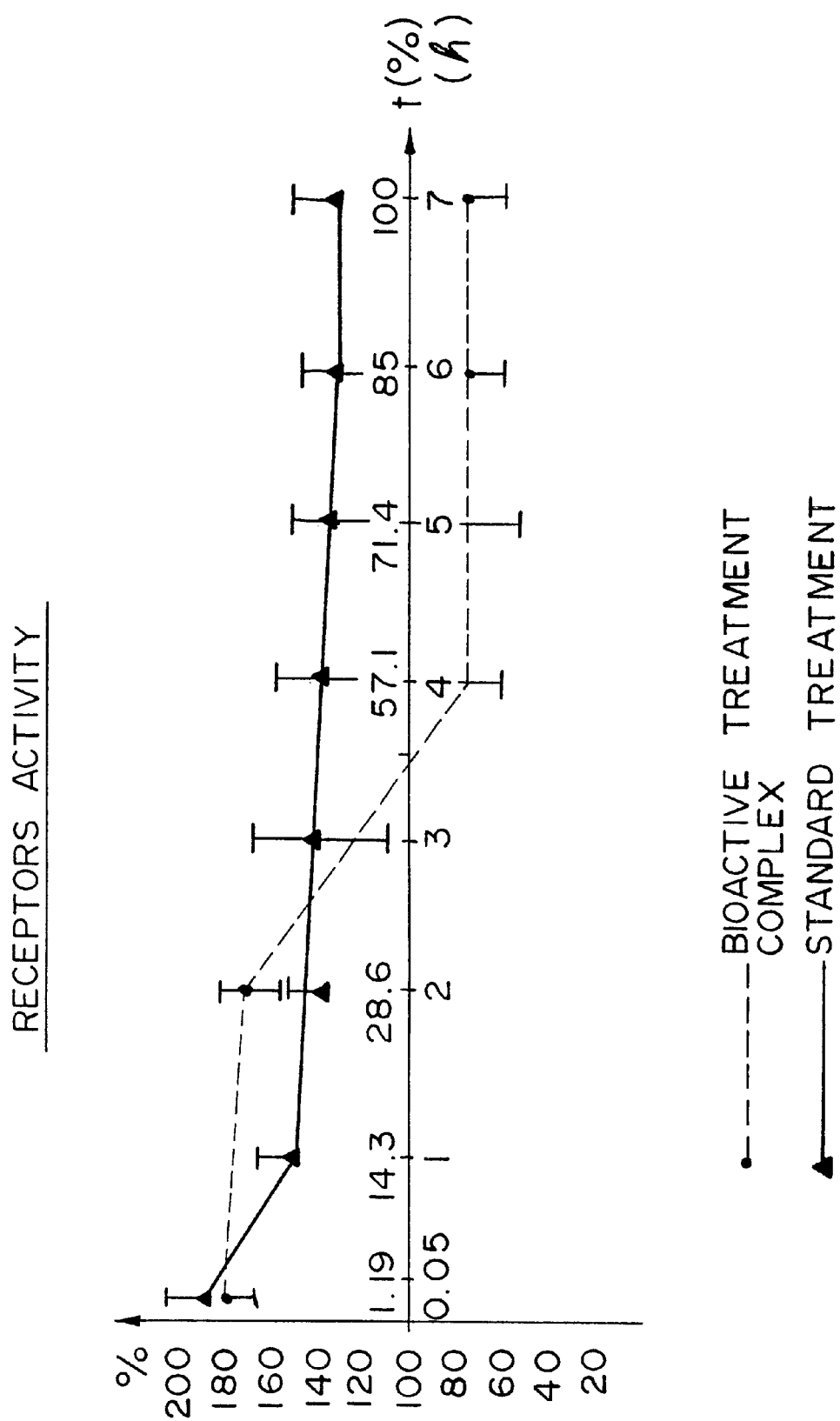
FIG. 9 is a graph showing the results of the effects of a composition of the instant invention versus the effect of standard treatment in anesthetized dogs post trauma on $\beta_2$ receptors activity.
Figure 10:
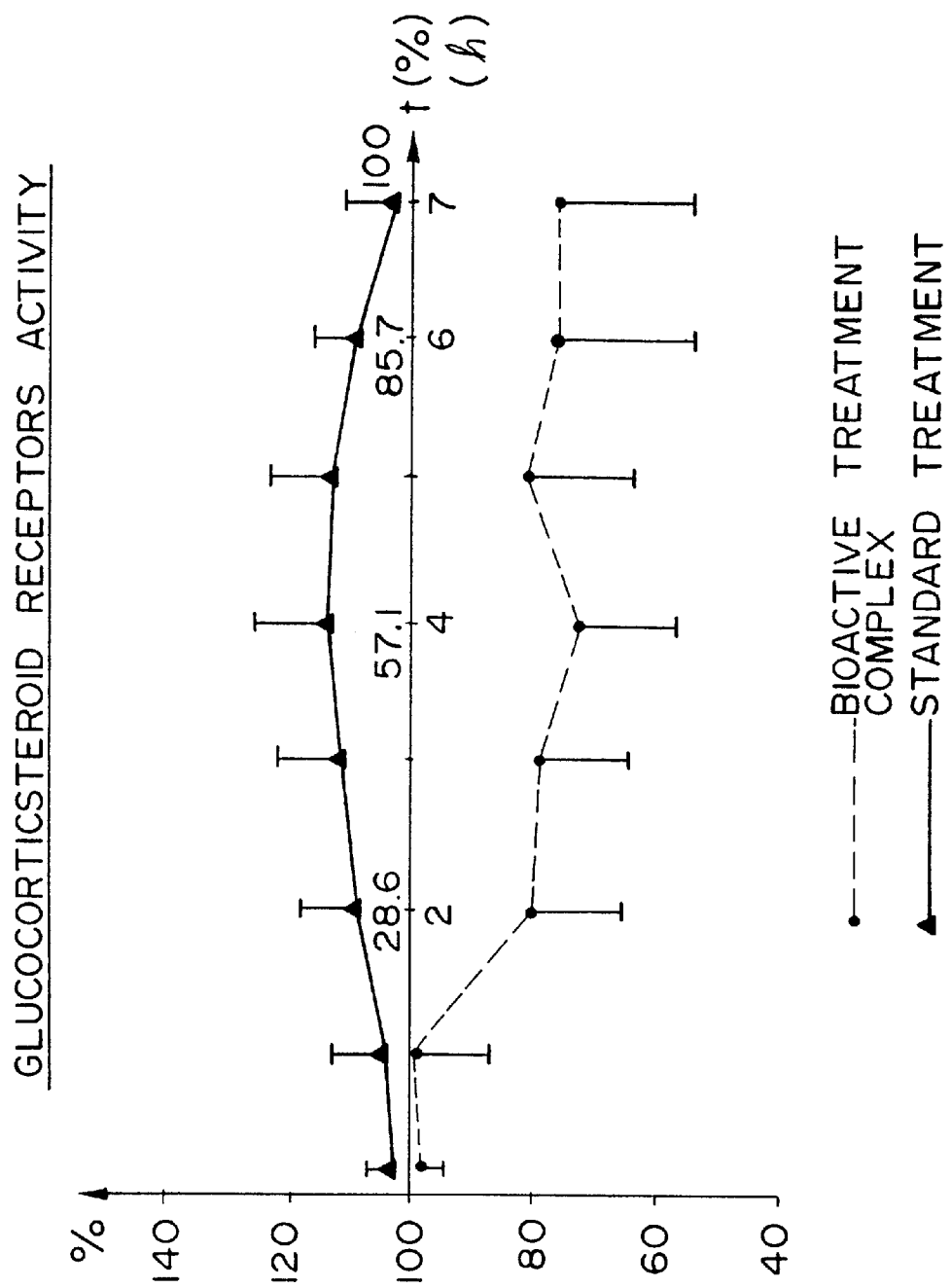
FIG. 10 is a graph showing the results of the effects of a composition of the instant invention versus the effect of standard treatment in anesthetized dogs post trauma on glucocorticosteroid receptors activity.
Figure 11:
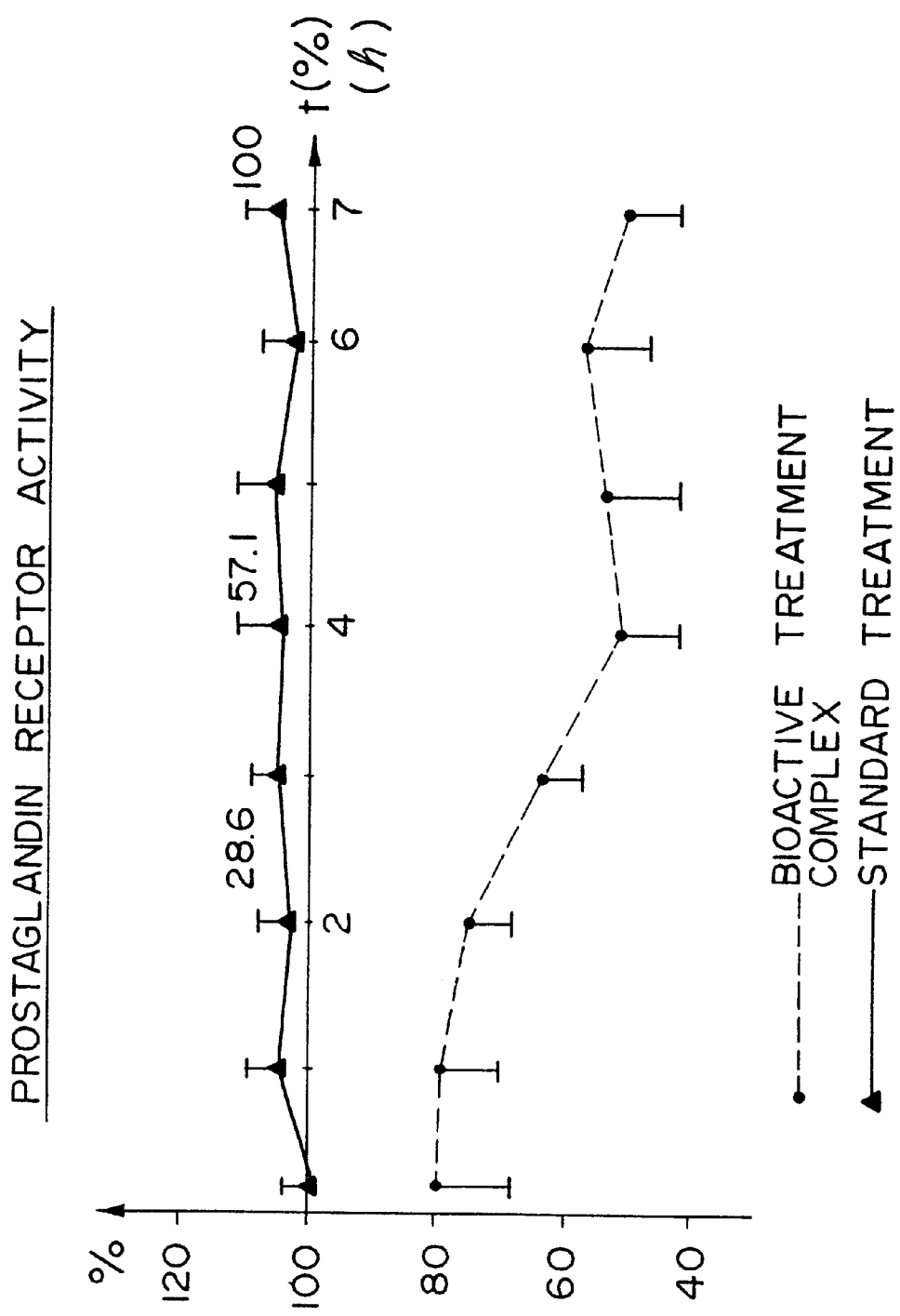
FIG. 11 is a graph showing the results of the effects of a composition of the instant invention versus the effect of standard treatment in anesthetized dogs post trauma on prostaglandin-receptor activity.
Figure 12:
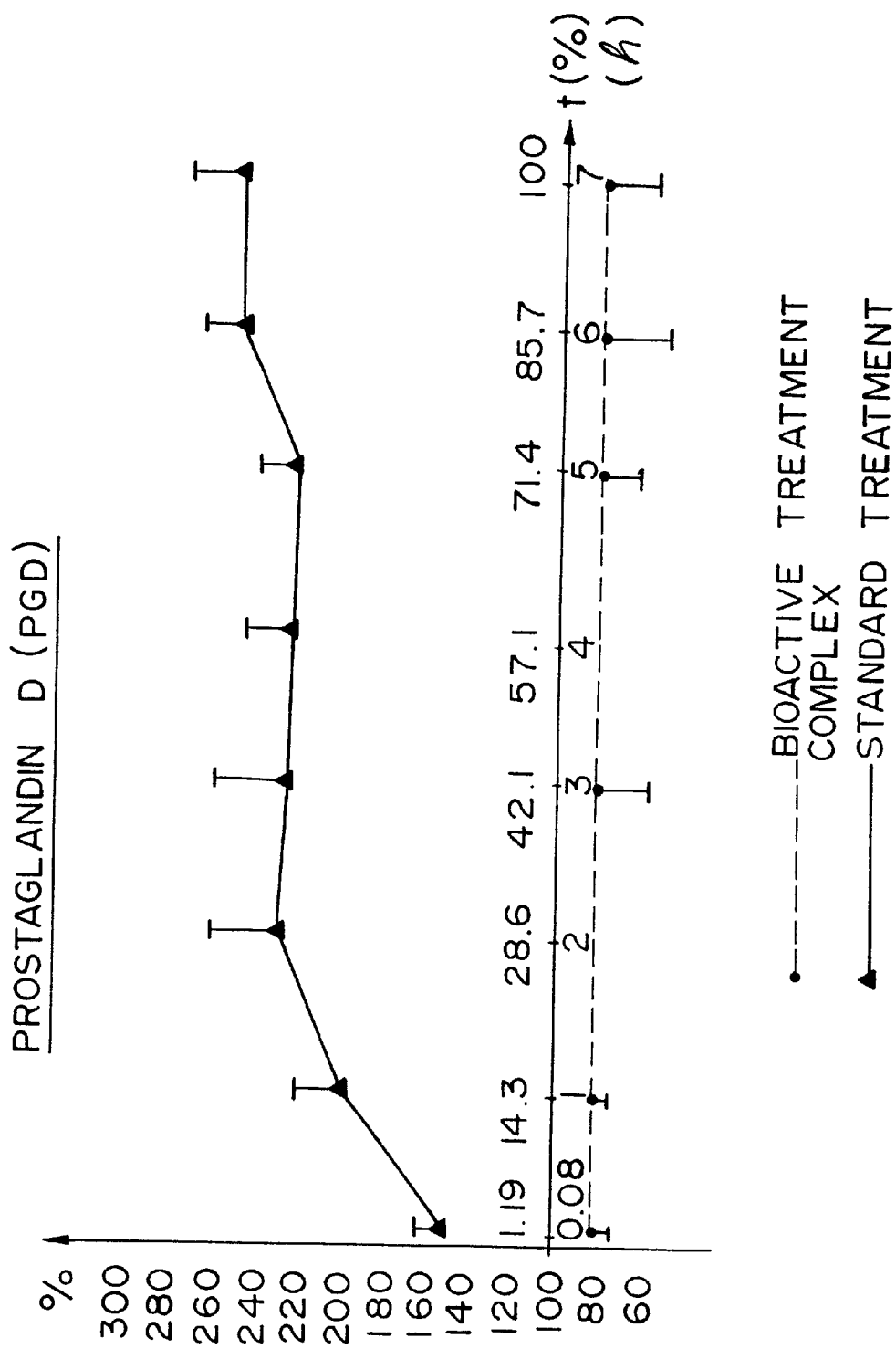
FIG. 12 is a graph showing the results of the effects of a composition of the instant invention versus the effect of standard treatment in anesthetized dogs post trauma on prostaglandin D (PGD).
Figure 13:
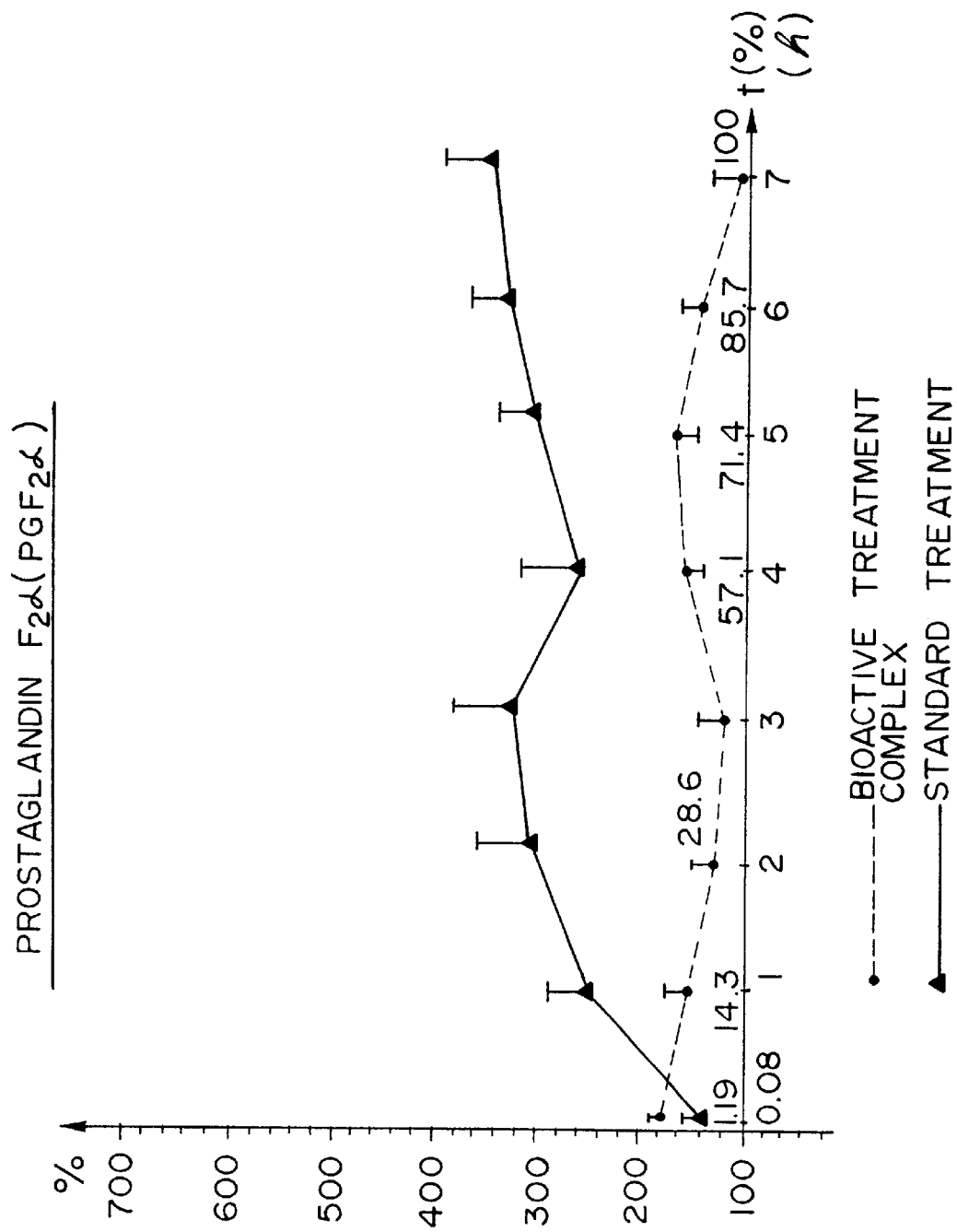
FIG. 13 is a graph showing the results of the effects of a composition of the instant invention versus the effect of standard treatment in anesthetized dogs post trauma on prostaglandin $F_{2\alpha}$ ($PGF_{2\alpha}$).
Figure 14:
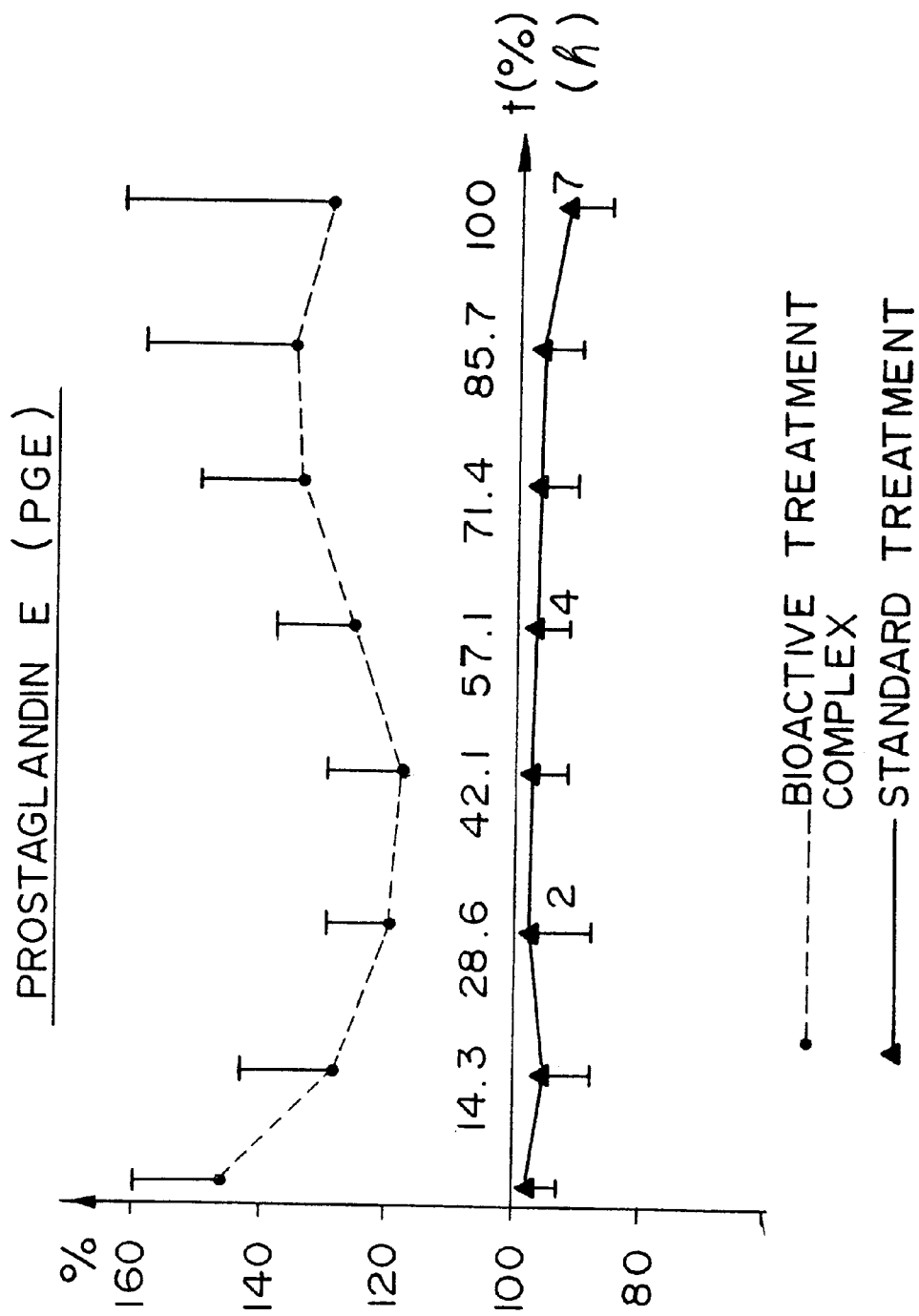
FIG. 14 is a graph showing the results of the effects of a composition of the instant invention versus the effect of standard treatment in anesthetized dogs post trauma on prostaglandin E (PGE).
Figure 15:
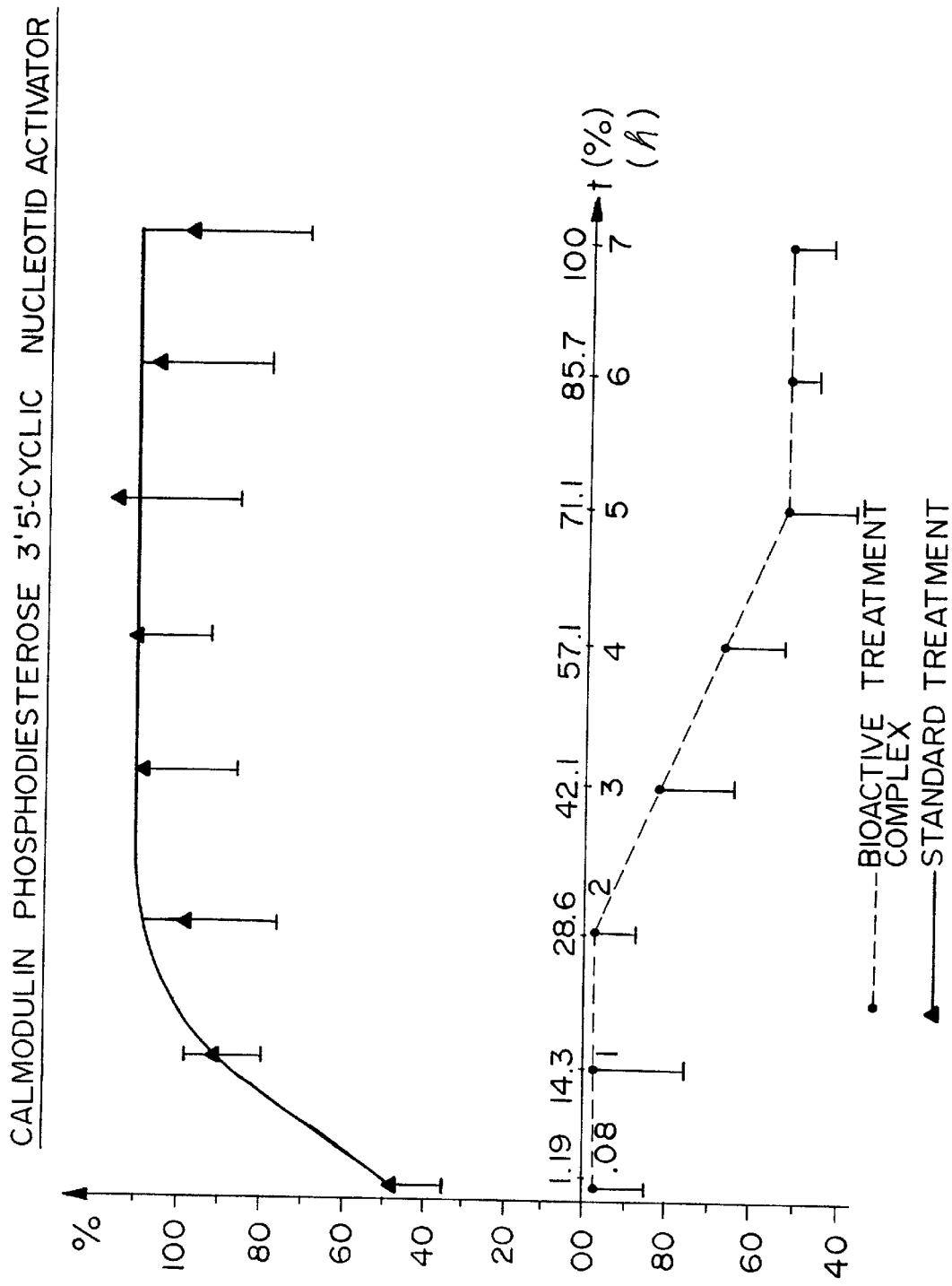
FIG. 15 is a graph showing the results of the effects of a composition of the instant invention versus the effect of standard treatment in anesthetized dogs post trauma on calmodulin (Phosphodiesterase 3'5'-cyclic nucleotide activator).
Figure 16:
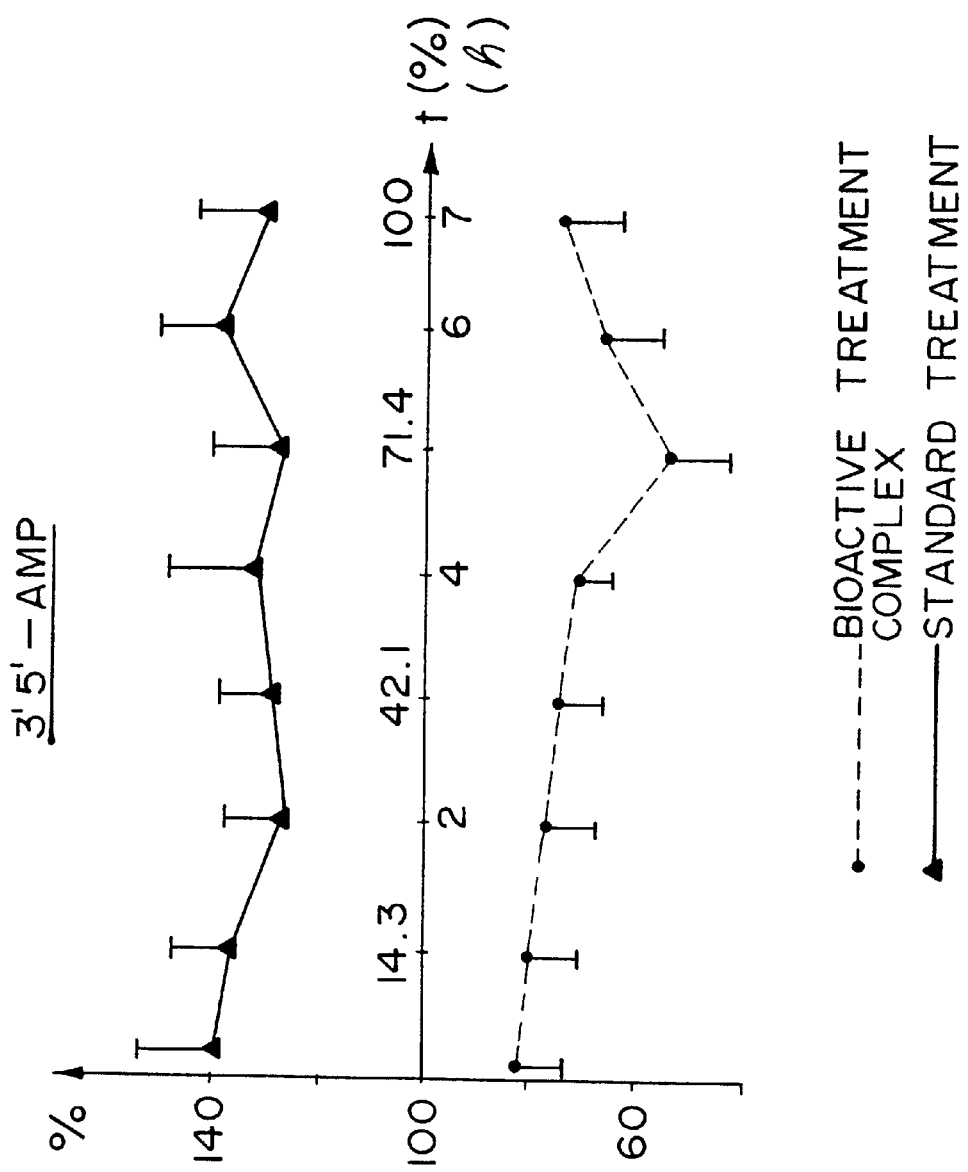
FIG. 16 is a graph showing the results of the effects of a composition of the instant invention versus the effect of standard treatment in anesthetized dogs post trauma on 3'5'-AMP (Cyclic 3'5'-adenosine monophosphate).
Figure 17:
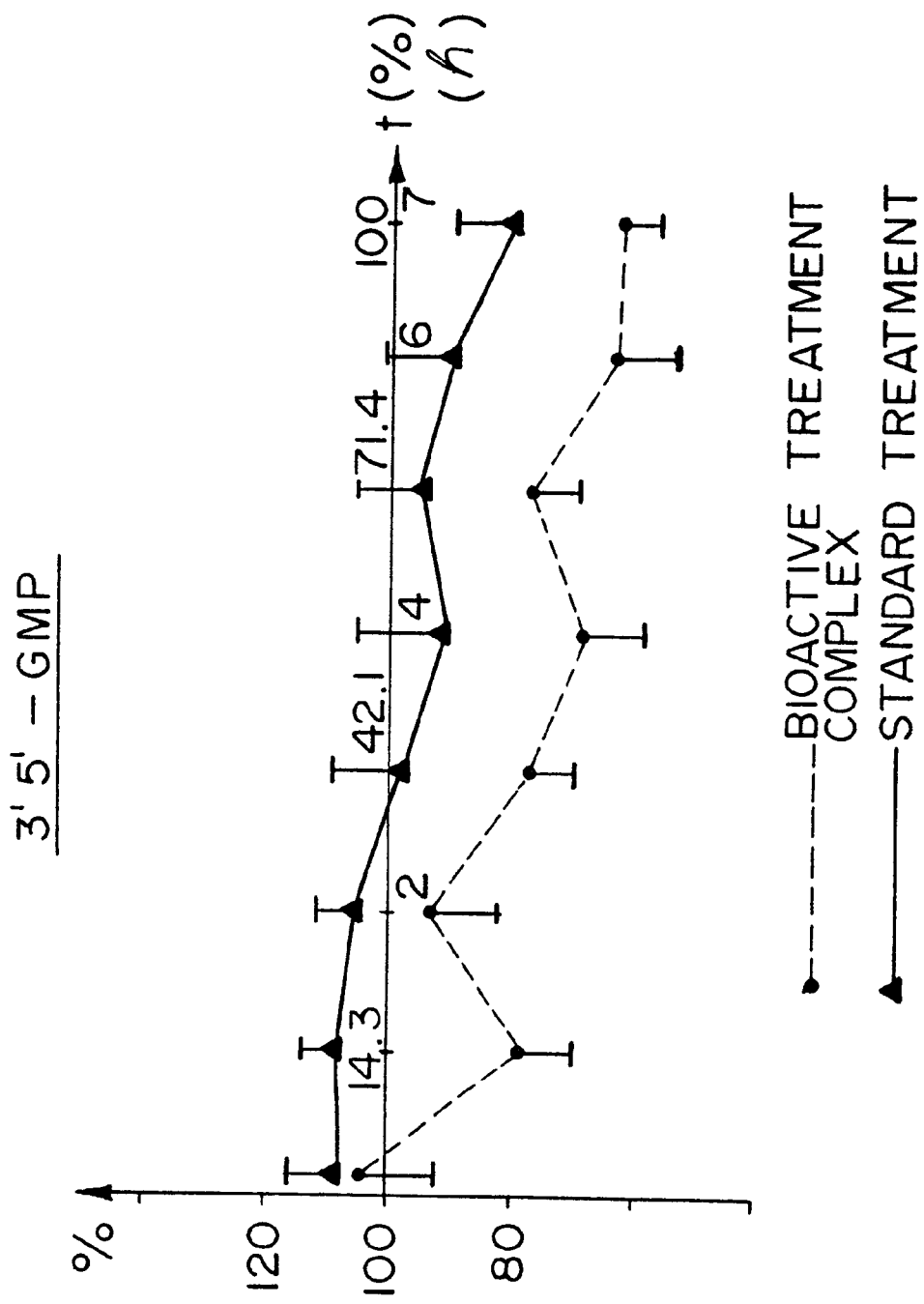
FIG. 17 is a graph showing the results of the effects of a composition of the instant invention versus the effect of standard treatment in anesthetized dogs post trauma on 3'5'-GMP (Cyclic 3'5'-guanosine monophosphate).
Figure 18:
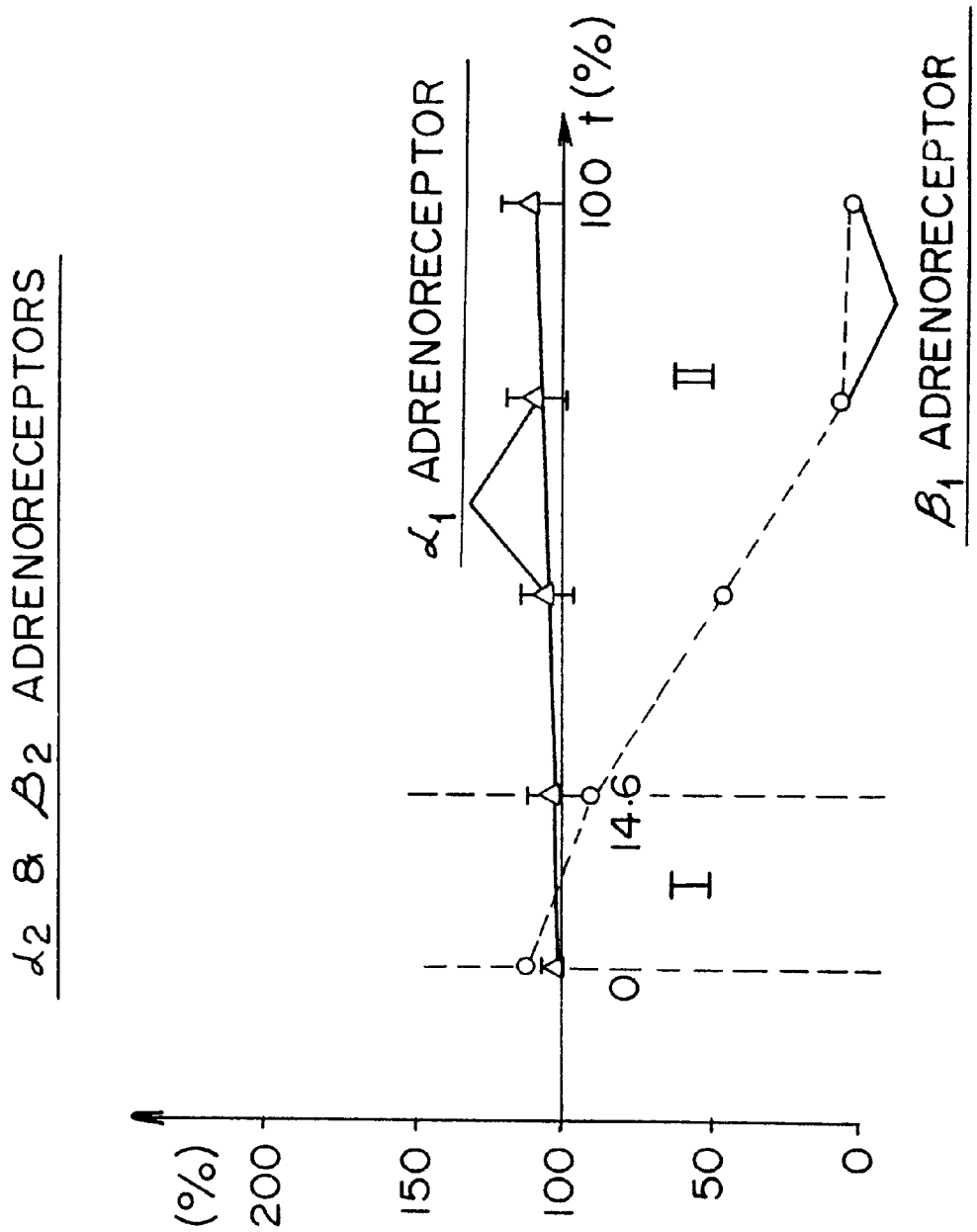
FIG. 18 is a graph showing the relative amounts of the $\alpha_2$ and $\beta_2$ adrenoreceptors after topical administration of a biocomplex of the instant invention.
Figure 19:
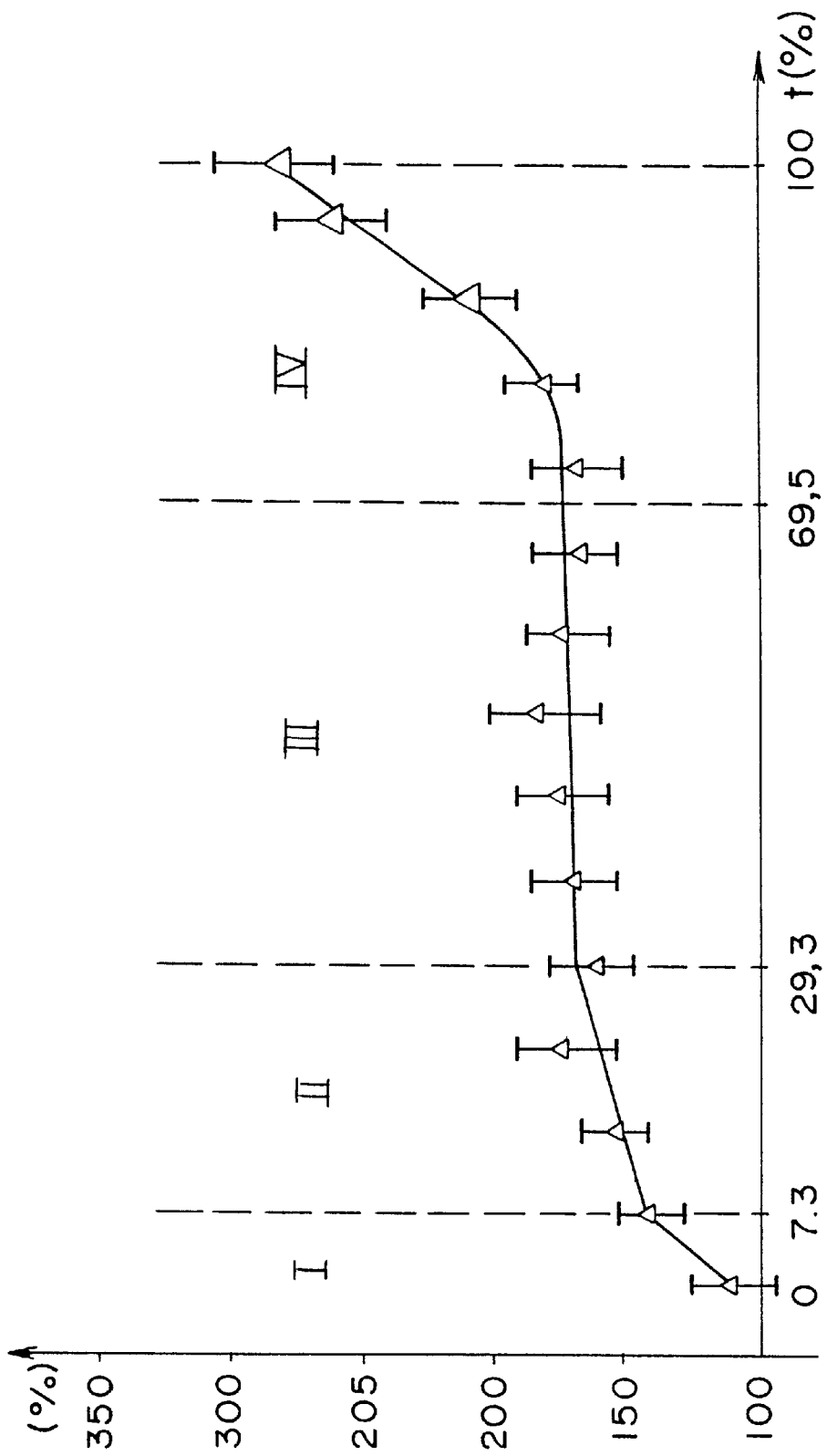
FIG. 19 is a graph showing the relative amounts of integral local microcirculation after topical administration of a biocomplex of the instant invention.
Figure 20:
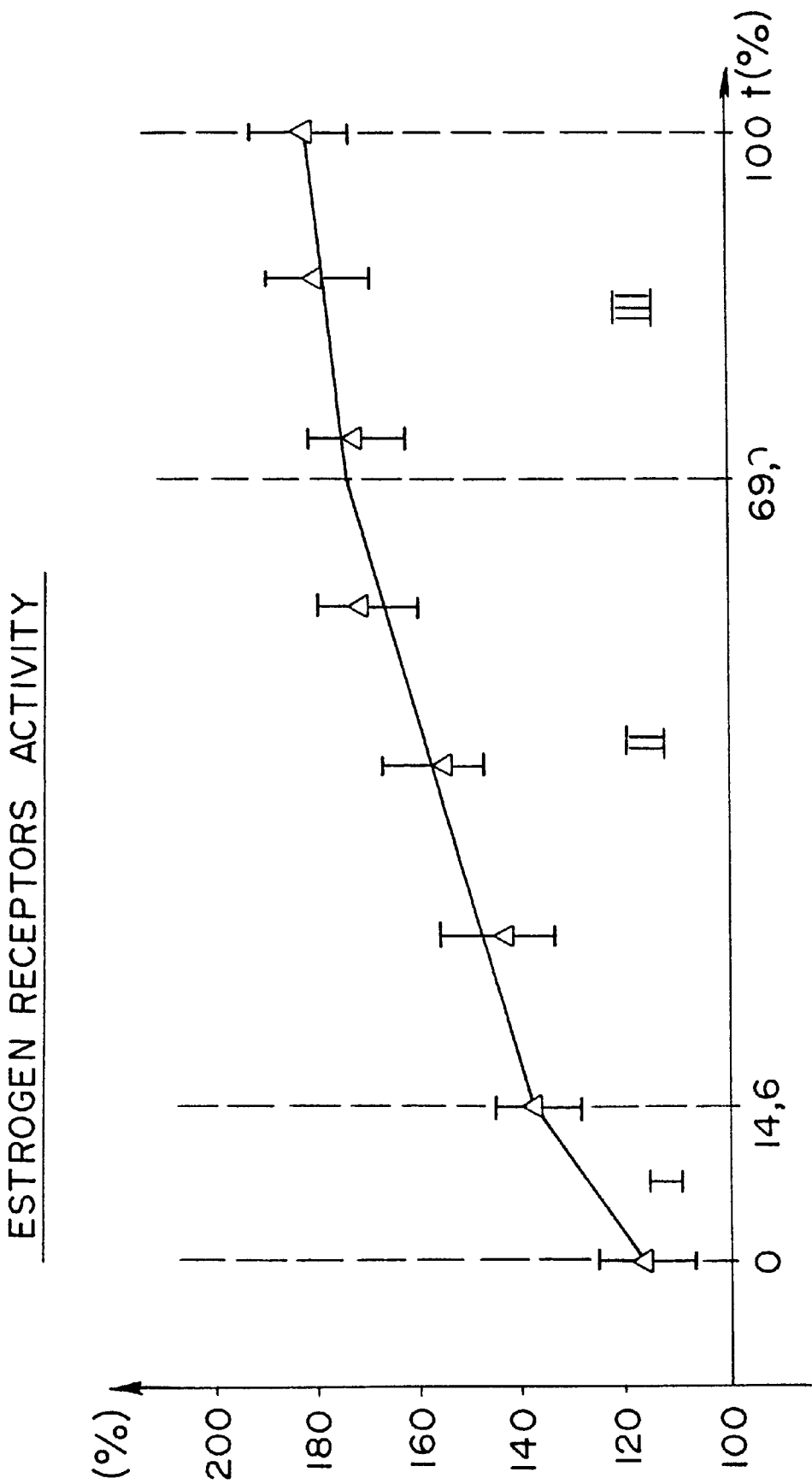
FIG. 20 is a graph showing the relative amounts of estrogen receptors activity after topical administration of a biocomplex of the instant invention.
Figure 21:
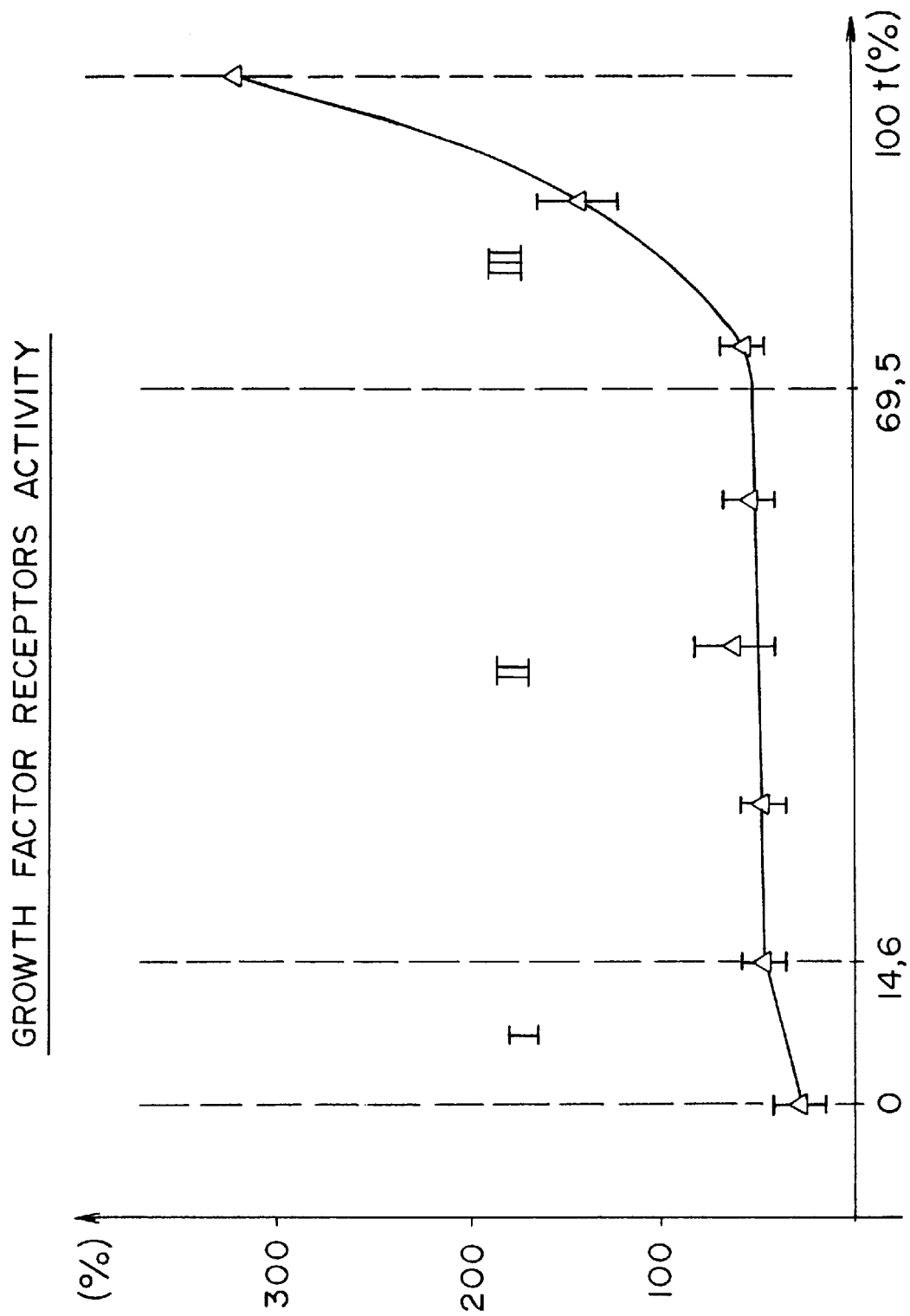
FIG. 21 is a graph showing the relative amounts of growth factor receptors activity after topical administration of a biocomplex of the instant invention.
Figure 22:
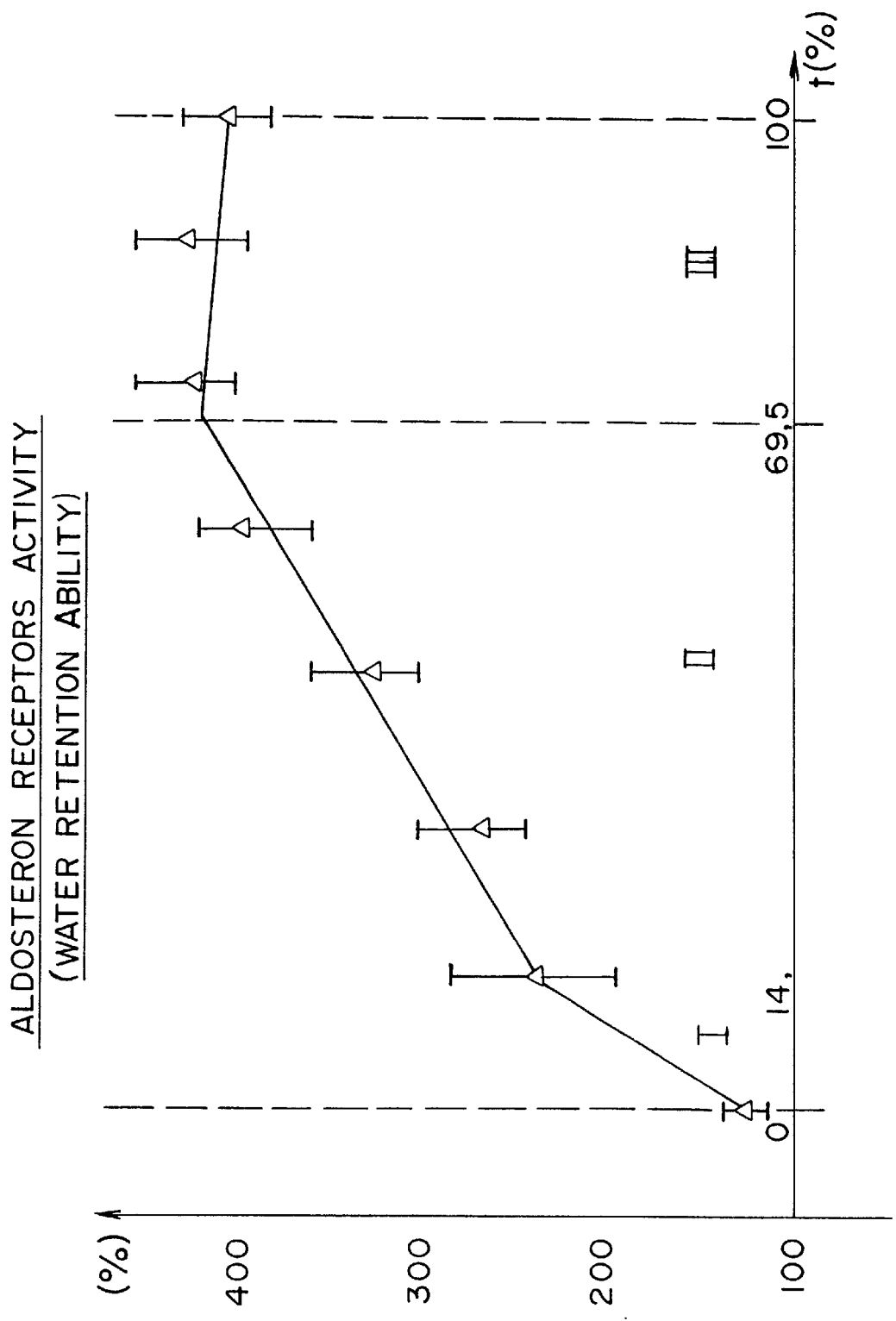
FIG. 22 is a graph showing the relative amounts of aldersterone receptors activity (water retention ability) after topical administration of a biocomplex of the instant invention.
Figure 23:
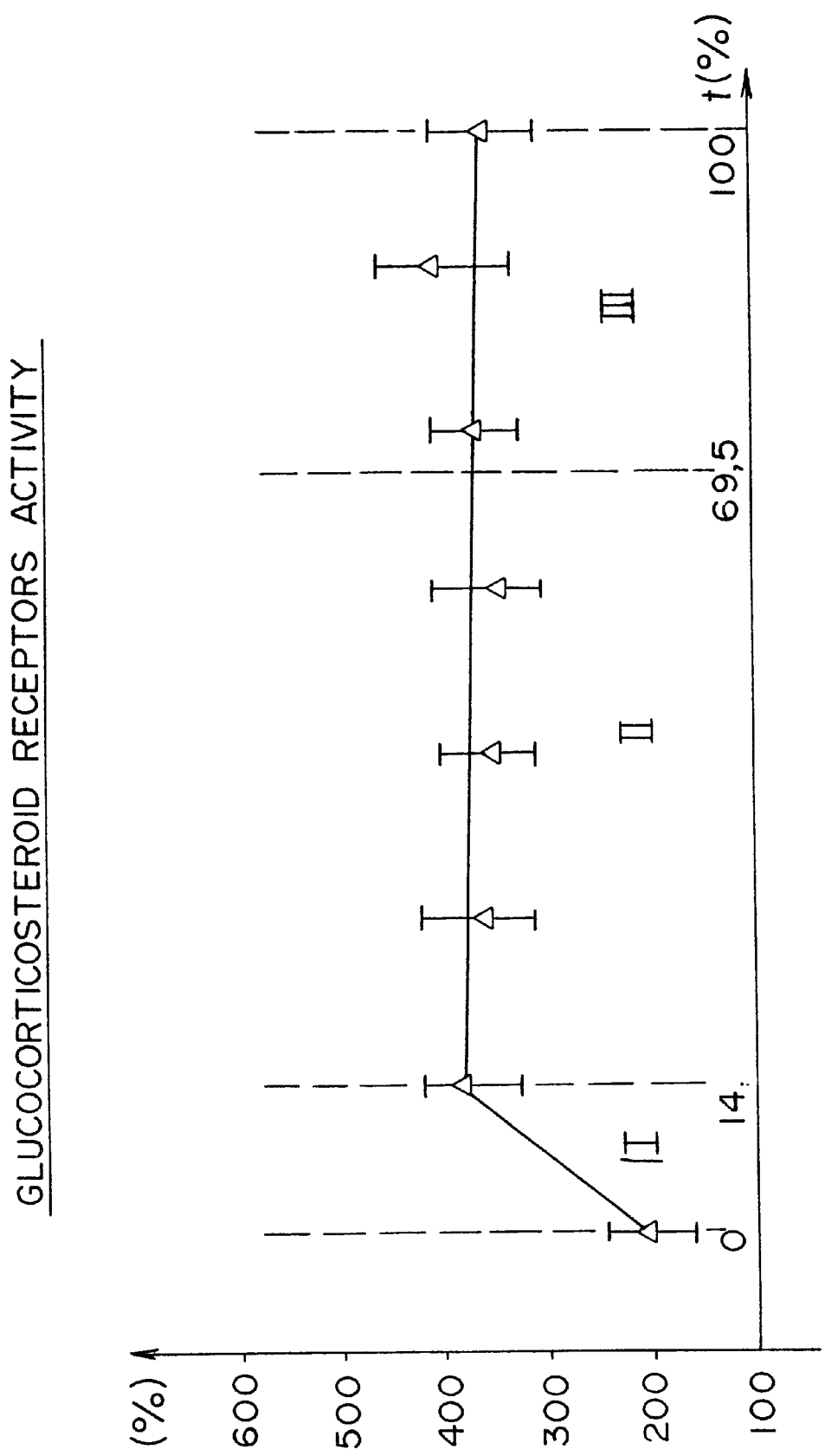
FIG. 23 is a graph showing the relative amounts of glucocorticosteroid receptors activity after topical administration of a biocomplex of the instant invention.
Figure 24:
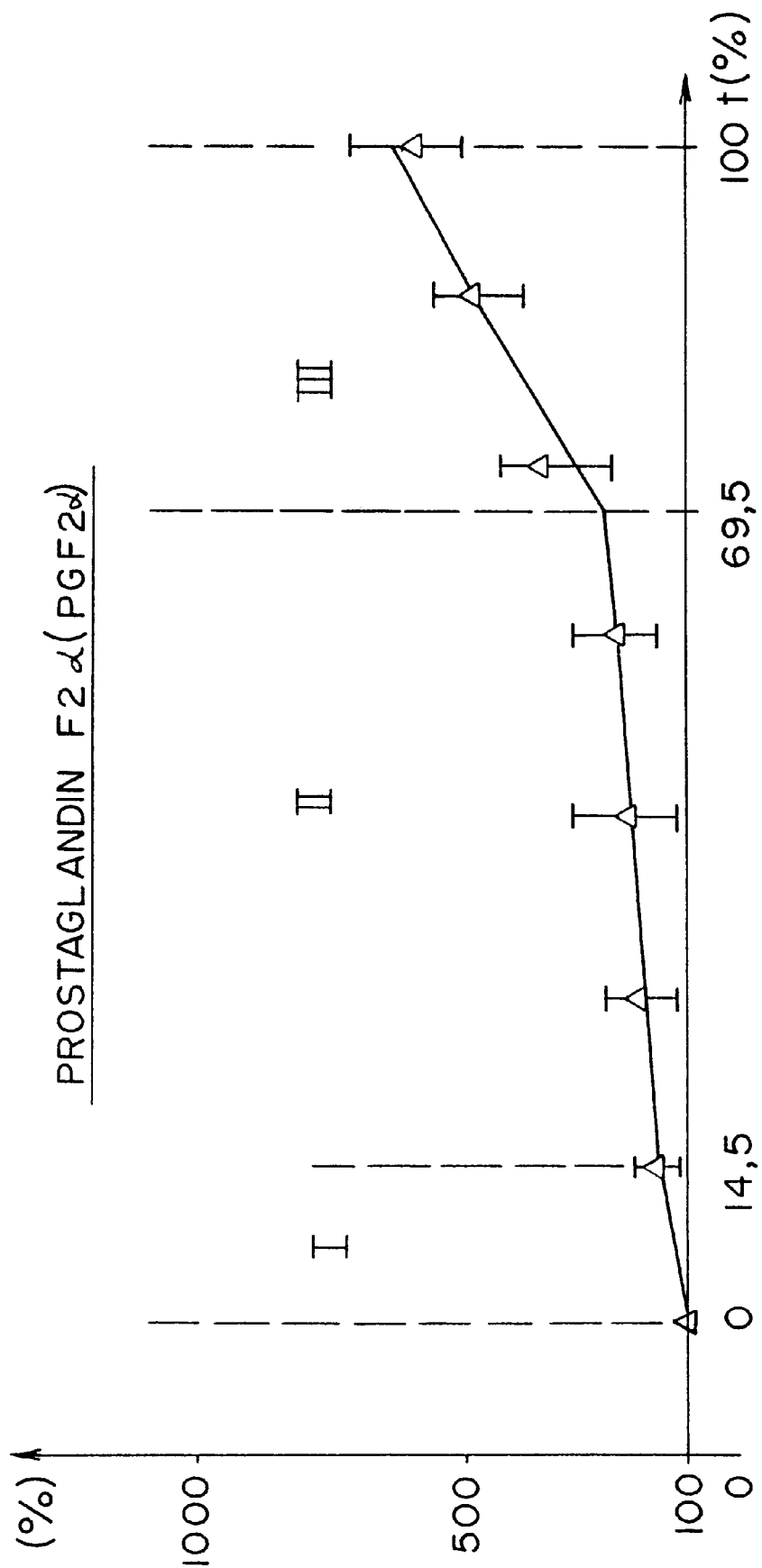
FIG. 24 is a graph showing the relative amounts of prostaglandin $F_{2\alpha}$ activity after topical administration of a biocomplex of the instant invention.
Figure 25:
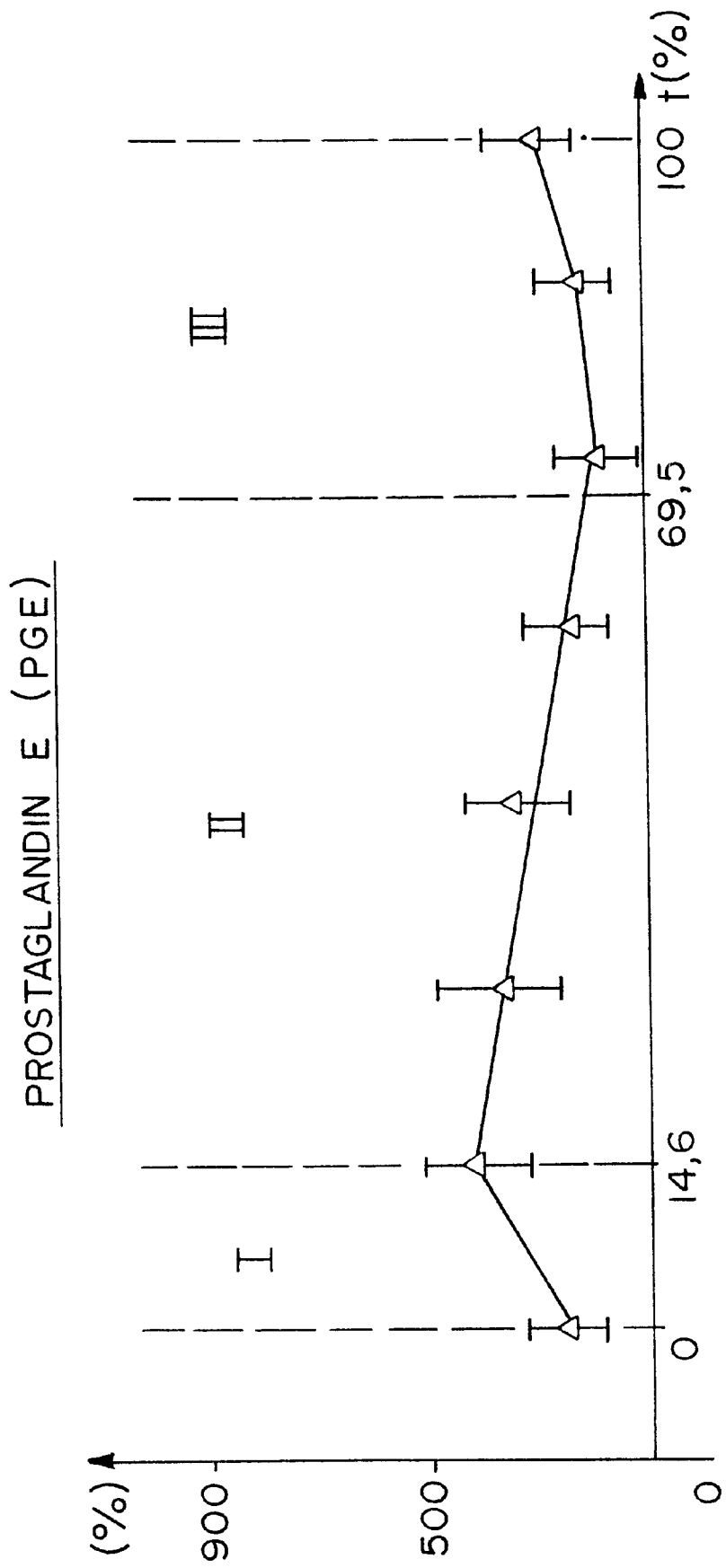
FIG. 25 is a graph showing the relative amounts of prostaglandin E activity after topical administration of a biocomplex of the instant invention.
Figure 26:
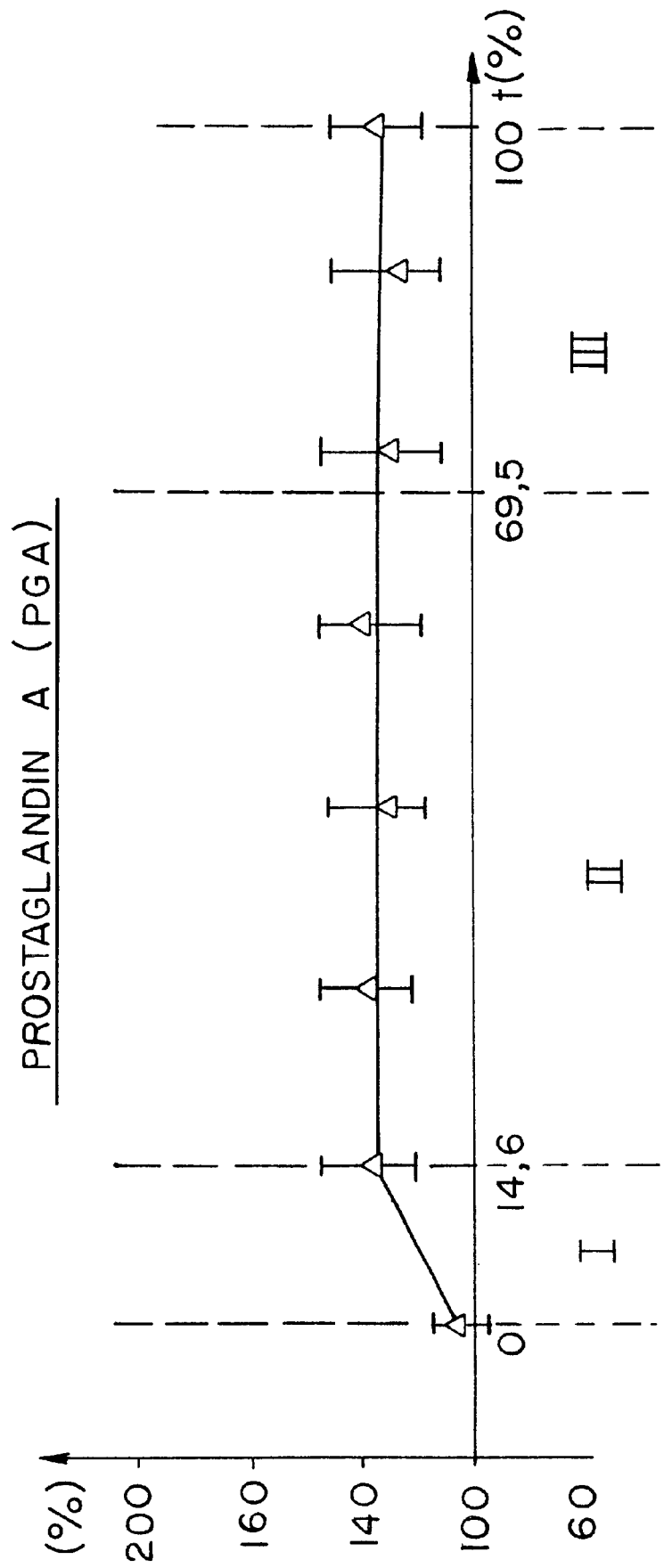
FIG. 26 is a graph showing the relative amounts of prostaglandin A activity after topical administration of a biocomplex of the instant invention.
Figure 27:
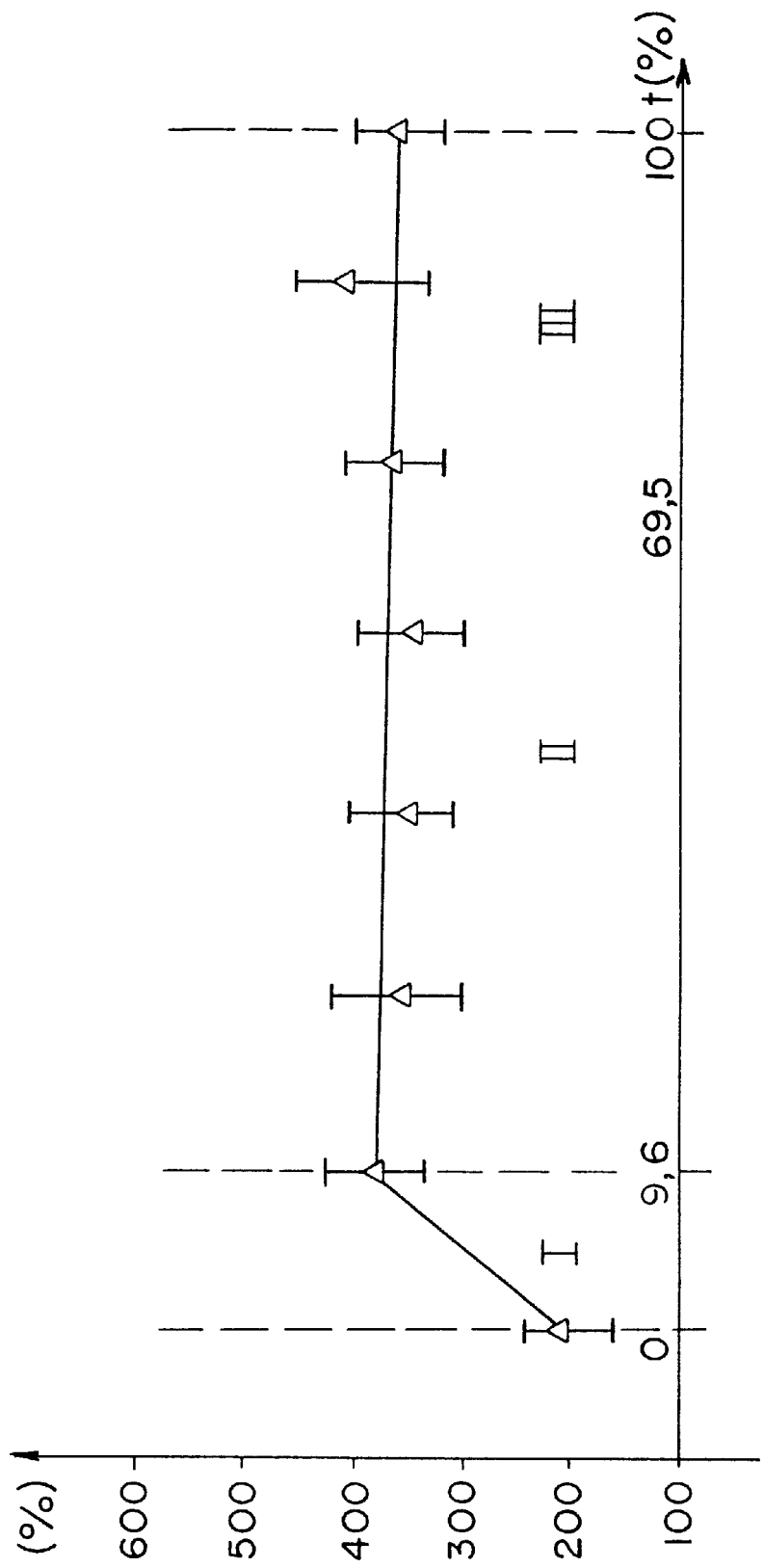
FIG. 27 is a graph showing the relative amounts of calmodulin (phosphodiesterase 3'5'-cyclic nucleotide activator) activity after topical administration of a biocomplex of the instant invention.
Figure 28:
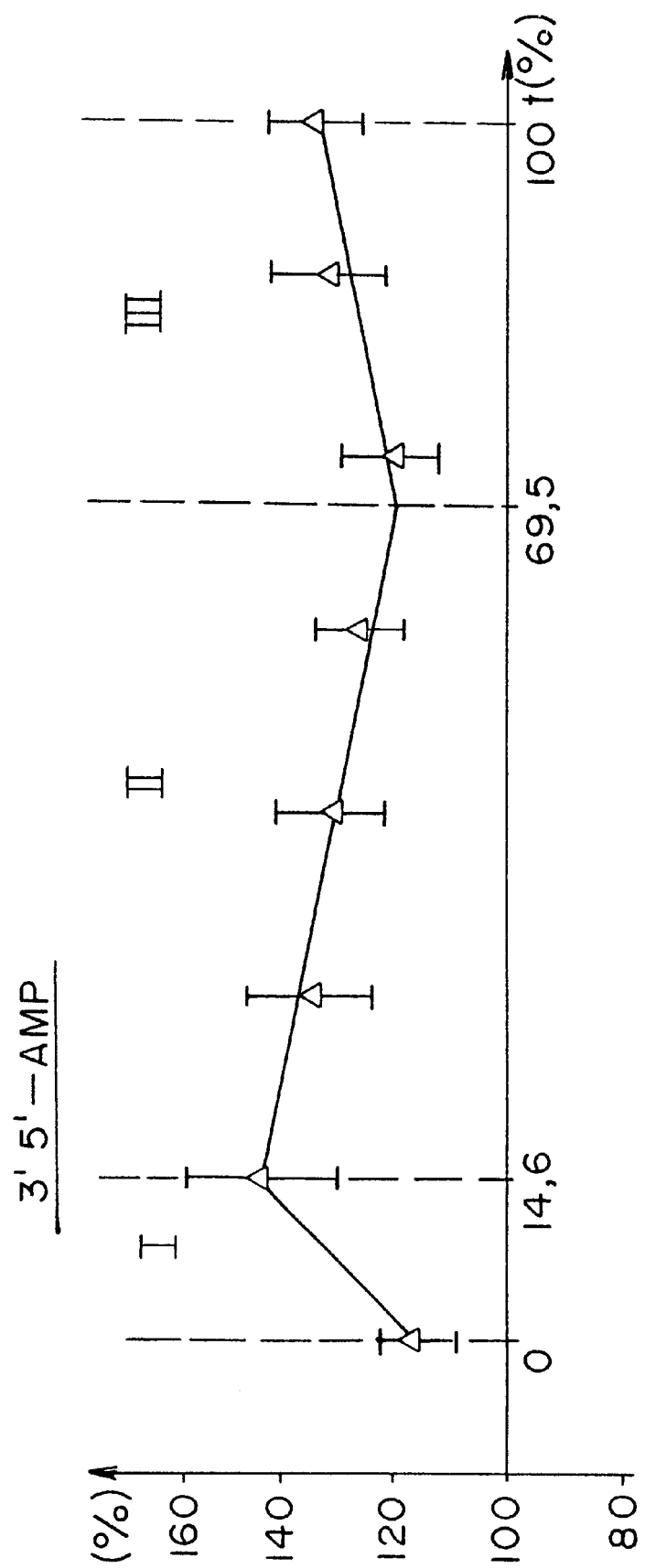
FIG. 28 is a graph showing the relative amounts of 3'5'-AMP (Cyclic 3'5'-adenosine monophosphate) activity after topical administration of a biocomplex of the instant invention.
Figure 29:
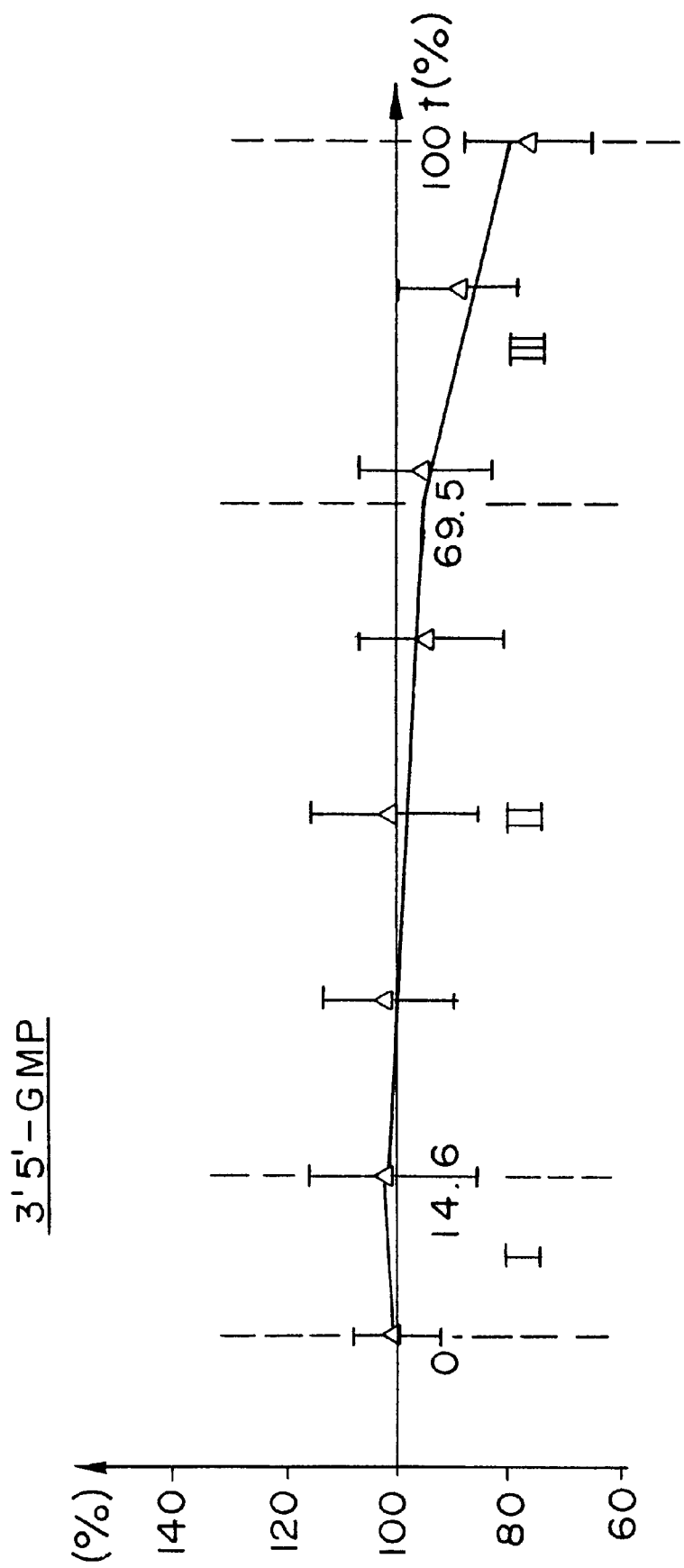
FIG. 29 is a graph showing the relative amounts of 3'5'-GMP (Cyclic 3'5'-guanosine monophosphate)activity after topical administration of a biocomplex of the instant invention.
Figure 30:
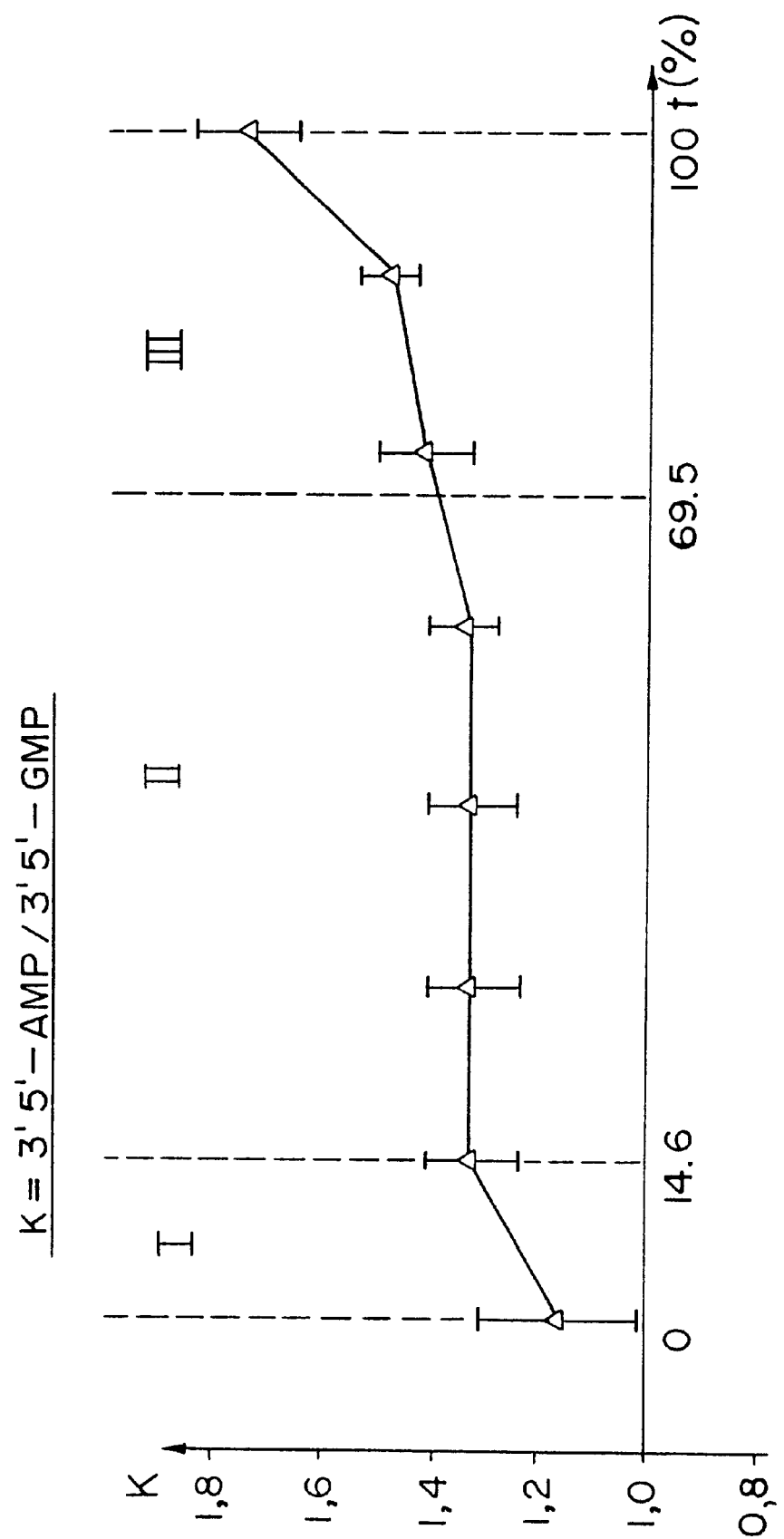
FIG. 30 is a graph showing the relative amounts of 3'5'-AMP/3'5'-GMP activity after topical administration of a biocomplex of the instant invention.

The compositions of the present invention comprise at least one bioactive agent from each of the three informational blocks of biological information transfer, each agent being present in an amount sufficient to correct the biological information transfer of the patient under treatment and resulting in the resumption of normal cell metabolism, said amount being less than the buffering amount of said agent; together with a biologically acceptable carrier therefor. These informational blocks, complexes, agents and their relationship are shown in the diagram of FIG. 3.

The amount and concentration of the bioactive agents in the compositions of the present invention is critical to the instant invention. The amount of each bioactive agent is generally of the same order of magnitude as the amount of the bioactive agent found in naturally occurring organisms. This amount is chosen so as to not exceed the "buffering mechanism" of the organism. For the purposes of this invention, an amount which does not exceed the buffering mechanism of the organism is that amount which the organism can normally biologically eliminate from its cells.

Typically, therapeutic agents are administered in such large doses so as to overwhelm the normal biological information transfer system. The therapeutic methods of the present invention differ radically from such dosages in that the compositions utilizing the bioactive agents contain the agents in amounts which are similar to those amounts found in normal living organisms with a normal functioning biological information transfer system. Depending upon the precise therapy, the compositions of the present invention thus contain the bioactive agents in amounts ranging from about those found in such normal living organisms to about two or three times the amount found in normal living organisms.

In the case where support, preservation or mild correction of the biological information transfer disfunction is needed, the amount utilized in the composition will be within the values observed in the organism, i.e., the basal concentration will be that which is observed in a normally functioning organism with an optimum mode of biological information transfer.

In more severe pathologies where acute dysfunction of regulating system are present or particular pathological processes are present, intensive interference and/or restoration of the disrupted biological information transfer is necessary. In these cases, concentration of the bioactive agents is much higher, e.g., on the order of two to three times the amount observed in a normally functioning organism with an optimum mode of biological information transfer. However, even when higher amounts of the bioactive agents are present in the compositions of the present invention, the amounts still do not exceed the buffering mechanism of the organism for the particular bioactive agent in question.

The bioactive agents utilized in the compositions of the present invention are selected after a careful analysis of the pathology under treatment. While there is a wide range of bioactive agents which can be utilized, the selection is narrowed once the particular pathology has been selected. Obviously, something of the biochemical origin of the selected pathology must be known, but once this information is known, then the bioactive agents are selected so as to provide a composition wherein at least one agent is present from each of the three informational blocks. Typically, and preferably, the composition will contain more than one agent from each of the three informational blocks.

Thus, the compositions of the present invention contain bioactive agents from each of the three informational blocks to ensure the restoration/support of normal biological information transfer, and the restoration of normal cell metabolism.

In the case where the composition of the present invention is utilized for the support, preservation or mild correction of the biological information transfer dysfunction, the composition can be limited to bioactive agents from the third informational block—one or more informational group of informational complexes 6 (see Scheme VI).

Each of the information blocks consist of informational complexes, which, in turn, include informational agents grouped on the basis of their common effect mechanism on the information transfer level. Theses informational blocks, informational complexes and informational agents, and their relationship are shown diagrammatically in FIG. 3.

The first type of these informational complexes consists of first degree information substances modulating the overall effects of the chain of information transfer. This complex consists of informational agents such as various biologically active substances and/or hormones and/or medicinal remedies, which are responsible for the transfer of information with the first information level. Typical agents are given in Scheme I below.

SCHEME I

Informational Complex #1
Complex of the First Degree Informational Substances (first degree messengers)
    Informational agents for informational complex #1
1.0 Protein-Peptide Substances
    1.1 Hypothalamic releasing factor
    1.2 Hypophysis hormones
    oligopeptide hormones—ACTH type:
      adrenocorticotrophin (ACTH); adrenocorticotropic hormone
      β-lipotropin (β-ITP)
      α-melatoninstimulate hormone (α-MSH)
    Monomeric proteins:
      growth hormone (STH; HGH)
      prolactin
    Glycoprotein dimeric hormones:
      follicle-stimulating hormone (FSH)
      luteinizing hormone (LN)
      thyroid-stimulating hormone (TSH)
    Neurohypophysis hormones:
      vasopressins
      oxytocin
    1.3 Polypeptide hormones which regulated Ca and P metabolite
    parathyroid hormone (PTH); parothormone
    calciotonin
    1.4 Angiotensins and related peptides
    1.5 Oligopeptide hormones of the gastro-enteropancreatic (GEP) system (gastrointestinal peptides)
    neuropeptides of the GEP system
    APUD polypeptide hormones
    glucagon
    1.6 Polypeptide hormones of the pancreas
    insulin
    C-peptide
    1.7 Oligopeptide hormones of the thymus
    thymozin I and II
    thymopoethins I and II
    thymosterin
    homeostatic glycoprotein
    1.8 Opioid peptides
    endorphins
    enkephalins
    1.9 Somatomedins
    1.10 Additional bioactive peptides
2.0 Steroid Hormones
    2.1 $C_{21}$-steroids (pregnanesteroid hormones)
    corticosteroids
      glucocorticoids
      mineralocorticoids
    progestins (gestagens)
    2.2 $C_{19}$-steroids (androstones steroid hormones)
    androgens
    2.3 $C_{18}$-steroids (estranes steroid hormones)
    estrogens
    2.4 $C_{27}$-steroids (cholestanes steroid hormones)
    1α, 25-dioxy-vitamin $D_3$
    ecdizons
    2.5 Additional bioactive steroids
3.0 Amino Acids Derivatives
    3.1 Catecholamines
    dopamine
    norepinephrine (noradrenalin)
    epinephrine (adrenalin)
    3.2 Thyroid hormones
    thyroxine ($T_4$)
    triiodothyronine ($T_3$)
    3.3 Neurotransmitters
    3.4 Porphyrins and bile pigments
    3.5 Tryptophane derivatives
    melatonin
    3.6 Additional bioactive amino acids derivatives
4.0 Artificial Active Substances—Drugs
    Majority of medications which possess stereochemical affinity with the cell/tissue structures of organism.

The second type of these information complexes consists of complexes of cellular receptors (membranes and/or cytosol and/or intranuclear) with its specific cell membrane and/or intracellular decoding systems. This complex includes informational agents responsible for the information transfer on the second informational level. Agents of this type are described in Scheme II below.

SCHEME II

Informational Complex #2
Complex of Cell Receptors with Specific Decoding Agent
Informational Agents for Informational Complex #2
1.0 Specific Cell Receptors
    1.1 Cell membrane receptors
    individual receptors for protein-peptide hormones, catecholamines 1.2 Cytoplasm (cytosol) receptors
    individual receptors for steroid hormones
    1.3 Nuclear receptors
    individual receptors for thyroid hormones
    1.4 Additional receptors with stereochemical affinity to first degree messengers
2.0 Cell Membrane Triggers
    2.1 Adenyl cyclase (adenylatcyclase)
    2.2 Guanyl cyclase (guanylatcyclase)
    2.3 Phosphodiesterase
    2.4 Glycoproteins 2.5 Phosphatidylserin
3.0 Phosphorylate Precursors
   3.1 Adenosine triphosphate (ATP)
   3.2 Guanosine triphosphate (GTP)
   3.3 Phosphatidylinositol-4-5-diphosphate ($PIP_2$)
   3.4 Various types of phosphoinositides
4.0 Additional Membrane Triggers and Phosphorylate Precursors (Decoding Agents)

The third type of these information complexes consists of complexes of transmembrane and intracellular conjunction agents providing for nonspecific activation of signal transfer on the second informational level. This complex includes various lipids, phospholipids, and cell membrane components. These agents promote the effective realization of information transfer both on the second level and in the course of further information transfer from the second to the third informational level. Typical agents of this type are given in Scheme III below.

SCHEME III

Informational Complex #3
Complex of Transmembrane and Intracellular Conjunction Agents
   Informational agents for informational complex #3
1.0 Phospholipids
   phosphatidylcholines (lecithins)
   phosphatidylethanolamines (cephalins)
   phosphatidylglycerols
   phosphatidylinositols
   modified phospholipids
2.0 Unsaturated Fatty Acids
3.0 Saturated Fatty Acids
4.0 Glycolipids
   4.1 Neutral glycosphingolipids
   4.2 Acidic glycosphingolipids
5.0 Structural (Ground) Proteins (Peptides)
6.0 Glycosaminoglycans
   6.1 Chrondriotin 4 and 6 sulfates
   6.2 Keratane sulfate
   6.3 Hyaluronic acid
   6.4 Dermatan sulfate
   6.5 Heparin
   6.6 Heparin sulfate
   6.7 Additional glycosoaminoglycans
7.0 Substitute Cell Membrane
   Active substances composed substitute cell membrane (SCM)

The fourth type of these information complexes consists of complexes of intracellular second degree messengers and multifactor activators providing for the decoded initial information transformation into the final output cellular signal. These agents are responsible for transformation of molecular signals into the biochemical reaction of the cell. Depending on the goal and task at hand it is possible to prepare information complexes both with a very wide range of action, and conversely, with a a narrowly directed activity of one or two systems of information transfer on the third level. If desired, it a is possible to prepare these informational complexes with an extended range of intracellular second degree messengers and multifactor activators, which will ensure the increase of cell transformation (with a simultaneous effect exerted by informational complexes of the second type). Agents of this type are described in Scheme IV below.

SCHEME IV

Informational Complex #4
Complex of Intracellular Second Degree Messengers and Multifactor Activators
   Informational agents for informational complex #4
1.0 Second Degree Messengers
   1.1 Cyclic nucleotides
   cyclic adenosine monophosphate (3'5'-AMP);
   cyclic guanosine monophosphate (3'5'GMP):
   1.2 Diacylglycerols (DG)
   1.3 Inositol triphosphate ($IP_3$)
   1.4 Calmodulin
2.0 Multifactor Activators (Multiple Activators)
   2.1 Ionic forces
   Calcium ions ($Ca^{+2}$)
   2.2 Intracellular cascade system components
   Protein kinase systems (protein kinase and related peptides)
   2.3 Additional multifactor activators compounds
   2.4 Nucleotide coenzymes (coenzyme A; NAD; NADP, etc.)

The fifth type of these informational complexes are complexes of intracellular transmitters and trigger system, which provide for nonspecific activation of decoded signal transformation into the biological response of the cell. Included in such complexes are the prostaglandins of various types, and/or thromboxans and/or prostacyclins. These complexes thus ensure the normal functioning of the intracellular information volume. Examples of these complexes are given in Scheme V below.

SCHEME V

Informational Complex #5
Complex of Nonspecific Intracellular Transmitters and Trigger Systems
   Informational agents for informational complex #5
1.0 Prostaglandins
   Various groups of prostaglandins
2.0 Prostacyclins
3.0 Thromboxanes
4.0 Leukotrienes The sixth type of these information complexes are complexes which increase or weaken biological information transfer. These types of complexes are those which include vitamins and their coenzymes, complex structural proteins, enzymes, lipids, etc. Examples of these complexes are given below in Scheme VI.

SCHEME VI

Informational Complex #6
Complex of Additional Biologically Active Triggers Independent Informational Groups which Represent Informational Complex #6
   Informational complex #6 has a relative meaning because it practically includes a great many absolutely independent complexes, which can be provisionally called groups. In other words, this complex is represented not by one particular set of information agents but by a whole series of entirely independent informational complexes, each of which influences the particular links of the biological information transfer chain. Informational groups are completely independent; therefore, different groups of informational complex #6 can be simultaneously present in the structure of various informational blocks. Informational groups of the information complexes of the sixth type can be used independently for the restoration of normal cell metabolism to provide therapeutic and cosmetic methods of treating various cell dysfunctions.

1.0 Vitamins with Cofactors (Coenzymes) Group
   Consisting of: oil-soluble vitamins
   water-soluble vitamins
   coenzymes (cofactors)
2.0 Choline Chloride Group
3.0 Low Density Lipoproteins (LDL)
   Consisting of: unsaturated fatty acids
   saturated fatty acids
   triacylglycerol with saturated fatty acids
   triacylglycerol with unsaturated fatty acids
   phospholipids
   cholesterol
   peptides
4.0 Very Low Density Lipoproteins (VLDL)
5.0 High Density Lipoproteins (HDL)
   Consisting of: unsaturated fatty acids
   triacylglycerol with unsaturated fatty acids
   phospholipids
   cholesterol
   peptides
6.0 Lipases Group
7.0 Carbohydrates Group
8.0 Lipids Group
9.0 Additional Bioactive Groups The bioactive components of the compositions of the instant invention can be selected from a wide variety of such agents presently utilized in the pharmaceutical, dermatological and cosmetic industry. Typically, the bioactive components are extracts of plants, herbs and botanicals, vitamins, bioactive substances such as topically active therapeutic agents, i.e., steroids, enzymes, antibiotic agents, liposome systems, etc.

Particularly preferred bioactive components of the compositions of the instant invention are vitamin and co-enzyme biocomplexes, most preferably containing a combination of water-soluble vitamins, oil-soluble vitamins and coenzymes. Other preferred bioactive components include steroid-catecholamine biocomplexes, protein-peptide biocomplexes, amino acid derivative biocomplexes, intracellular transmitter biocomplexes, and intracellular second degree messengers biocomplexes. Depending upon the particular pathology to be treated, numerous biocomplexes can be formulated within the teachings of the present invention.

The biocomplex compositions of the instant invention can be utilized in a variety of therapeutic and cosmetic applications, and by normalizing specific cell metabolism, can stabilize extracellular matrix of skin, restore lipid membranes in the intercellular space of the horny layer, improve cutaneous elasticity, and increase oxygen utilization in the skin. Depending upon the particular components of the composition, the biocomplexes can also have anti-free radical effects, antioxidant effects, increase amino acid synthesis and aid in epidermal restructuring and skin regeneration. Use of these compositions containing the bioactive agents to maintain normal cell metabolism for extended periods of time also prevents premature aging of the skin, normalizes sebaceous gland production, normalizes lipid, carbohydrate and oxygen metabolism of the skin cells and revitalizes and provides anti-wrinkle benefits.

Similarly, when utilized in treatment of various other pathologies, the compositions of the present invention provide a superior therapeutic method when compared to standard agents typically utilized for this purpose. For example, when used to treat patients suffering from the effects of trauma an hemorrhagic shock, the compositions of the instant invention were found to be superior to conventional therapeutic methods.

Typical compositions of the instant invention which include steroid-catecholamine biocomplexes utilizable in the therapeutic methods of the present invention typically comprise hydrocortisone (cortisol, preferably water-soluble and balanced with HPBC); corticosterone-21-sulfate (preferably as the potassium salt); progesterone (preferably water-soluble and balanced with HPBC); β-Estradiol, (preferably water-soluble and balanced with HPBC); estriol-3-sulfate sodium salt; cholecalciferol sulfate (Vitamin D3 sulfate); epinephrine hydrochloride (adrenalin); arterenol hydrochloride (Noradrenalin); and aldosterone.

Typical compositions of the present invention which include protein-peptide biocomplexes which are utilizable in the therapeutic methods of the present invention typically comprise adrenocorticotropic hormone (ACTH, fragment 1-24); β-lipotropin, β-Endorphin (fragment 61-91); somatotropin (HGH, from human pituitary); follicle-stimulating hormone (FSH, from human pituitary); luteinizing Hormone (LH, from human pituitary); thyrotropic Hormone (TSM, from human pituitary); vasopressin (arginine vasopressin); parathyroid hormone (fragment 1-36); thyrocalcitonin (calcitonin, from salmon); angiotensin II (human); glucagon (mixture of bovine & porcine); vasoactive Intestinal Peptide (VIP); gastric inhibitory polypeptide (GIP, human); and insulin (human).

Typical prostaglandin biocomplexes for use in the compositions of the instant invention comprise prostaglandin $D_2$, prostaglandin $E_1$, prostaglandin $E_2$, prostaglandin $F_{2\alpha}$ and prostaglandin $I_2$.

Typical intracellular transmitter biocomplexes for use in the compositions of the present invention comprise mixtures of adenosine-5-triphosphate (as the calcium salt, ATP, water-soluble); Guanosine-5-triphosphate Lithium Salt (GTP); Phosphoinositedes Sodium Salt (Purified from Bovine Brain containing: a) 15–20% phosphotidyl inositol 4,5-diphosphate and phosphatidylinositol 4-monophosphate; b) the remainder is a mixture of phosphatidylinositol and phosphotidylserine); brain extract (Type I, containing: a) 10–20% phosphatidylinosilides and 50–60% phosphatidylserines as well as several other brain lipids); adenosine 3'5'-cyclic monophosphate Sodium Salt (3'5'-AMP); guanosine 3'5'-cyclic monophosphate Sodium Salt (3'5'-GMP); d-myo-Inositol triphosphate potassium salt ($IP_3$, from Bovine brain containing two isomers: ~80–90% 1,4,5-isomer with primary 2,4,5 isomer and <0,05 mol. a. per mole inositol 1,4,5-triph.); and phosphodiesterase 3'5'-cyclic nucleotide activator (Calmodulin); protein kinase; coenzyme A; β-nicotinamide adenine dinucleotide (β-NAD); β-nicotinamide adenine dinucleotide phosphate (β-NADP).

In a preferred embodiment of the instant invention, the bioactive agents of the protein-peptide biocomplex comprise by weight per 1 kg of formulated product:

2–120 ng adrenocorticotropic hormone (ACTH, fragment 1-24);

1–10 μg β-lipotropin β-endorphin (fragment 61–91);

1–10 μg somatotropin (HGH, from human pituitary);

0.01–1 μg follicle-stimulating hormone (FSH, from human pituitary);

0.05–0.5 μg luteinizing hormone (LH, from human pituitary);

0.05–0.15 µg thyrotropic hormone (TSM, from human pituitary);

0.020–1.0 µg vasopressin (arginine vasopressin);

0.5–2.0 µg parathyroid hormone (fragment 1–36);

20–120 ng vasoactive intestinal peptide (VIP); and 0.1–5 µg insulin (human).

In a preferred embodiment of the present invention, the bioactive agents of the steroid-catecholamine biocomplex comprise by weight per 1 kg of formulated product 25–250 µg hydrocortisone;

1–30 µg corticosterone-21-sulfate;

2–10 µg progesterone;

50–500 ng β-estradiol;

100–400 ng estriol-3-sulfate sodium salt;

200–700 ng epinephrine hydrochloride;

300–900 ng arterenol hydrochloride; and

10–600 ng α-aldosterone-21-hemisuccinate.

In a preferred embodiment of the present invention, bioactive agents of the intracellular transmitters biocomplex comprise by weight per 1 kg of formulated product:

1–50 mg adenosine-5-triphosphate (ATP);

1–30 mg guanosine-5-triphosphate (GTP);

10–100 µg phosphoinositedes containing: a) 15–20% phosphotidyl inositol 4,5-diphosphate and phosphatidylinositol 4-monophosphate; b) the remainder is a mixture of phosphatidylinositol and phosphotidylserine);

0.5–10 mg brain extract (Type I, containing: a) 10–20% phosphatidylinosilides and 50–60% phosphatidylserines as well as several other brain lipids);

1–10 mg adenosine 3'5'-cyclic monophosphate sodium salt (3'5'-AMP);

0.1–5 mg guanosine 3'5'-cyclic monophosphate (3'5'-GMP);

1–6 µg d-myo-Inositol triphosphate $IP_3$, from bovine brain containing two isomers: ~80–90% 1,4,5-isomer with primary 2,4,5 isomer and <0,05 mol. a. per mole inositol 1,4,5-triph.);

0.01–0.25 mg protein kinase;

0.2–2.0 mg coenzyme A;

5–35 mg β-nicotinamide adenine dinucleiotide sodium salt (β-NAD);

1–25 mg β-nicotinamide adenine dinucleotide phosphate (β-NADP); and

1–20 µg phosphodiesterase 3'5'-cyclic nucleotide activator (calmodulin).

In a preferred embodiment of the present invention, bioactive agents of the prostaglandin biocomplex comprise by weight per 1 kg of formulated product:

1–5 µg prostaglandin $D_2$,

1–5 µg prostaglandin $E_1$,

1–5 µg prostaglandin $E_2$, 0.5–3 µg prostaglandin $F_{2\alpha}$ and

1–5 µg prostaglandin $I_2$.

The novel delivery system of the present invention may be of two variations, one of which acts as a substitute cell membrane (SCM) and the other of which is referred to herein as an unloaded delivery complex (UDC), depending upon whether or not the delivery system has incorporated the desired biocomplexes of the instant invention. Both of these types of delivery systems utilize an aqueous media in combination with a lipid component, a carbohydrate component and a protein component.

The novel delivery system of the present invention thus comprises:

50–95% by weight of an aqueous media in combination with 1.5–25% by weight of a lipid component;

0.2–10% by weight of a carbohydrate component; and 0.01–15% by weight of a protein component.

The aqueous media of the delivery system of the present invention preferably comprises distilled water in combination with pharmaceutical and/or cosmetic grade stabilizers, cryoprotectants, bile acids, protease inhibitors, protein stabilizers, antioxidants, and preservatives. Depending upon the particular use of the delivery system, these adjuvants are added to the distilled water in minor amounts to perform their designated purposes.

The lipid component of the delivery system of the instant invention is preferably comprised of a mixture of saturated fatty acids, triacylglycerols with saturated and/or unsaturated fatty acids, natural and/or modified phospholipids, sphingolipids, glycosphingolipids and sterols. The percentage composition of each of these types of lipids will vary according to the particular usage of the delivery system. Preferably, in the substitute cell membrane delivery system, the lipid component will consist of about 0.5–2% by weight saturated fatty acids; 0.1–1% by weight triglycerides with saturated fatty acids; 75–95% by weight natural and/or modified phospholipids; 0.1–6% by weight sphingolipids, 0.01–5% glycolipids; and 0.1–4% by weight of sterols.

The carbohydrate component utilized in the substitute cell membrane variation of the delivery system of the instant invention is preferably comprised of a mixture of glycosoaminoglycans, glycoproteins and attachment matrix forming carbohydrates. Preferably, the carbohydrate component is from about 60–801 by weight of one or more attachment matrix forming carbohydrates; 20–40% by weight of one or more glycosoaminoglycans; and 0.01–7% by weight of one or more glycoproteins. Preferred attachment matrix forming carbohydrates are those such as gelatin, poly-D-lysine, protamine and DEAE-dextran. Preferred glycosoaminoglycans are those such as heparin sodium salt, chondroitin sulfate A, chondroitin sulfate B, chondroitin sulfate C and hyaluronic acid. The glycoprotein is typically glycoprotein, al-acid (orosomucoid acid).

The protein component of either variation of the delivery system of the instant invention will likewise be composed of a mixture of one or more structural proteins, extracellular matrix proteins and cytoskeleton proteins.

Preferred proteins for use in the present invention include elastin; collagen, both acid soluble and water soluble; and hydrolastin (hydrolyzed elastin). In the substitute cell membrane variation of the delivery system of the present invention, most preferably, the protein component is at least 35–45% by weight of a collagen and at least 35–55% by weight of hydrolyzed elastin.

The compositions of the instant invention which are formulated in the substitute cell membrane variation of the delivery system of the instant invention are prepared by first mixing together the components of the aqueous media with the lipid, carbohydrate and protein components using a magnetic stirrer or other suitable homogenizer, and then utilizing a homogenizing-type device to form a microemulsion of these components with the bioactive complexes wherein the size of the resultant particles of the microemulsion are of the order of 60–150 nm. This mixture is then stored for an incubation period, with low speed stirring. This is followed by centrifugation to fractionate the various particle sizes. Removal of the supernatant results in the formation of a membrane-like substance from the supernatant which contains the desired bioactive agents. This composition can be utilized directly in the treatment of patients, or can be lyophilized for an indefinite period of storage before reconstitution and use. Further specific details are described below in the "Basic Steps of Biocomplexes Preparation with and without Substitute Cell Membrane".

In the process for the preparation of the compositions of the invention in the substitute cell membrane variation delivery system, the homogenization is typically accomplished by a high shear homogenizer at about 5000–10000 rpm, but can also be achieved utilizing similar devices which achieve micron-sized subdivision of the particles. Typically, the incubation period of the process is about 40° C., but this is dependent upon the stability of the bioactive ingredients, and can be adjusted in accordance therewith. Typical incubation times to achieve uniform particle size are in the range of 30 minutes to 3 or 4 hours, and most preferably range from 1–3 hours, but these are likewise dependent upon the particular bioactive agent utilized and the particular lipid, carbohydrate and protein components used in the formulation of the composition.

Typical centrifugation parameters are in the range of 1500–2000 g for periods of about 30 minutes to about 6 hours.

In an alternate embodiment of the present invention, the substitute cell membrane can be prepared as an unloaded delivery complex no active agents or with only some of the active ingredients incorporated therein. In the unloaded delivery complex variation of the compositions of the present invention, the aqueous media is added to the lipid, carbohydrate and protein components, and these are homogenized to form a uniform mixture. In such instances, the pH of the unloaded delivery complex is adjusted so as to be 3–4 pH units lower that the pH of the bioactive agents which are to be later incorporated. For example, if the pH of the bioactive agents is about 7, then the unloaded delivery complex is prepared with a pH of about 4. At a subsequent time, the thus-formed substitute cell membrane can be re-hydrated, and the bioactive agents, or additional bioactive agents added thereto. This allows large quantity preparation of the substitutecell membrane delivery system, with later incorporation of the particular desired bioactive agents. This method is suitable only in the instance where three or fewer bioactive agents are being added to the substitute cell membrane delivery system.

BASIC STEPS OF BIOCOMPLEXES PREPARATION WITH AND WITHOUT SUBSTITUTE CELL MEMBRANE:

Step 1 Biocomplexes preparation
Step 2 Substitute cell membrane preparation
Step 3 Incorporation of the biocomplexes into the substitute cell membrane
Step 4 Centrifugation
Step 5 Freeze-drying procedure
Step 6 Fine grinding procedure Step 1: Biocomplexes Preparation Each biocomplex consists of specific media/medias and specific active agents.

1.1 Media Preparation

Specific media must be prepared for particular active substances composition. It is possible to have multiple parts in the final biocomplex. When this is the case, it is necessary to prepare appropriate specific media for each part of the active ingredient composition, (for details, see specific biocomplex formulation).

Take all media components and dissolve in distilled water/buffer by mixing on a magnetic stirrer or on a homogenizer.

1.2 Active Substance Composition Preparation

Weigh all active ingredients

Dissolve/disperse each active ingredient in appropriate media by mixing on a homogenizer with Ultra-Turrax type of adapter. In some instances, it is necessary to predissolve the active ingredient in a specific solvent (see examples below).

If there are separate parts of the active substances composition in the final biocomplex, prepare each part separately.

1.3 Mixing of the Active Substances Composition

This specific step is necessary if there are multiple parts containing separate active substances composition in final biocomplex. Add/mix all parts with each other (specific order of adding, see in appropriate formulation) by mixing on a magnetic stirrer/homogenizer.

1.4 Biocomplex Creation

The final biocomplex is created by mixing/homogenizing of the active substances composition with the media on Ultra-Turrax type of homogenizer. Specific regimen of homogenization (time, speed-RPM, vacuum) varies according to the specific components in each biocomplex formulation.

1.5 Biocomplex Storage

Before the biocomplex is formulated into the delivery system or freeze-dried, it is necessary to store the biocomplex in a cool place (refrigerator) for a holding period.

Step 2: Substitute Cell Membrane Preparation (SCM)

Substitute cell membrane consists of media and active ingredients (lipid, carbohydrate and protein components).

2.1 Media Preparation

Weigh all media components and dissolve in distilled water by mixing on a magnetic stirrer or on a homogenizer.

2.2 SCM Components Preparation

Weigh all active ingredients for the SCM. If it is necessary, predissolve appropriate compounds in specific solvent (see specific formulation of SCM).

2.3 Final Preparation of SCM

Mix all the SCM components, step-by-step, into the media by mixing with Ultra Turrax type of homogenizer. Adjust pH of SCM to appropriate level (see specific formulation of SCM). Continue mixing (after last component has been added) on a homogenizer not more than 15–25 minutes. Specific times vary according to the particular formulation.

Step 3: Incorporation of Biocomplex into SCM

Slowly add biocomplex into SCM by mixing on a homogenizer. Adjust pH to an appropriate level. Continue mixing on ultra-Turrax type of homogenizer. Specific times, rotation per minutes, vacuums and temperatures will vary according to the specific formulation.

Step 4: Centrifugation

Centrifuge SCM-incorporated biocomplex. Specific times, gravities and temperatures of centrifuge will vary according to the specific formulation.

Step 5: Freeze-Drying Procedure

Freeze-dry final product.

Step 6: Fine Grinding Procedure

Grind freeze-dry powder to particle size specifically indicated in formulation.

The effectiveness of various types of specific biocomplexes has been evaluated both for intravenous infusion and topical applications.

Scientific research for evaluation of the compositions containing bioactive complexes of the present invention was performed extensively and reflected the functional condition of the main regulatory system of the organism and cell metabolism.

The study included the following systems:

first degree messengers, more than 50 different types of proteins, lipids, steroids and other biologically active substances were simultaneously studied;

second degree messengers, intracellular transmitters, and different types of prostaglandins;

cell membrane and cytosol receptors;

cardiovascular circulation, which includes the systemic, peripheral, cerebral and myocardial circulation (over 80 different parameters).

This research was focused on two varying types of formulations. The first type of formulation was prepared afor intravenous injection of specific compositions of bioactive agents (especially created for critical conditions, as described in Example 12) during the post-trauma reaction of an organism. The second type of formulation was prepared for topical application of various types of compositions of bioactive complexes with specific effects such as activation and/or depression of specific cellular function.

The results of these experiments and the details of the materials, methods and results are described below.

TESTING OF PARENTERAL FORMULATIONS

Materials and Methods

The experimental technique was developed using 20 dogs. Then the primary experiments were conducted. After the third experiment, the results were statistically processed in order to check the validity of the data obtained. If the obtained results were statistically valid, the series was considered completed. This approach to the experiments is caused by high cost of reagents used for the analyses.

The experiments were conducted on male mongrel dogs having a mass of 19–25 kg. All the experiments were carried out under local anesthesia.

After administration of a depolarizing relaxant—succinylcholine (diacetylcholine, eistenon), introduced intravenously with a dose of 0.8+1.0 mg per kilogram of mass, endotracheal intubation was conducted. Artificial pulmonary ventilation (APV) was performed with the aid of the respirators PO-6-03. The adequacy of APV was controlled by means of arterial blood pH, venous blood pH, hemoglobin saturation with oxygen ($SaO_2$ of arteria) and by cerebral circulation parameters.

In each case, traumatization was made 60 minutes later after a dog was switched to APV (giving the experimental animal time to adapt both to APV and to the nonphysiological position on the operating table with all the above-mentioned parameters being under control. Then, various types of trauma were performed, e.g., experimental hemorrhagic shock or experimental traumatization. The aggression continued until arterial pressure was lowered by 30–50% compared to its background value down to 70–80 Torr. This method of traumatization has a number of advantages over a trauma inflicted by the standard method, since it makes it possible to control the process in order to reach a certain extreme state by varying the dose of traumatic action.

After one hour of traumatization, treatment of the animals is begun. For this purpose, two groups of treatment procedures were developed.

Standard Treatment Procedure (Control Group)

This procedure included complex therapy with most advanced drugs using in shock conditions. Complex treatment included transfusion therapy with high and low molecular weight dextrans, various types of steroids—gluco- and mineralo-corticosteroids, vasoconstrictors, anabolitic hormones, metabolizers, etc., active drugs.

Treatment Procedure Using Compositions Containing Bioactive Agents

This procedure included only transfusion therapy with specific compositions containing bioactive agents created especially for shock pathology, as described in Example 12.

A. Methods of First Degree and Second Degree Messengers Study

The content of hormones and biologically active substance (first and second degree messengers) in the blood of experimental animals was estimated according to the following scheme: the background level, the initial level (an hour later after APV started), 5 minutes after traumatization is finished, and then every hour until the end of the experiment.

All the hormones and biologically active substances in blood were examined by the radioimmunological analysis (RIA) which is characterized by a high specificity, high sensibility and precision. Radiometry of the samples was evaluated on fully automated installations for radiochemical analysis "Beta-1", "Beta-2", "Gamma-1", and "Gamma-12". These installations are provided with an applications package to make all the necessary calculations of the RIA data both in the on-line and off-line regimes. The names of hormones are given in accordance with the nomenclature recommended by the International Biological Union.

Using corresponding commercial kits, the following hormones have been determined:

1. Adrenocorticoid hormone (ACTH, corticotropin) was determined using the commercial kit ACTHK-PR (CIS International, France) and JNC-2400 (Immuno-Nuckar Corporation, USA);
2. Vasopressin (ADH) was determined using the kits Vasopressin RIA (Buhlman Labor, Switzerland);
3. Lutropin (luteinizing hormone, LH) was determined by means of the kits LH-PR (CIS, France) and RS-4124 (Radioassay System Labor, USA);
4. Follitropin (follicle stimulating hormone FSH) was determined by using the kits FSHK-PR (CIS, France) and RS 4123 (Radioassay System Labor, USA);
5. Somatotropin (STH) was determined by using the kits HgHK (CIS, France) and CNR-722 (Cambridge Medical Diagnostics, USA);
6. Hydrocortisone (hydrocortisone 11, 17, 21, trihydro, 4 pregnen, 3,20-dion) was determined by the commercial kits Cortk-125 (CIS, France) and ING-13170 (Immunonuclear Corporation, USA);
7. Aldoeterone (11,21-dihydroxy-4 prynal—18 al—11 hemiacetat) was determined by mens of the kits SB-ALDO (CIS, France) and AS-888 (Wien Laboratories, USA);
8. Cyclic adenosine monophosphate (c-AMP, 3'5'-AMP) was determined using the commercial kits TRK-425 (Amersham, England);

9. Cyclic guanosine monophosphate (c-GMP; 3'5'-GMP) was determined by means of the kits TRK-500 (Amersham, England);
10. Renin-angiotensin system was estimated through determining the activity of plasma renin (APR) using the kits RENK (CIS, France);
11. Prostaglandin A(PGA) was determined using the kits CA-501 (Clinical Assay, USA);
12. Prostaglandin E was examined using the kits CA-501 (Clinical Assay, USA) and SG-6001 (Seragen, USA);
13. Prostaglandin $F_{2\alpha}$ was determined by means of the kits CA-503 (Clinical Assay, USA) and SG-6002 (Seragen, USA).

B. Methods of Membrane and Cytosol Receptors Study

All membrane and cytosol receptors were evaluated using various types of radioisotope ligand techniques. Using corresponding isotope ligand, the following receptors activity/amount have been determined:

membrane type of receptors: $\beta_1$ and $\beta_2$—adrenoreceptors, $\alpha_1$ and $\alpha_2$ adrenoreceptors, angiotensin II receptors, prostaglandin $E_2$ receptors, prostaglandin $F_{2\alpha}$ receptors;

cytosol type of receptors: glucocorticosteroid receptors, mineralo-corticosteroid receptors, estrogen receptors, androgen receptors.

C. Methods of Blood Circulation (Hemodynamic) Examination

For complex studies of blood circulation the computer system D3-28 as well as CM1803 were used. An algorithm and application package for automatic processing of over 80 parameters of blood circulation both in the on-line and off-line systems was developed. Monitoring systems accomplished permanent control over most of the circulating parameters, and every 30 minutes documentary records of all the indices under study were carried out.

a) Central (systemic) hemodynamic (CH). The following CH indices were examined: (1) arterial pressure (AP) was studied by the invasive method; (2) cardiac stroke volume (CSV) was studied by the rheographic method using the rheograph P4-02; (93) heart rate (HR); (4) minute blood volume (MBV); (5) peripheral resistance (PR); (6) blood volume (BV)—by the method of diluting serum albumin, labeled by $^{131}$I. The measurements were made on the autoanalyzer "volumetron" (ANS-731); (7) hematocrit number (Ht); (8) central venous pressure (CVP).

(b) Contractile function of the myocardium was studied by the most common method in electromechanocardiography-phase analysis of ventricular systole. For this purpose polycardiographic record (PCR) was made consisting of electrocardiogram, phonocardiogram and rheogram of the aorta. The analysis of ventricular systole phases was conducted by K. Blumberg's method in V. L. Carpman's modification (3), taking into account variations of their deciphering. From the PCR indices were calculated: (1) phase duration of asynchronous contraction (AC); (2) phase duration of isometric contraction (IC); ;(3) duration of expulsion period (E); (4) duration of tension period (T); (5) duration of common systole ($S_c$); (6) duration of electrical systole ($S_e$); (7) duration of diastole (D); (8) myocard tension index (MTI); (9) Blumberg-Muller mechanical coefficient (BMC); (10) intrasystolic index (ISI); (11) time of expulsion of the minute blood volume (TMBV); (12) rate of the left ventricle evacuation ($V_e$); (13) duration of the mechanical systole ($S_m$).

(c) Cerebral circulation was studied by the rheoencephalography (REG). To this aim, needle electrodes were introduced hypodermically in bitemporal lead providing net blood flow of the cerebral cortex and subcortex. The REG data were measured by the four-channel rheograph P4-02 in channel at a frequency of 120 kHz. The differential REG was recorded simultaneously with the volumetric curve.

The following parameters were studied: 1. cerebral circulation index (C/CI); 2. volumetric rate of cerebral circulation (VRC); 3. volumetric pulse ration (PR%); 4. amplitude rate index (ARI); 5. filling rate of "great vessels of the organ (region) investigated—$V_{rapid}$; 6. filling rate of small vessels—$V_{slow}$; 7. tension of great vessels of the organ (region) investigate—$t_{gr}$; 8. small vessels tension—$t_{sm}$; 9. total vascular tension of the organ (region) studied—$V_{tot}$; 10. pulse wave transmission of time along the section heart-organ studied (PVTT).

d) Peripheral circulation was studied by the rheovasographical method (RVG) by means of introducing needle electrodes into the distal girdle of the hind (pelvic) limb: one at the level of distal girdle of tarsal bones, the other in the mnetarsal region. The RVG data were measured by the 4-channel rheograph P4-02 with synchronous record of the volumietric and differential curve. The quantitative analysis of RVG was carried out similarly to the REG calculating method.

e) In addition to noninvaive methods of myocardium and peripheral circulation functions evaluation, invasion method of catheterization of the various vessels was also used:

myocardium catheterization—specific catheters for catheterization of the left and right ventricles were used. Those catheters allowed monitoring of important physiologicalinformation in those ventricles and provided more detailed information about the functional condition of the myocardium;

peripheral vessels catheterization—allowed monitoring of important information directly from vessels;

f) Microcirculation was evaluated by a method developed by Dr. Kalantorov based on radioisotope detection after subcutaneous injection of low dosage of radioisotopes, such as $TC^{99}$ or $I^{131}$.

Standard statistical data processing was accomplished on the computers DS-28 and CM 1803-04. To estimate the validity of each parameter, deviation from the initial (100%) level as a whole in each phase (p phases) was determined. It was calculated as a product of probabilities (P) of individual points differences in this phase since each point is an independent measurement. Changes in phases at $p<0.05$ were considered valid.

Time—Invariant Methods of Posttraumatic Changes Estimations (Time Normalization Method)

An important methodical problem which is associated with a great number of controversial results in literature concerning shock and extreme is due to the individual peculiarities of each organism, even in the case of inflicting ideally standardized trauma (which is rather problematic per se). It is inevitable that the reciprocal response of the organism to trauma and the lifetime of experimental animals is different. To overcome these differences, changes of a number of indices characterizing functions of the organism (including blood circulation) in shock are made in different intervals from the start of the process. In this case within each interval average indices are calculated on the basis of values, taken from animals (or people) at various levels of the process. It should be emphasized that the number of long-term experiments decreases progressively, reducing usefulness of the information used for deriving average values. In the scientific literature, comparison is fairy often made of indices of various organism functions recorded at the same time intervals from the start of the process without taking into account the fact that in experimental animals this process can proceed at different rates, hence one group can incorporate indices recorded at different phases of the process and each of them has an inherent mechanism of development with specific external manifestations. To a large extent, it is due to the fact that a sufficient number of important parameters both in the experiment and in clinic are determined discretely rather than permanently. Just that is why the analysis of changes in parameters characterizing these or those functions in a pathologic process should be conducted not only allowing for astronomical time elapsed since the start of the process or after pathogenic stimulation, but rather in its dynamics considering the severity of the general condition.

Estimation of indices in the course of permanently developing process at equal intervals has an additional disadvantage. In this case, the sharpest shifts of the indices under study may appear not recorded at all, while in the monotonous course excess information is obtained.

Therefore, in order to be able to compare the results of single experiments (in which lifetime of the experimental animals fluctuates noticeably) as well as to increase validity and substantiation of the conclusions, we have divided each experiment into periods of time as follows.

The time count of the experiment started five minutes after trauma infliction ceased. The end of time count of the experiment was the moment of ceasing cardiac activity of the experimental animal (in the group of dead animals).

For each animal, an individual dimensionless coefficient K was calculated: $K = t_{max}/t_i$, where $t_{max}$ is the time of the most prolonged experiment in this series. In our case $t_{max} = 6$ hours, 30 minutes. $t_i$ is the duration of the present experiment. (The lifetime of ten experimental animals in the group of dead animals varied from 1 hour, 20 minutes to 6 hours, 50 minutes.)

In each case, the measurement period of all the studied parameters was multiplied by this individual coefficient. Thus, in this way, each experiment was normalized. It is evident that in this case absolute time of measurement of this or that reading lost all meaning, and in all the diagrams and in discussions such normalized time of the whole experiment was taken as 100%. and hence each moment of time was also expressed on percentage basis.

This enabled the plotting of diagrams averaged over all the experiments. They reflected changes in all the measured parameters depending on time.

The majority of the parameters investigated have allowed us to identify three phases of the process for the parameters of the central hemodynamics, cerebral and peripheral blood flows, phase analysis of the cardia cycle and hormonal shifts.

Phase duration was (in % of all the experimental time): $t_1 = 28.4\%$ (0–28.4); $t_2 = 40.7\%$ (28.4–69.1); $t_3 = 30.99\%$ (69.1–100).

In view of the differences in phase duration, we calculated relative rate of changes in all the studied parameters of circulation and hormone content in each phase, since changes in any parameter by one and the same value (in different phases) can proceed at different rates.

This time normalization is substantiated if one takes into account some aspects of tanatogenesis. Any pathological factor or any aggression causes reciprocal response of the organism at all levels: from a cell to general systems of the function of the organism. If the catabolic phase of the postaggressive reaction is harmonious and adequate and function autoregulation is preserved, the action of a damaging factor does not result in the terminal state. However, too severe or too prolonged aggression, imperfect reactivity of the organism cause a harmonious and inadequate postaggressive reaction. In this case, if any function is depleted, others are disturbed inevitably and the total postaggressive reaction turns form a defense reaction into decompensated one, pathogenesis becomes tanatogenesis. At this stage of pathology, specificity of an aggression factor is not critical. Since the moment when an inharmonious general postaggressive reaction becomes lethal for the organism, the tanatogenesis mechanisms are similar in all the terminal states, but in different individuals they can proceed at different rates.

The "human organism is not a polyglot" as to its basic pathophysiological mechanisms. There exists a general reciprocal reaction qualitatively of the same type at any kind of a conflict between the human organism and its environment. The time normalization of the experiment has been suggested to level different rates of the process proceeding in different individuals .

This nonuniformity of developing of shock in connection with compensation mechanism and correlation between damage extent and adaptive reaction manifestation has been described in the scientific literature.

Division of the postaggressive reaction of the organism into separate phases makes it possible to consider disturbances of many circulation parameters by stages as well as a reciprocal reaction of the endocrine system in tanatogenes is.

Compareison data of using specific compositions of bioactive agents created for shock pathology, whose preparation is described in Example 12, and standard treatment procedure during post-trauma reaction of the test animals is shown in FIGS. 4–17. These figures demonstrate the effectiveness of the compositions of the present invention as a treatment procedure in comparison with standard (control) treatment procedure currently available in the pharmaceutical industry.

Using the standard treatment procedure, the test animals had a mortality rate equal to 85–90%. However, in the treatment procedure which utilized a composition of the present invention created for shock pathology, mortality levels were reduced to 27–32%.

By observing the FIGS. 4–17, one observes improvement not only in blood circulation parameters, but also stabilization and adequate adaptation of first degree messengers as well as second degree messengers in comparison with the standard treatment procedure.

TESTING OF TOPICAL FORMULATIONS

Using specific compositions for topical application containing bioactive agents according to the present invention, the individualized reaction of cellular metabolism can be observed.

The investigation of a topical application of the various types of biocomplexes was carried out in vivo on 10, 15 and 20 kg male and female dogs. All experiments were carried out under anesthesia as described hereinabove.

The hair of the dorsal skin was cut but not shaven. The biocomplexes were spread on the skin at a rate of 5 ml per 150 cm$^2$, and were tested by comparison with controls containing only vehicle. Tissue samples (8–10 mm stamp biopsies) were removed every thirty minutes during a five hour experimental period. Tissue samples were immediately shock-frozen in liquid nitrogen. Later, they were homogenized in polytron-type homogenizer and appropriate extraction procedures performed to evaluate the specific receptor's activity.

All membrane and cytosol receptors were evaluated using various types of radioisotopic ligand techniques as described hereinabove.

Microcirculation was examined using rheovasographic method (RCG) as well as by radioisotopic detection techniques described hereinabove.

The results from the topical testing of the various biocomplexes are graphically depicted in FIGS. 18–30. In these figures, Roman numerals (I, II, III) refer to the phase of the test process. Many intracellular active substances evaluated during this testing change their activity by phase. The horizontal axis shows the passage of time of the experiment, which is standardized to 100. The vertical axis shows the concentration of bioactive substances under evaluation. In all testing, 100% is equivalent to the normal concentration of the particular bioactive substance in a healthy functioning organism. These results demonstrate the specific effects of biocomplexes when applied topically to increase and/or decrease specific functions which are necessary to achieve the desired therapeutic and/or cosmetic results.

The utility of the bioactive complexes of the instant invention for topical application was determined by clinical testing conducted at the Institute of Experimental Morphology Academy of Science and Scientific Research Institute of Dermatology of the Georgian Ministry of Health. Twenty-five different skin diseases were studied, using a total of 3061 enrolled patients. All studies were conducted in double-blind fashion. The control group utilized 482 patients receiving conventional treatment for the particular disease under study. At the end of two Jears, the data was analyzed to confirm the differences in the patient populations.

Patients with Oily and Very Oily Skin

Utilizing the compositions described in Examples 4 and 5, respectively, oily and very oily skin were found to revert to normal, due to a decrease in the production of skin oil. In 87!k of the cases with oily skin, gland production was normalized in 1–3 months. In 91% of the cases with very oily skin, there was a significant reduction in oil production, with a reduction to oily skin within 1.5–3.5 months. Within a further 2–4 months, 63% of these patients experienced a normalization of sebaceous gland production.

Patients with Dry and Very Dry Skin

Utilizing the compositions described in Examples 2 and 3 respectively, patients with dry and very dry skin experienced an increase in sebaceous gland production until it reached a normal state. In 92% of the cases with dry skin, normalization occurred with 20–60 days. In 97% of cases with very dry skin, a significant increase of oil production was observed in 15–30 days, with complete normalization of sebaceous gland function observed within an additional 1.5–3.5 months.

Patients with Normal Skin

Utilizing the formulation described in Example 1, normal skin treated maintained a normal skin metabolism and experienced a lack of premature aging.

Cellulite

In 86% of cases with cellulite, the patients observed a substantial decrease of lumpy fat in the thighs, hips and buttock areas. Elasticity, tone and contraction of the skin in the cellulite areas increased in a remarkable manner when compositions of Examples 7, 15 and 17were used simultaneously.

Total Patient Popoulation 87% of the patient population reported a reduction in the size and appearance of wrinkles.

Skin Diseases

In patients with a recognized skin disease, efficacy was reported as follows: acne—82% (using composition of Example 9); neurodermatitis—79% (using composition of Example 11); eczematous—75% (using composition of Example 11); psoriasis—76% (using composition of Example 10); and itches of the skin—83% (using composition of Example 11).

Hair and Scalp Diseases

In patients with a recognized hair and scalp disease, efficacy was reported as follows: alopecia—80%; and seborrhea—86% using the compositions of Examples 6, 16 and 17 simultaneously.

EXAMPLES

EXAMPLES OF DELIVERY SYSTEM (SCM)

Example A

| Delivery System (Substitute Cell Membrane) Version 1 | |
|---|---|
| Ingredient | Amount 1/kg Cream |
| Aqueous Media Consisting of: | |
| Distilled Water (Frozen Thawed) | 20 ml |
| EDTA-Na$_2$ | 0.01 g |
| Molybdic Acid Sodium Salt | 0.066 g |
| Dithiothreitol | 0.0016 g |
| D-Trehalose | 0.1 g |
| Sucrose | 0.305 g |
| D-Sorbitol | 1.650 g |
| Aprotinin; | 1300 KIU |
| Activity: 10,000 KIU/ml Solution | 0.13 ml (0.000.22 g) |
| Glutation | 0.04 Ig |
| L-Ascorbic Acid; 20–200 Mesh | 0.075 g |
| Prionex; | 0.025 ml |
| (10% Solids in Solution) | |
| Albumin, Bovine (BSA) | 0.025 g |
| Ammonium Sulfate | 0.26 g |
| Potassium Chloride | 0.05 g |
| Polyethylenglycol 200 | 2 ml |
| Germaben IIE | 0.06 ml |
| Lipid Component: | |
| Nonadecanoic Acid Methyl Ester | 6 mg |
| Arachidic Acid | 6 mg |
| Heneicosanoic Acid Methyl Ester | 4 mg |
| Behenic Acid | 1 mg |
| Tristearin | 1 mg |
| Triarachidin | 2 mg |
| h-SPC (Hydrogenated Soy Phosphatidylcholine-99% or Hydrogenated Egg Phosphatidylcholine-99%) | 250 mg |
| Soy PC (Soy Phosphatidylcholine-90%) | 500 mg |
| PE (L-a Phosphatidylethanolamine-Type IIS) Containing: Phospholipids- and glycolipids | 15 mg |
| PS Brain Extract, Type III: (L-a Phosphatidylserine) | 1 mg |
| PI Phosphatidylinositol; Crude, from Soybean Containing: PE and Phosph. Acid | 2 mg |
| DMPC (Dimuristoyl Phosphatidylcholine-C: 14) | 10 mg |
| DMPG (Dimuristoyl Phosphatidyl-glycerol-C: 14) | 4 mg |
| DPPC (Dimalmitoyl Phosphatidyl-choline-C: 16) | 15 mg |
| DPPG (Dipalmitoyl Phosphatidyl-glycerol-C: 16) | 6.5 mg |
| DSPC (Distearoyl Phosphatidyl-choline-C: 18) | 12 mg |
| DSPG (Distearoyl Phosphatidyl-glycerol-C: 18) | 5 mg |

Delivery System (Substitute Cell Membrane) Version 1

| Ingredient | Amount 1/kg Cream |
|---|---|
| DMPE (Dimuristoyl Phosphatidyl-ethanolamine-C: 14) | 2.5 mg |
| DSPE (Distearoyl Phosphatidyl-ethanolamine-C: 18) | 4 mg |
| DPPE (Dipalmytoyl Phosphatidyl-ethanolamine-C: 16) | 3 mg |
| Maleic Acid Hydrazide | 50 mg |
| Brain Extract, Type VIII; (from Bovine Brain - 30% Sphingolipids; 30% Cerebroside; 10% Sulfated) | 15 mg |
| Cerebrosides (Ceramide Galactosides) | 0.8 mg |
| Cholesterol | 15 mg |
| Ergosterol (Provitamin D2) | 10 mg |
| Carbohydrate Component: | |
| Heparin Sodium Salt | 10 mg |
| Chondriotin Sulfate A | 50 mg |
| Chondriotin Sulfate B (Dermatan Sulfate) | 0.25 mg |
| Chondroitin Sulfate C | 10 mg |
| Hyaluronic Acid | 15 mg |
| Glycoprotein, a1 Acid (Orosomucoid Acid) | 0.2 mg |
| Gelatin, Type B: 225 Bloom (40% Solution) | 3 ml |
| Poly-D-Lysine Hydrobromide; (M.W. 70,000–150,000) | 0.5 mg |
| Protamine, Free Base | 8 mg |
| DEAE - Dextran | 45 mg |
| Protein Component: | |
| Elastin | 50 mg |
| Collagen, Type III: Acid Soluble (0.75 mg dissolved in 0.5 ml acetic acid) | 0.5 ml |
| Collagen, Water Soluble | 200 mg |
| Hydrolastin (Hydrolyzed Elastin) - 10% Solution (Mainly containing β-Elastin-low SD. Elastin) | 2 ml |

Example B

Delivery System (Substitute Cell Membrane Variation Formulated for Full Vitamin and Coenzyme Biocomplex) Version 2

| Ingredient | Amount 1/kg Cream |
|---|---|
| Aqueous Media Consisting Of: | |
| Distilled Water (Frozen Thawed) | 18 ml |
| EDTA-Na$_2$ | 0.01 g |
| Molybdic Acid Sodium Salt | 0.042 g |
| Dithiothreitol | 0.0008 g |
| D-Trehalose | 0.053 g |
| Sucrose | 0.156 g |
| D-Sorbitol | 0.5 g |
| Aprotinin; Activity: ~6300 KIU/me | 700 KIU / 0.11 ml |
| Glutation | 0.025 g |
| L-Ascorbic Acid; 20–200 Mesh | 0.04 g |
| Prionex; (10% Solids in Solution) | 0.013 ml |
| Albumin, Bovine (BSA) | 0.013 g |
| Ammonium Sulfate | 0.13 g |
| Potassium Chloride | 0.025 g |

Delivery System (Substitute Cell Membrane Variation Formulated for Full Vitamin and Coenzyme Biocomplex) Version 2

| Ingredient | Amount 1/kg Cream |
|---|---|
| Polyethylenglycol 200 | 1 ml |
| Germaben IIE | 0.025 ml |
| Lipid Component: | |
| Nonadecanoic Acid Methyl Ester | 7 mg |
| Arachidic Acid | 10 mg |
| Heneicosanoic Acid Methyl Ester | 4 mg |
| Behenic Acid | 2 mg |
| Tristearin | 2 mg |
| Triarachidin | 1 mg |
| Egg Phosphatidylcholine-99% | 40 mg |
| Soy PC (Soy Phosphatidylcholine-90%) | 40 mg |
| H-SPC (Hydrogenated Soy PC) | 50 mg |
| PC Type X-E; from egg yolk - 60% | 200 mg |
| PE (L-a Phosphatidylethanolamine-Type IIS) Containing: Phospholipids- and glypolipids | 25 mg |
| DMPC (Dimuristoyl Phosphatidyl-choline-C: 14) | 5 mg |
| DMPC (Dimuristoyl Phosphatidyl-glycerol-C: 16) | 2 mg |
| DPPC (Dipalmitoyl Phosphatidyl-choline-C: 16) | 6 mg |
| DPPG (Dipalmitoyl Phosphatidyl-glycerol-C: 16) | 2 mg |
| DSPS (Distearoyl Phosphatidyl-choline-C: 18) | 6 mg |
| DSPG (Distearoyl Phosphatidyl-glycerol-C: 18) | 1 mg |
| DPPE (Dipalmytoyl Phosphatidyl-ethanolamine-C: 16) | 3.5 mg |
| Maleic Acid Hydroxide | 40 mg |
| Cerebrosides (Ceramide Galactosides) | 1 mg |
| Cholesterol | 15 mg |
| Ergosterol (Provitamin D2) | 10 mg |
| Carbohydrate Component: | |
| Heparin Sodium Salt | 5 mg |
| Chondriotin Sulfate A | 60 mg |
| Chondriotin Sulfate B (Dermatan Sulfate) | 0.25 mg |
| Chondroitin Sulfate C | 8 mg |
| Hyaluronic Acid | 1.4 mg |
| Gelatin, Type B: 225 Bloom (4% Solution) | 3 ml |
| Poly-D-Lysine Hydrobromide; (M.W. 70,000–150,000) | 0.5 mg |
| Protamine, Free Base | 10 mg |
| DEAE-Dextran | 50 mg |
| Protein Component: | |
| Elastin | 60 mg |
| Collagen, Type III: Acid Soluble (0.75 mg dissolved in 0.2 ml acetic acid) | 0.5 ml |
| Collagen, Water Soluble | 50 mg |

Example C

Delivery System (Substitute Cell Membrane) Version #3

| Ingredient | Amount/1 kg Cream |
|---|---|
| Aqueous Media Consisting Of: | |
| Distilled Water | 10.0 ml |
| EDTA- Na$_2$ | 0.01 g |
| Molybdic Acid Sodium Salt | 0.079 g |

-continued

Delivery System (Substitute Cell Membrane) Version #3

| Ingredient | Amount/1 kg Cream |
|---|---|
| Dithiothreitol | 0.0026 g |
| D-Trehalose | 0.145 g |
| Sucrose | 0.657 g |
| D-Sorbitol | 2.62 g |
| Cholic Acid Sodium Salt (Sodium Cholate) | 0.0084 g |
| Glycocholic Acid Sodium Salt | 0.0016 g |
| Taurocholic Acid Sodium Salt | 0.35 g |
| Glutation | 0.066 g |
| L-Ascorbic Acid; 20–200 mesh | 0.118 g |
| Aprotinin; Activity: 10,000 KIU/ml Solution | 1300 KIU 0.18 ml |
| Prionex; (10% Solids in Solution) | 0.039 ml |
| Albumin, Bovine (BSA) | 0.039 g |
| Ammonium Sulfate | 0.384 g |
| Potassium Chloride | 0.079 g |
| Polyethylene glycol 200 | 4 ml |
| Germaben IIE | 0.035 ml |
| Lipid Component: | |
| Nonadecanoic Acid Methyl Ester | 6 mg |
| Arachidic Acid | 6 mg |
| Heneicosanoic Acid Methyl Ester | 3 mg |
| Behenic Acid | 1 mg |
| Tristearin | 1 mg |
| Triarachidin | 2 mg |
| R-SPC (Hydrogenated Soy Phosphatidylcholine-93% | 750 mg |
| Soy PC - 93% (Soy phosphatidylcholine) | 750 mg |
| PE: (L-a Phosphatidylethanolamine-Type IIS) Containing: Phospholipids- and glypolipids | 15 mg |
| PS Brain Extract, Type III: (L-a Phosphatidylserine) | 1 mg |
| PI Phosphatidylinositol; Crude, from Soybean Containing: PE and Phosph. Acid | 2 mg |
| DMPC (Dimuristoyl Phosphatidilcho-line-C: 14) | 10 mg |
| DMPG (Dimuristoyl Phosphatidyl-glycerol-C: 14) | 4 mg |
| DPPC (Dimalmitoyl Phosphatidyl-choline-C: 16) | 15 mg |
| DPPG (Dipalmitoyl Phosphatidyl-glycerol-C: 16) | 6.5 mg |
| DSPC (Distearoyl Phosphatidyl-choline-C: 18) | 12 mg |
| DSPG (Distearoyl Phosphatidyl-glycerol-C: 18) | 5 mg |
| DMPE (Dimuristoyl Phosphatidyl-ethanolamine-C: 14) | 2.5 mg |
| DSPE (Distearoyl Phosphatidyl-ethanolamine-C: 18) | 4 mg |
| DPPE (Dipalmytoyl Phosphatidyl-ethanolamine-C: 16) | 3 mg |
| Maleic Acid Hydrazide | 50 mg |
| Brain Extract, Type VIII; (from Bovine Brain - 30% Sphingolipids; 30% Cerebroside; 10% Sulfated) | 8 mg |
| Cerebrosides | 0.8 mg |
| Cholesterol | 15 mg |
| Ergosterol (Provitamin D2) | 10 mg |
| Carbohydrates: | |
| Heparin Sodium Salt | 10 mg = 1400 Units |
| Chondroitin Sulfate A | 60 mg |
| Chondroitin Sulfate B (Dermatan Sulfate) | 0.3 mg |
| Chondroitin Sulfate C | 8 mg |
| Hyaluronic Acid | 20 mg |
| Glycoprotein, a1 Acid (Orosomucoid Acid) | 0.1 mg |
| Gelatin, Type B: 225 Bloom (2% Solution) | 10 ml |
| Poly-D-Lysine Hydrobromide; | 0.4 mg |

-continued

Delivery System (Substitute Cell Membrane) Version #3

| Ingredient | Amount/1 kg Cream |
|---|---|
| (70,000–150,000) | |
| Protamine, Free Base | 8 mg |
| DEAE - Dextran | 50 mg |
| Protein Component: | |
| Elastin | 35 mg |
| Hydrolastin (Hydrolyzed Elastin) - 10% Solution (Mainly containing β-Elastin-low M.W. Elastin) | 3 ml |
| Collagen, Water Soluble | 250 mg |
| Collagen, Type III: Acid Soluble 0.15% Solution | 0.5 ml |
| Procedure: | |

1. Adjust pH of the SCM up to ~4.0.

Example D

Delivery System (Substitute Cell Membrane Formulated Without Proteins For Self-Tanning Biocomplexes) Version 4

| Ingredient | Amount/1 kg Cream |
|---|---|
| Aqueous Media Consisting Of: | |
| Distilled Water (Frozen Thawed) | 18 ml |
| EDTA-Na$_2$ | 0.01 g |
| Molybdic Acid Sodium Salt | 0.064 g |
| Dithiothreitol | 0.0013 g |
| D-Trehalose | 0.081 g |
| Sucrose | 0.24 g |
| D-Sorbitol | 0.6 g |
| Aprotinin; Activity: 10,000 KIU/ml Solution | 700 KIU 0.07 ml |
| Glutation | 0.026 g |
| L-Ascorbic Acid; 20–200 mesh | 0.05 g |
| Prionex; (10% Solids in Solution) | 0.019 ml |
| Albumin, Bovine (BSA) | 0.019 g |
| Ammonium Sulfate | 0.16 g |
| Potassium Chloride | 0.03 g |
| Polyethylene glycol 200 | 1 ml |
| Germaben IIE | 0.028 ml |
| Bronopol | 0.014 g |
| Procedure: | |

1. Adjust pH of the SCM up to about 4.0.

Liquid Component:

| Ingredient | Amount/1 kg Cream |
|---|---|
| Stearic Acid (Octadecenoic Acid) Free Base | 35 mg |
| Nonadecanoic Acid Methyl Ester | 7 mg |
| Arachidic Acid | 20 mg |
| Heneicosanoic Acid Methyl Ester | 4 mg |
| Behenic Acid | 25 mg |
| Tristearin | 4 mg |
| Triarachidin | 4 mg |
| Tribehenin | 0.5 mg |
| Egg PC (Egg Phosphatidylcholine) 98% | 80 mg |
| Soy PC (Soy Phosphatidylcholine) 98% | 80 mg |
| h-SPC (Hydrogenated Soy Phosphatidylcholine - or Hydrogenated Egg Phosphatidylcholine 99% | 100 mg |

-continued

Delivery System (Substitute Cell Membrane Formulated Without Proteins For Self-Tanning Biocomplexes) Version 4

| Ingredient | Amount/1 kg Cream |
| --- | --- |
| PC (L-a Phosphatidylcholine, Type X-E; from Egg Yolk 60%) | 320 mg |
| PE (L-a Phosphatidylethanolamine-Type IIS) Containing: Phospholipids- and glypolipids | 15 mg |
| PS Brain Extract, Type III: (L-a Phosphatidylserine) | 1.5 mg |
| PI Phosphatidylinositol; Crude, from Soybean Containing: PE and Phosph. Acid | 4 mg |
| DMPC (Dimuristoyl Phosphatidilcholine-C: 14) | 6 mg |
| DMPG (Dimuristoyl Phosphatidyl-glycerol-C: 14) | 3.5 mg |
| DPPC (Dimalmitoyl Phosphatidyl-choline-C: 16) | 8 mg |
| DPPG (Dipalmitoyl Phosphatidyl-glycerol-C: 16) | 4 mg |
| DSPC (Distearoyl Phosphatidyl-choline-C: 18) | 6 mg |
| DSPG (Distearoyl Phosphatidyl-glycerol-C: 18) | 3 mg |
| DMPE (Dimuristoyl Phosphatidyl-ethanolamine-C: 14) | 2 mg |
| DSPE (Distearoyl Phosphatidyl-ethanolamine-C: 18) | 2 mg |
| DPPE (Dipalmytoyl Phosphatidyl-ethanolamine-C: 16) | 2 mg |
| Maleic Acid Hydrazide | 75 mg |
| Brain Extract, Type VIII; (from Bovine Brain - 30% Sphingolipids; 30% Cerebroside; 10% Sulfated) | 15 mg |
| Cerebrosides (Ceramide Galactoside Bovine) | 0.8 mg |
| Cholesterol | 30 mg |
| Ergosterol (Provitamin p2) | 20 mg |
| Carbohydrate Component: | |
| Heparin Sodium Salt | 10 mg = 1400 Units |
| Chondriotin Sulfate A | 75 mg |
| Chondriotin Sulfate B (Dermatan Sulfate) | 0.25 mg |
| Chondriotin Sulfate C | 10 mg |
| Hyaluronic Acid | 1.25 mg |
| Glycoprotein, a1 Acid (Orosomucoid Acid) | 0.2 mg |
| Gelatin, Type B: 225 Bloom (4% Solution) | 3.75 ml = 150 mg |
| Poly-D-Lysine Hydrobromide; (70,000–150,000) | 0.4 mg |
| Protamine, Free Base | 8 mg |
| DEAE - Dextran | 60 mg |

EXAMPLES OF MULTI-COMPONENT BIOLOGICALLY ACTIVE COMPLEXES MBAC

Example 1

Multicomponent Biologically Active Complex Created for Normal Skin Version 1

Consists of:

Protein-peptide biocomplex for normal skin
Steroid-catecholamine biocomplex for normal skin -continued

Multicomponent Biologically Active Complex Created for Normal Skin Version 1

Intracellular Transmitters biocomplex for all types of skin
Prostaglandin biocomplex for all types of skin

Protein - Peptide Biocomplex for Normal Skin

| Ingredient | Amount 1/kg |
| --- | --- |
| Cream Aqueous Media Consisting Of: | |
| Phosphate Buffer Ph 7.6 | 5.0 ml |
| Hydroxypropyl-β-Cyclodextrin | 0.5 g |
| Adrenocorticotropic Hormone (ACTH) (Fragment 1–24) | 50 ng |
| β-Lipotropin (β-Endorphin); (Fragment 61–91) | 4 μg |
| Somatotropin (HGH) (from human pituitary) | 10 miu = 5 μg |
| Follicle-Stimulating Hormone (FSH) (from human pituitary) | 0.5 iu = 0.07/μg |
| Luteinizing Hormone (LH) (from human pituitary) | 0.5 iu = 0.1 μg |
| Thyrotropic Hormone (TSH) (from human pituitary) | 0.5 miu = 0.071/μg |
| Vasopressin (Arginine Vasopressin) | 20 ng = 0.7 μl |
| Parathyroid Hormone (Fragment 1–36) | 0.65 μg |
| Thyrocalcitonin (Calcitonin) (from Salmon) | 20 ng |
| Angiotensin II Human | 5 ng |
| Glucagon (Mixture of Bovine & Porcine) | 40 μg |
| Vasoactive Intestinal Peptide (VIP) | 40 ng |
| Gastric Inhibitory Polypeptide (GIP) (Human) | 100 ng |
| Insulin (Human) | 16 miu = 0.6666 μg |
| Delivery system of Example A | 26.14 g |

Steroid - Catecholamine Biocomplex for Normal Skin

| | |
| --- | --- |
| Aqueous Media Consisting Of: | |
| Phosphate Buffer pH 7.6 | 5.0 ml |
| Hydroxypropyl -β-Cyclodextrin | 0.4 g |
| Bioactive Agents: | |
| Hydrocortisone (Cortisol) (water-soluble; balanced with HPBC) | 75 μg |
| Corticosterone - 21-sulfate; Potassium Salt | 1.8 μg |
| Progesterone (water-soluble; balanced with HPBC) | 6 μg |
| β-Estradiol (water-soluble; balanced with HPBC) | 100 ng |
| Estriol-3-Sulfate Sodium salt | 70 ng |
| Cholecalciferol Sulfate (Vitamin D3 sulfate) | 500 μg |
| Epinephrine hydrochloride (Adrenalin) | 200 ng |
| Arterenol hydrochloride (Noradrenalin) | 200 ng |
| d-Aldosterone-21-Hemisuccinate | 125 ng |
| Delivery system of Example A | 26.14 g |

Intracellular Transmitters Biocomplex - Universal For All Types of Skin

| | |
| --- | --- |
| Aqueous Media Consisting Of: | |
| Phosphate Buffer pH 7.6 | 5.0 ml |
| Hydroxypropyl-β-Cyclodextrin | 1.0 g |

-continued

Multicomponent Biologically Active Complex Created for Normal Skin
Version 1

Bioactive Agents:

| | |
|---|---|
| Adenosine-5-triphosphate Calcium Salt (ATP) (Water-Soluble) | 6.25 mg |
| Guanosine-5-triphosphate Lithium Salt (GTP) | 1.25 mg |
| Phosphoinositedes Sodium Salt; Purified from Bovine Brain Containing: a) 15–20% phosphotidyl inositol 4,5-diphosphate and phosphatidyl-inositol 4-monophosphate; b) the remainder is a mixture of phosphatidylinositol and phosphotidyl-serin | 62.5 μg |
| Brain Extract (Type I) Containing: a) 10–20% Phosphatidyl-inosilides and 50–60% phosphatidyl-serines as well as several other brain lipids | 2.25 mg |
| Adenosine 3'5'-cyclic Monophosphate Sodium Salt (3'5'-AMP) (Soluble to extent of about 100 mg per ml water. pH of aqueous solution is approximately 7.0) | 1.5 mg |
| Guanosine 3'5'-Cyclic Monophosphate Sodium Salt (3'5'-GMP) | 0.5 mg |
| d-myo-Inositol Triphosphate Potassium Salt (IP3) (from Bovine brain containing two isomers: ~80–90% 1,4,5-isomer with primary 2,4,5 isomer and <0, 05 mol. a. per mole inositol 1,4,5-triph. stimulate intracellular calcium mobilization | 1.25 μg |
| Phosphodiesterase 3'5'-cyclic Nucleotide Activator (Calmodulin) Activity >40,000 Units per mg. protein | 150 Units = 3.75 μg |
| Delivery System of Example A | 26.14 g |

Prostaglanain Biocomplex - Universal For All Types of Skin

Aqueous Media Conaisting Of:

| | |
|---|---|
| Phosphate Buffer pH 7.6 | 5.0 ml |
| Hydroxypropyl-β-Cyclodextrin | 0.4 g |

Bioactive Agents:

| | |
|---|---|
| Prostaglandin D$_2$ | 2 μg |
| Prostaglandin E$_1$ | 2 μg |
| Prostaglandin E$_2$ | 2 μg |
| Prostaglandin F$_{2\alpha}$ | 1.5 μg |
| Prostaglandin I$_2$Sodium Salt (Prostacyclin) | 2.0 μg |
| Delivery system of Example A | 26.14 g |

Example 2

Multi-component Biologically Active Complex especially created for Dry Skin -
Version 1

Consists of:

Protein-Peptide Biocomplex for Dry Skin
Steroid-Catecholamine Biocomplex for Dry Skin
Intracellular Transmitters Biocomplex - Universal
Prostaglandin Biocomplex - Universal -continued

Multi-component Biologically Active Complex especially created for Dry Skin -
Version 1

Protein - Peptide Biocomplex for Dry Skin

| Ingredient | Amount 1/kg Cream |
|---|---|

Aqueous Media Consisting Of:

| | |
|---|---|
| Phosphate Buffer pH 7.6 | 5.0 ml |
| Hydroxypropyl-β-Cyclodextrin | 0.5 g |

Bioactive Agent:

| | |
|---|---|
| Adrenocorticotropic Hormone (ACTH) (Fragment 1–24) | 110 μg |
| β-Lipotropin (β-Endorphin); (Fragment 61–91) | 6 μg |
| Somatotropin (HGH) | 10 miu = 5 mg |
| Follicle-Stimulating Hormone (FSH) | 0.5 iu = 0.071/μg |
| Luteinizing Hormone (LH) (from human pituitary) | 0.5 iu = 0.1 μg |
| Thyrotropic Hormone (TSH) | 0.75 miu = 0.1071/μg |
| Vasopressin | 15 mg = 0.525 μl |
| Parathyroid Hormone (Fragment 1–34) | 1.0 μg |
| Vasoactive Intestinal Peptide (VIP) | 60 ng |
| Insulin | 24 miu = 1.0 μg |
| Delivery system of Example A | 26.14 g |

Steroid Catecholaimne Biocomplex for Dry Skin

Aqueous Media Consisting of:

| | |
|---|---|
| Phosphate Buffer pH 7.6 | 5.0 ml |
| Hydroxypropyl-β-Cyclodextrin | 0.4 g |

Bioactive Agents:

| | |
|---|---|
| Hydrocortisone (water-soluble; balanced with HPBC) | 75 μg |
| Corticosterone-21-Sulfate | 1.8 μg |
| Progesterone (water-soluble; balanced with HPBC) | 7.2 μg |
| β-Estradiol (water-soluble; balanced with HPBC) | 50 ng |
| Estriol-3-Sulfate Sodium Salt | 40 ng |
| Cholecalciferol Sulfate (Vitamin D3 Sulfate) | 1000 μg |
| Epinephrine hydrochloride (Adrenalin) | 50 ng |
| Arterenol hydrochloride (Noradrenalin) | 50 ng |
| d-Aldosterone-21-Hemisuccinate | 200 ng |
| Delivery system of Example A | 26.14 g |

Intracellular Transmitters Biocomplex - Universal For All Types of Skin

Aqueous Media Consisting Of:

| | |
|---|---|
| Phosphate Buffer pH 7.6 | 5.0 ml |
| Hydroxypropyl-β-Cyclodextrin | 1.0 g |

Bioactive Agents:

| | |
|---|---|
| Adenosine-5-triphosphate Calcium Salt (ATP) (Water-Soluble) | 6.25 mg |
| Guanosine-5-triphosphate Lithium Salt (GTP) | 1.25 mg |
| Phosphoinositedes Sodium Salt; Purified from Bovine Brain Containing: a) 15–20% phosphotidyl inositol 4,5-diphosphate and phosphat-idylinositol 4-monophosphate; b) the remainder is a mixture of phosphatidylinositol and phosphotidyl-serin | 62.5 μg |

Multi-component Biologically Active Complex especially created for Dry Skin - Version 1

| | |
|---|---|
| Brain Extract (Type I) Containing: a) 10–20% Phosphatidyl-inosilides and 50–60% phosphatidyl-serines as well as several other brain lipids | 2.25 mg |
| Adenosine 3'5'-cyclic Monophosphate Sodium Salt (3'5'-AMP) (Soluble to extent of about 100 mg per ml water. pH of aqueous solution is approximately 7.0) | 1.5 mg |
| Guanosine 3'5'-Cyclic Monophosphate Sodium Salt (3'5'-GMP) | 0.5 mg |
| d-myo-Inositol Triphosphate Potassium Salt (IP3) (from Bovine brain containing two isomers: ~80–90% 1,4,5-isomer with primary 2,4,5 isomer and <0, 05 mol. a. per mole inositol 1,4,5-triph. stimulate intracellular calcium mobilization | 1.25 μg |
| Phosphodiesterase 3'5'-cyclic Nucleotide Activator (Calmodulin) Activity >40,000 Units per mg. protein | 150 Units = 3.75 μg |
| Delivery System of Example A | 26.14 g |

Prostaglandin Biocomplex - Universal For All Types of Skin

Aqueous media Consisting of:

| | |
|---|---|
| Phosphate Buffer pH 7.6 | 5.0 ml |
| Hydroxypropyl-β-Cyclodextrin | 0.4 g |

Bioactive Agents:

| | |
|---|---|
| Prostaglandin D$_2$ | 2 μg |
| Prostaglandin E$_1$ | 2 μg |
| Prostaglandin E$_2$ | 2 μg |
| Prostaglandin F$_{2α}$ | 1.5 μg |
| Prostaglandin I$_2$ Sodium Salt (Prostacyclin) | 2.0 μg |
| Delivery system of Example A | 26.14 g |

Example 3

Multicomponent Biologically active Complexes created for Very Dry Skin Version 1

Consists of:

Protein-peptide biocomplex for very dry skin
Steroid-catecholamine biocomplex for very dry skin
Intracellular Transmitters Biocomplex - universal
Prostaglandins biocomplex - universal

Protein - Peptide Biocomplex for Very Dry Skin

| Ingredient | Amount 1/kg Cream |
|---|---|

Aqueous Consisting of:

| | |
|---|---|
| Phosphate Buffer pH 7.6 | 5.0 ml |
| Hydroxypropyl-β-Cyclodextrin | 0.5 g |

Bioactive Agents:

| | |
|---|---|
| Adrenocorticotropic Hormone (ACTH) (Fragment 1–24) | 155 ng |
| β-Lipotropin (β-Endorphin); (Fragment 61–91) | 8 mg |
| Somatotropin (HGH) | 10 miu = 5 mg |
| Follicle-Stimulating Hormone (FSH) | 0.5 iu = 0.071/mg |
| Luteinizing Hormone (LH) | 0.51 iu = 0.1 mg |
| Thyrotropic Hormone (TSH) | 1.0 miu = 0.1428/mg |
| Vasopressin | 15 ng = 0.525 ml |
| Parathyroid Hormone (Fragment 1–34) | 1.5 μg |
| Vasoactive Intestinal Peptide (VIP) | 80 ng |
| Insulin | 30 miu = 1.25 mg |
| Delivery system of Example A | 26.16 g |

Steroid - Catecholamine Biocomplex for Very Dry Skin

Aqueous Media Consisting Of:

| | |
|---|---|
| Phosphate Buffer pH 7.6 | 5.0 ml |
| Hydroxypropyl-β-Cyclodextrin | 0.4 g |

Bioactive Agents:

| | |
|---|---|
| Hydrocortisone (water-soluble; balanced with HPBC) | 75 μg |
| Corticosterone-21-Sulfate | 1.8 μg |
| Progesterone (water-soluble; balanced with HPBC) | 7.2 μg |
| β-Estradiol (water-soluble; balanced with HPBC) | 30 ng |
| Estriol-3-Sulfate Sodium Salt | 20 μg |
| Cholecalciferol Sulfate (Vitamin D3 Sulfate) | 1500 μg |
| Epinephrine hydrochloride (Adrenalin) | 25 ng |
| Arterenol hydrochloride (Noradrenalin) | 25 ng |
| τ-Aldosterone-21-Hemisuccinate | 250 ng |
| Delivery system of Example A | 26.16 g |

Intracellular Transmitters Biocomplex - Universal For All Types of Skin

Aqueous Media Consisting Of:

| | |
|---|---|
| Phosphate Buffer pH 7.6 | 5.0 ml |
| Hydroxypropyl-β-Cyclodextrin | 1.0 g |

Bioactive Agents:

| | |
|---|---|
| Adenosine-5-triphosphate Calcium Salt (ATP) (Water-Soluble) | 6.25 mg |
| Guanosine-5-triphosphate Lithium Salt (GTP) | 1.25 mg |
| Phosphoinositedes Sodium Salt; Purified from Bovine Brain Containing: a) 15–20% phosphotidyl inositol 4,5-diphosphate and phosphat-idylinositol 4-monophosphate; b) the remainder is a mixture of phosphatidylinositol and phosphotidyl-serin | 62.5 μg |
| Brain Extract (Type I) Containing: a) 10–20% Phosphatidyl-inosilides and 50–60% phosphatidyl-serines as well as several other brain lipids | 2.25 mg |
| Adenosine 3'5'-cyclic Monophosphate Sodium Salt (3'5'-AMP) (Soluble to extent of about 100 mg per ml water. pH of aqueous solution is approximately 7.0) | 1.5 mg |
| Guanosine 3'5'-Cyclic Monophosphate Sodium Salt (3'5'-GMP) | 0.5 mg |
| d-myo-Inositol Triphosphate Potassium Salt (IP3) | 1.25 μg |

Multicomponent Biologically active Complexes created for Very Dry Skin
Version 1

| | |
|---|---|
| (from Bovine brain containing two isomers: ~80–90% 1,4,5-isomer with primary 2,4,5 isomer and <0, 05 mol. a. per mole inositol 1,4,5-triph. stimulate intracellular calcium mobilization | |
| Phosphodiesterase 3'5'-cyclic Nucleotide Activator (Calmodulin) Activity >40,000 Units per mg. protein | 150 Units = 3.75 μg |
| Delivery System of Example A | 26.14 g |

Prostaglandin Biocomplex - Universal For All Types of Skin

Aqueous Media Consisting of:

| | |
|---|---|
| Phosphate Buffer pH 7.6 | 5.0 ml |
| Hydroxypropyl-β-Cyclodextrin | 0.4 g |
| Bioactive Agents: | |
| Prostaglandin $D_2$ | 2 μg |
| Prostaglandin $E_1$ | 2 μg |
| Prostaglandin $E_2$ | 2 μg |
| Prostaglandin $F_{2\alpha}$ | 1.5 μg |
| Prostaglandin $I_2$ Sodium Salt (Prostacyclin) | 2.0 μg |
| Delivery System of Example A | 26.14 g |

Example 4

Multicomponent Biologically Active Complexes for Oily Skin - Version 1

Consists of:

Protein-peptide Biocomplex for oily skin
Steroid-catecholamine biocomplex for oily skin
Intracellular Transmitters Biocomplex - universal
Prostaglandin Biocomplex - universal

Protein - Peptide Biocomplex for Oily Skin

| Ingredient | Amount 1/kg Cream |
|---|---|
| Aqueous Media Consisting Of: | |
| Phosphate Buffer pH 7.6 | 5.0 ml |
| Hydroxypropyl-β-Cyclodextrin | 0.5 g |
| Bioactive Agents: | |
| Somatotropin (HGH) | 10 miu = 5 μg |
| Follicle-Stimulating Hormone (FSH) | 0.41 iu = 0.057/μg |
| Luteinizing Hormone (LH) | 0.4 iu = 0.08 μg |
| Vasopressin | 25 ng = 0.875 μl |
| Thyrocalcitonin (Calcitonin) (from Salmon) | 130 ng |
| Angiotensin | 12 ng |
| Glucagon | 150 μg |
| Vasoactive Intestinal Peptide (VIP) | 20 ng |
| Gastric Inhibitor Peptide | 375 ng |
| Lipase, Type I (from Wheat Germ) | 50 mg |
| Lipase, Type XI | 10,000 Units |
| Heparin Sodium Salt | 4,000 Units = |

| | |
|---|---|
| (Grade II) | 28.6 mg |
| Delivery system of Example A | 26.14 g |

Steroid - Catecholamine Biocomplex for Oily Skin

Aqueous Media Consisting Of:

| | |
|---|---|
| Phosphate Buffer pH 7.6 | 5.0 ml |
| Hydroxypropyl-β-Cyclodextrin | 0.4 g |
| Bioactive Agents: | |
| Hydrocortisone (water-soluble; balanced with HPBC) | 75 μg |
| Corticosterone-21-Sulfate | 1.8 μg |
| Progesterone (water-soluble; balanced with HPBC) | 3 μg |
| β-Estradiol (water-soluble; balanced with HPBC) | 200 ng |
| Estriol-3-Sulfate Sodium salt | 150 ng |
| Epinephrine hydrochloride (Adrenalin) | 600 ng |
| Arterenol hydrochloride (Noradrenalin) | 825 ng |
| d-Aldosterone-21-hemisuccinate | 60 ng |
| Delivery system of Example A | 26.14 g |

Intracellular Transmitters Biocomplex - Universal For All Types of Skin

Aqueous Media Consisting Of:

| | |
|---|---|
| Phosphate Buffer pH 7.6 | 5.0 ml |
| Hydroxypropyl-β-Cyclodextrin | 1.0 g |
| Bioactive Agents: | |
| Adenosine-5-triphosphate Calcium Salt (ATP) (Water-Soluble) | 6.25 mg |
| Guanosine-5-triphosphate Lithium Salt (GTP) | 1.25 mg |
| Phosphoinositedes Sodium Salt; Purified from Bovine Brain Containing: a) 15–20% phosphotidyl inositol 4,5-diphosphate and phosphatidylinositol 4-monophosphate; b) the remainder is a mixture of phosphatidylinositol and phosphotidylserin | 62.5 μg |
| Brain Extract (Type I) Containing: a) 10–20% Phosphatidyl-inosilides and 50–60% phosphatidyl-serines as well as several other brain lipids | 2.25 mg |
| Adenosine 3'5'-cyclic Monophosphate Sodium Salt (3'5'5-AMP) (Soluble to extent of about 100 mg per ml water. pH of aqueous solution is approximately 7.0) | 1.5 mg |
| Guanosine 3'5'-Cyclic Monophosphate Sodium Salt (3'5'-GMP) | 0.5 mg |
| d-myo-Inositol Triphosphate Potassium Salt (IP3) | 1.25 μg |
| (from Bovine brain containing two isomers: ~80–90% 1,4,5-isomer with primary 2,4,5 isomer and <0, 05 mol. a. per mole inositol 1,4,5-triph. stimulate intracellular calcium mobilization | |
| Phosphodiesterase 3'5'-cyclic Nucleotide Activator (Calmodulin) Activity >40,000 Units per mg. protein | 150 Units = 3.75 μg |
| Delivery System of Example A | 26.14 g |

Prostaglandin Biocomplex - Universal For All Types of Skin

Aqueous Media Consisting Of:

| | |
|---|---|
| Phosphate Buffer pH 7.6 | 5.0 ml |
| Hydroxypropyl-β-Cyclodextrin | 0.4 g |
| Bioactive Agents: | |
| Prostaglandin $D_2$ | 2 μg |
| Prostaglandin $E_1$ | 2 μg |

Example 5

Multicomponent Biologically Active Complexes for Very Oily Skin - Version 1

Consists of:

Protein-peptide biocomplex for very oily skin
Steroid-catecholamine biocomplex for very oily skin
Intracellular transmitters biocomplex - universal
Prostaglandin biocomplex - universal

Protein - Peptide Biocomplex for Very Oily Skin

| Ingredient | Amount 1/kg Cream |
|---|---|
| Aqueous Media Consisting Of: | |
| Phosphate Buffer pH 7.4 | 5.0 ml |
| Hydroxypropyl-β-Cyclodextrin | 0.5 g |
| Bioactive Agents: | |
| Somatotropin (HGH) | 10 miu = 5 µg |
| Follicle-Stimulating Hormone (FSH) | 0.4 iu = 0.057/µg |
| Luteinizing Hormone (LH) | 0.4 iu = 0.08 µg |
| Vasopressin | 25 ng = 0.875 µl |
| Thyrocalcitonin (Calcitonin) (from Salmon) | 160 ng |
| Angiotensin | 16 ng |
| Glucagon | 180 µg |
| Vasoactive Intestinal Peptide (VIP) | 20 ng |
| Gastric Inhibitor Peptide | 425 ng |
| Lipase, Type I | 80 mg |
| Lipase, Type XI | 15,000 Units |
| Heparin Sodium Salt (Grade II) | 6,000 Units = 42.3 mg |
| Delivery system of Example A | 26.14 g |

Steroid - Catecholamine Biocomplex for Very Oily Skin

| | |
|---|---|
| Aqueous Media Consisting Of: | |
| Phosphate buffer pH 7.6 | 5.0 ml |
| Hydroxypropyl-β-Cyclodextrin | 0.4 g |
| Bioactive Agents: | |
| Hydrocortisone (water-soluble; balanced with HPBC) | 75 µg |
| Corticosterone-21-Sulfate | 1.8 µg |
| Progesterone (water-soluble; balanced with HPBC) | 2.0 µg |
| β-Estradiol (water-soluble; balanced with HPBC) | 300 ng |
| Estriol-3-sulfate Sodium salt | 200 ng |
| Epinephrine hydrochloride (Adrenalin) | 750 ng |
| Arterenol hydrochloride (Noradrenalin) | 1050 ng |
| d-Aldosterone-21-hemisuccinate | 60 ng |
| Delivery system of Example A | 26.14 g |
| Prostaglandin E$_2$ | 2 µg |
| Prostaglandin F$_{2\alpha}$ | 1.5 µg |
| Prostaglandin I$_2$ Sodium Salt (Prostacyclin) | 2.0 µg |
| Delivery system of Example A | 26.14 g |

Intracellular Transmitters Biocomplex - Universal For All Types of Skin

| | |
|---|---|
| Aqueous Media Consisting Of: | |
| Phosphate Buffer pH 7.6 | 5.0 ml |
| Hydroxypropyl-β-Cyclodextrin | 1.0 g |
| Bioactive Agents: | |
| Adenosine-5-triphosphate Calcium Salt (ATP) (Water-Soluble) | 6.25 mg |
| Guanosine-5-triphosphate Lithium Salt (GTP) | 1.25 mg |
| Phosphoinositedes Sodium Salt; Purified from Bovine Brain Containing: a) 15–20% phosphotidyl inositol 4,5-diphosphate and phosphatidylinositol 4-monophosphate; b) the remainder is a mixture of phosphatidylinositol and phosphotidylserin | 62.5 µg |
| Brain Extract (Type I) Containing: a) 10–20% Phosphatidyl-inosilides and 50–60% phosphatidyl-serines as well as several other brain lipids | 2.25 mg |
| Adenosine 3'5'-cyclic Monophosphate Sodium Salt (3'5'-AMP) (Soluble to extent of about 100 mg per ml water. pH of aqueous solution is approximately 7.0) | 1.5 mg |
| Guanosine 3'5'-Cyclic Monophosphate Sodium Salt (3'5'-GMP) | 0.5 mg |
| d-myo-Inositol Triphosphate Potassium Salt (IP3) (from Bovine brain containing two isomers: ~80–90% 1,4,5-isomer with primary 2,4,5 isomer and <0, 05 mol. a. per mole inositol 1,4,5-triph. stimulate intracellular calcium mobilization | 1.25 µg |
| Phosphodiesterase 3'5'-cyclic Nucleotide Activator (Calmodulin) Activity >40,000 Units per mg. protein | 150 Units = 3.75 µg |
| Delivery System of Example A | 26.14 g |

Prostaglandin Biocomplex - Universal For All Types of Skin

| | |
|---|---|
| Aqueous Media Consisting Of: | |
| Phosphate Buffer pH 7.6 | 5.0 ml |
| Hydroxypropyl-β-Cyclodextrin | 0.4 g |
| Bioactive Agents: | |
| Prostaglandin D$_2$ | 2 µg |
| Prostaglandin E$_1$ | 2 µg |
| Prostaglandin E$_2$ | 2 µg |
| Prostaglandin F$_{2\alpha}$ | 1.5 µg |
| Prostaglandin I$_2$ Sodium Salt (Prostacyclin) | 2.0 µg |
| Delivery system of Example A | 26.14 g |

Example 6

MBAC for Oily Skin Version 2 (Direct Procedure)

Consisting of Four Parts:

I - Protein - Peptide Biocomplex for Oily Skin
II - Steroid - Catecholamine - Vitamin Biocomplex for Oily Skin
III - Intracellular Transmitters - Nucleotide Coenzymes-Prostaglandin Biocomplex for Oily Skin -continued IV - Delivery System (Substitute Cell Membrane) -
    Version #3 - see Example C
    Protein - Peptide Biocomplex for Oily Skin

| Ingredient | Amount 1/kg cream |
|---|---|
| Phosphate Buffer, pH 7.4 | 1.5 ml |
| HPBC | 1 g |

Protein Peptides

| Ingredient | Amount |
|---|---|
| h-GH (somatotropin) | 10 miu =0 5 µg |
| VIP (vasoactive Intestinal Polypeptide) | 0.02 µg |
| GIP (Gastric Inhibitor Polypeptide) | 0.375 µg |
| Glucagon | 150 µg |
| Thyrocalcitonin; from salmon (calcitonin) | 0.15 µg |
| Arg-Vasopressin; Aqueous Solution | 0.875 ml = 0.025 µg |
| Angiotensin II; Human | 0.012 mg |
| Lipase, Type XI | 10,000 units = 0.025 mg |
| Lipase, Type I | 50 mg |
| Heparin Sodium Salt | 4,000 units = 28.6 mg |

Procedure

1. Step-by-step add each active substances to solvent.
2. Mix thoroughly on a magnetic stirrer or on a low speed mixer not less than 4 hours.
3. Store in a refrigerator.

Steroid - Catecholamine - Vitamin Biocomplex for Oily Skin

Part A

| Ingredient | Amount |
|---|---|
| Aqueous media consisting of Phosphate Buffer, pH 7.4 | 2.25 ml |
| HPBC | 1.5 g |

Steroids

| Ingredient | Amount |
|---|---|
| Hydrocortisone - Water Soluble (Balanced in 2-HPBC) | 0.75 mg Act.: 0.075 mg |
| Corticosterone-21-Sulfate Potassium Salt | 0.0018 mg |
| d-Aldosterone-21-Hemisuccinate | 0.00006 mg |
| β-Estradiol-Water Soluble (Balanced in 2-HPBC) | 0.0044 mg Act: 0.000, 2 |
| Estriol-3-Sulfate Sodium Salt | 0.00015 mg |
| Progesterone-Water Soluble (Balanced in 2-HPBC) | 0.043 mg Act: 0.003 mg |

Part B

| Ingredient | Amount |
|---|---|
| 1N HCl | 0.2 ml |
| Epinephrine Hydrochloride (Adrenalin) | 0.0006 mg |
| Arterenol Hydrochloride (Norodrenlin) | 0.00083 mg |

Part C

| Ingredient | Amount |
|---|---|
| Ethyl Alcohol | 0.75 ml |
| α-Tocopherol Acetate (Vit E) act: 1360 Iu/g | 30 mg |
| Ergocalciferol (Vitamin $D_2$) act: $4 \times 10^6$ USp/g | 1 mg |
| Retinol Palmitate (Vit A) : dispersed in gelatin matrix | 60 mg |

Procedure

1. Separately prepare Parts A, B & C by adding active substances to the appropriate solvent.
2. Add Part B to Part A by mixing on a magnetic stirrer.
3. Add Part C to mixture of Part A & B (prepared as in Step 2) by mixing.
4. Continue mixing on a magnetic stirrer or on a low speed mixer not less than 4 hours.
5. Store in a refrigerator.

Intracellular Transmitters - Nucleotide Coenzymes - Prostaglandin Biocomplex for Oily Skin

| Ingredient | Amount |
|---|---|
| Phosphate Buffer, pH 7.4 | 3.75 ml |
| HPBC | 2.5 g |

Intracellular Transmitters

| Ingredient | Amount/1 kg cream |
|---|---|
| ATP; Adenosine 5'-Triphosphate Disodium Salt | 25 mg |
| GTP; Guanosine 5'-Triphosphate Lithium Salt | 1.5 mg |
| PI; Phosphoinositedes Sodium Salt Mixture of 15–20% $PI_4$ and PC | 0.062 mg |
| PI; Brain Extract Type I contain: ~10–20% PI & 50–60% PS | 2.25 mg |
| c-AMP; Adenosine 3'5'-Cyclic monophosph. | 5 mg |
| c-GMP; Guanosine 3'5'-Cyclic monophosph. Sodium Salt | 1.9 mg |
| $IP_3$; d-myo-Inositol 1,4,5-Triphosphate Hexasodium Salt | 0.005 mg |
| Calmoduline; phosphodiesterase 3'5-Cyclic Nucleotide Activator | 140 Units = 0.0035 |
| Calmoduline; Crude | 0.012 mg |
| Coenzyme A Sodium Salt | 0.2 mg |
| β-NAD; β-Nicotinamide Adenine Dinucleotide Sodium Salt | 10 mg |
| β-NADP; β-Nicotinamide Adenine Dinucleotide Phosphate | 2 mg |

Prostaglandins

| Ingredient | Amount |
|---|---|
| $PGD_2$; Prostaglandin $D_2$ | 0.002 mg |
| $PGE_1$; Prostaglandin $E_1$ | 0.002 mg |
| $PGE_2$; Prostaglandin $E_2$ | 0.002 mg |
| $PGF_{2\alpha}$; Prostaglandin $F_2\alpha$ | 0.0015 mg |
| $PGI_2$; Prostaglandin 12 (Prostacyclin) | 0.002 mg |

Procedure

1. Step-by-step add each active substances to solvent.
2. Mix thoroughly on a magnetic stirrer on a low speed mixer not less than 4 hours.
3. Store in a refrigerator.

Example 7

MBAC for Dry Skin - Version 2 (Direct Procedure)

Consisting of Five Parts:

1 - Proteins - Peptide Biocomplex for Dry Skin
2 - Steroid - Vitamin Biocomplex for Dry Skin
3 - Intracellular Transmitters - Nucleotide Coenzyme - Prostaglandin Biocomplex for Dry Skin
4 - Amino - Acids Biocomplex for Dry Skin
5 - Delivery System (Substitute Cell Membrane) - Version 3 - see Example C Protein - Peptide Biocomplex for Dry Skin

| Ingredient | Amount 1 kg/cream |
|---|---|
| Phosphate Buffer, pH 7.4 | 1.5 ml |
| HPBC 0.725 mmol | 1 g |
| h-GH (Somatotropin) | 8 miu = 4 µg |
| β-Endorphin (β-Lipotropin) | µmg |
| VIP (Vasoactive Intestinal Polypeptide) | 0.12 mg |
| Insulin | 35 miu = 1.4 µg |
| PTH (Parathyroid Hormone) | 0.8 µg |
| Vasopressin | 1.75 ml = 0.05 µg |

Procedure:

1. Step-by-step, add each active substance to solvent.
2. Mix thoroughly on a magnetic stirrer or on low speed mixer not less than 4 hours.
3. Store in a refrigerator.

Steroid - Vitamin Biocomplex for Dry Skin
Solvent

Part A

| | |
|---|---|
| Phosphate Buffer, pH 7.4 | 1.5 ml |
| HPBC | 0.725 mmol 1 g |

Steroids

| | |
|---|---|
| Hydrocortisone - Water Soluble | 0.75 mg |
| (Balanced in 2-HPBC) | Act: 0.075 mg |
| Corticosterone-21-Sulfate Potassium Salt | 0.0018 mg |
| d-Aldosterone-21-Hemisuccinate | 0.0005 mg |
| β-Estradiol-Water Soluble | 0.0033 mg |
| (Balanced in 2-HPBC) | Act.: 0.00015 mg |
| Estriol-3-Sulfate Sodium Salt | 0.0001 mg |
| Progesterone-Water Soluble | 0.171 mg |
| (Balanced in 2-HPBC) Act: 0.0012 mg | |

Solvent

Part B

| | |
|---|---|
| Ethyl Alcohol | 0.25 ml |

Oil Soluble Vitamins

| | |
|---|---|
| Ergocalciferol (Vitamin $D_2$) | 2 mg |
| Act: $4 \times 10^6$ USP/g | |
| Cholecalciferol Sulfate Sodium Salt | 0.6 mg |
| α-Tocopherol Acetate (Vitamin E) | 30 mg |
| Act: 1360 IU/g | |

Procedure:

1. Separately prepare Part A and Part B by adding active substances to the appropriate solvents.
2. Add Part B to Part A slowly, by mixing on a magnetic stirrer or on low speed mixer.
3. Mix thoroughly on a magnetic stirrer or on a low speed mixer not less than 4 hours.
4. Store in a refrigerator.

Intracellular Transmitters - Nucleotide Coenzyme - Prostaglandin Biocomplex for Dry Skin

| | |
|---|---|
| Phosphate Buffer, pH 7.4 | 3.75 ml |
| HPBC | 2.5 g |
| ATP: Adenosine 5'-Triphosphate Disodium Salt | 25 mg |
| GTP; Guanosine 5'-Triphosphate Lithium Salt | 1.5 mg |
| PI; Phosphainositides Sodium Salt mixture of ~15–20% × $PI_4P$, PI & P5 | 0.062 mg |
| PI; Brain Extract, Type I. containing ~10–20 × PI's 50–60% PS | 2.25 mg |
| c-AMP; Adenosine 3'5'-Cyclic Monophosphate (soluble: 5 mg per ml water) | 4.5 mg |
| c-GMP; Guanosine 3'5'-Cyclic Monophosphate Sodium Salt | 1.5 mg |
| 1,2-DG; 1,2-Diacylglycerol | 0.1 mg |
| $IP_3$; d-myo-Inositol 1,4,5-Triphosphate Hexasodium Salt | 0.005 mg |
| Calmoduline; Phosphodiesterase 3'5'-Cyclic Nucleotide Activator (from bovine brain) | 140 Units = 0.0035 mg |
| Calmoduline; Crude; from bovine brain | 0.01 mg |
| PK; Protein Kinase; from bovine heart | 0.012 mg |
| Coenzyme A Sodium Salt | 0.20 mg |
| β-NAD; β-Nicotinamide Adenine Dinucleotide Sodium Salt | 10 mg |
| β-NADP; β-Nicotinamide Adenine Dinucleotide Phosphate | 1.6 mg |
| $PGD_2$; Prostaglandin $D_2$ | 0.002 mg |
| $PGE_1$; Prostaglandin $E_1$ | 0.002 mg |
| $PGE_2$; Prostaglandin $E_2$ | 0.0025 mg |
| $PGI_2$; Prostaglandin $I_2$ (Prostacyclin) | 0.0015 mg |

Procedure:

1. Step-by-step add each active substances to Solvent while mixing.
2. Mix thoroughly on a magnetic stirrer or on a low speed mixer not less than 4 hours.
3. Store in a refrigerator.

Amino-Acids Biocomplex for Dry Skin

Part A

| | |
|---|---|
| Distilled Water | 1.5 ml |
| HPBC | 1 g |

Amino Acids

| | |
|---|---|
| L-Tryptophan | 100 mg |
| L-Phenylalanine | 100 mg |
| L-Cysteine Hydrochloride | 70 mg |

Part B

| | |
|---|---|
| 1 M HCl | 0.7 ml |
| L-Cystin | 70 mg |
| L-Tyrosine | 80 mg |

Procedure:

1. Separately prepare Part A and Part B by adding of the active substances to the appropriate solvent.
2. Add Part B to Part A slowly, by mixing on a magnetic stirrer.
3. Continue mixing on a magnetic stirrer or low speed mixer not less than 4 hours.
4. Store in a refrigerator.

Example 8

MBAC for Eye Zone

Consisting of five parts:

1 - Protein - Peptide Biocomplex for Eye Zone
2 - Steroid - Vitamin Biocomplex for Eye Zone
3 - Intracelluiar Transmitters - Nucleotide Coenzyme - Prostaglandin Biocomplex for Eye Zone
4 - Nucleic Acid Bases - Amino-Acids Biocomplexes for Eye Zone
5 - Delivery System (substitute cell membrane) - version 3 - see Example C

Protein - Peptide Biocomplex for Eye Zone

| Ingredient | Amount 1 kg/cream |
|---|---|
| Aqueous media comprising: | |
| Phosphate Buffer | 1.5 ml |
| HPBC | 0.725 mmol 1 g |
| h-GH (Somatotropin) | 14 miu = 7 μg |
| β-Endorphin (β-Lipotropin) | 6 μg |
| VIP (Vasoactive Intestinae Polypeptide) | 0.15 μg |
| Insulin | 54 miu = 2.16 μg |
| PTH (Parathyroid Hormone) | 1.3 μg |
| Vasopressin | 3 ml = 0.086 |

Steroid - Vitamin Biocomplex for Eye Zone

Part A
Aqueous media consisting of:

| | |
|---|---|
| Phosphate Buffer, pH 7.4 | 1.8 ml |
| HPBC | 1.2 g |
| Hydrocortisone - Water Soluble | 0.75 mg |
| (Balanced in 2-HPBC) | Act: 0.075 μg |
| Corticosterone - 21 - Sulfate Potassium Salt | 0.0018 mg |
| d-Aldosterone-21-Hemisuccinate | 0.0003 mg |
| β-Estradiol-Water Soluble | 0.0044 mg |
| (Balanced in 2-HPBC) | Act.: 0.0002 mg |
| Estriol-3-Sulfate Sodium Salt | 0.00015 mg |
| Progesterone-Water Soluble | 0.220 mg |

| | |
|---|---|
| (Balanced in 2-HPBC) | Act.: 0.0154 mg |
| Part B | |
| Ethyl Alcohol | 0.3 ml |
| Ergocalciferol (Vitamin $D_2$) Act: $4 \times 10^6$ USP/g | 3 mg |
| Cholecalciferol Sulfate Sodium Salt (Vitamin $D_3$) | 0.6 mg |
| α-Tocopherol Acetate (Vitamin E) (Act: 1360 IU/g) | 60 mg |

Procedure:

1. Separately prepare Part A and Part B by adding active substances to the appropriate solvents.
2. Add Part B to Part A slowly, by mixing on a magnetic stirrer or on a low speed mixer.
3. Mix thoroughly on a magnetic stirrer or on a low speed mixer not less than 4 hours.
4. Store in a refrigerator.

Intracellular Transmitters - Nucleotide Coenzyme - Prostaglandin Biocomplex for Eye Zone Intracellular Transmitters:

| | |
|---|---|
| Phosphate Buffer, pH 7.4 | 3.75 ml |
| HPBC | 2.5 g |
| ATP; Adenosine 5'-triphosphate disodium salt | 35 mg |
| GTP; Guanosine 5'-triphosphate lithium salt | 1.85 mg |
| PI; Phosphoinosites sodium salt; mixture of ~15–20% $PI_4$ PI PS | 0.078 mg |
| PI; Brain extract, Type I, containing 10–20% PI and 50–60% PS | 2.8 mg |
| C-AMP; Adenosine 3'5'-cyclic monophosphate (solubility: 5 mg per ml water) | 5 mg |
| C-GMP; Guanosine 3'5'-cyclic monophosphate sodium salt | 1.85 mg |
| 1,2-DG; 1,2-Diacylglycerol | 0.1 mg |
| $IP_3$; d-myo-Inositol 1,4,5-triphosphate hemodium salt | 0.006 mg |
| Calmoduline; phosphodiesterase 3'5'-cyclic nucleotide activator; from bovine brain | 140 Units = 0.0035 μg |
| Calmoduline; crude | 0.012 mg |
| PK; protein kinase | 0.015 mg |
| Coenzyme A, sodium salt | 0.2 mg |
| β-NAD; β-Nicotinamide adenine dinucleotide sodium salt | 12.5 mg |
| β-NADP; β-Nicotinamide adenine dinucleotide phosphate | 2 mg |

Prostaglandins:

| | |
|---|---|
| $PGD_2$; Prostaglandin $D_2$ | 0.003 mg |
| $PGE_2$; Prostaglandin $E_2$ | 0.0038 mg |
| $PGI_2$; Prostaglandin $I_2$ (prostocyclin) | 0.018 mg |
| $PGE_1$; Prostaglandin $E_1$ | 0.003 mg |

Procedure:

1. Step-by-step add active ingredient to solvent.
2. Mix thoroughly on a magnetic stirrer or on a low speed mixer not less than 4 hours.
3. Store in a refrigerator.

Nucleic Acid Bases - Amino Acids Biocomplex for Eye Zone

Part A
Aqueous media comprising:

| | |
|---|---|
| Distilled Water | 2.25 ml |
| HPBC | 1.5 g |
| Part B | |
| 1 N NaOH | 3.5 ml |

Nucleic Acid Bases:

| | |
|---|---|
| Adenine (A) | 40 mg |
| Guanine (G) | 50 mg |
| Cytosine (C) | 10 mg |
| Thyamine (T) | 40 mg |
| Uracil (U) | 80 mg |

Amino Acids:

| | |
|---|---|
| L-Tryptophan | 80 mg |
| L-Cysteine Hydrochloride | 50 mg |
| L-Phenylalanine | 70 mg |
| Part C | |
| 1 N HCl | 2.5 ml |

Amino Acids:

| | |
|---|---|
| L-Cystin | 50 mg |
| L-Tyrosine | 50 mg |

Procedure:

1. Separately prepare Part A, Part B and Part C by adding the active substance to appropriate solvent by mixing on a magnetic stirrer.
2. Slowly add Part B to Part A by mixing on a magnetic stirrer.
3. Slowly add Part C to the mixture of Parts A and B (prepared in Step 2) by mixing on a magnetic stirrer.
4. Continue mixing on a magnetic stirrer or on a low speed mixer not less than 4 hours.
5. Store in refrigerator.

Example 9

Multicomponent Biologically Active Complex Created For Acne Version 1

This MBAC is comprised of standard Biocomplexes previously described and consists of:

Protein—Peptide Biocomplex for oily skin—Version 1—as described in Example 4

Protein—Peptide Biocomplex for very oily skin—Version 1—as described in Example 5

Steroid—Catecholamine Biocomplex for oily. skin—Version 1—as described in Example 4

Steroid—Catecholamine Biocomplex for very oily skin—Version 1—as described in Example 5

Intracellular Transmitters—Nucleotide Coenzymes—Prostaglandin Biocomplex for oily skin—Version 2—as described in Example 6

Delivery System (Substitute Cell Membrane)—Version #3—as described in Example C

Example 10

Biologically Active Complexes Created For Eczema And Psoriasis

Biocomplex for Eczema and Psoriasis is composed of standard Biocomplexes previously described and consists of:

Protein—Peptide Biocomplex for normal skin—Version 1—as described in Example 1

Protein—Peptide Biocomplex for dry skin—Version 2—as described in Example 7

Steroid—Catecholamine Biocomplex for normal skin—Version 1—as described in Example 1

Steroid—Vitamin Biocomplex for dry skin—Version 2—as described in Example 7

Intracellular Transmitters—Nucleotide Coenzymes

Prostaglandin Biocomplex for dry skin—Version 2—as described in Example 7, but using a double amount Amino-Acid Biocomplex for dry skin—Version 2—as described in Example 7

Delivery System (Substitute Cell Membrane)—Version 3—as described in Example C

Full Vitamin and Coenzyme Biocomplex—as described in Example 13

Example 11

Biologically Active Complex Created For Neurodermatitis And Itches

Biocomplex for Neurodermatitis and Itches is composed of standard Biocomplexs previously described and consists of:

Protein—Peptide Biocomplex for normal skin—Version 1—described in Example 1

Steroid—Catecholamine Biocomplex for normal skin—Version 1—as described in Example 1

Steroid—Vitamin Biocomplex for dry skin—Version 2—as described in Example 7

Intracellular Transmitters—Nucleotide Coenzymes

Prostaglandin Biocomplex for dry skin—Version 2—as described in Example 7

Delivery System (Substitute Cell Membrane)—Version 3—as described in Example C

LDL Model—Low Density Lipoprotein Model—Version 1—as described in Example 10.

Example 12

Multicomponent Biologically Active Complexes Created for Shock and Critical Conditions For the treatment of shock and critical conditions, various biocomplexes with different activity and different amounts of active agents were created since shock is a very complex pathology with individual variations in each organism.

In all cases, MBAC for shock and critical conditions consists of the same active substances, with the differences being in the concentration of the active agents.

These MBACs consist of:

Protein—Peptide Biocomplex for shock condition

Steroid—Catecholamine Biocomplex for shock condition

Intracellular Transmitters—Nucleotide Coenzymes—Prostaglandin Biocomplex for shock condition Delivery System (substitute cell membrane)—Version 3—as described in Example C.

Given below are the preferred ranges for each active substance in MBACs for shock and critical conditions.

| Protein - Peptide Biocomplex for Shock Conditions | |
| --- | --- |
| Ingredient | Amount/Usage Per Dose |
| Phosphate Buffer | 1 ml |
| HPBC (Hydroxypropyl-β-Cyclodextrin) | 0.2 g |
| Adrenocorticotropic Hormone (Fragment 1-24) | 0.5–2.5 ng |
| β-Endorphin | 0.04–0.1 ng |
| (Fragment 61-91) | |
| Somatotropin (B-GH) | 0.05–0.1 ng |
| Thyrotropic Hormone (TSH) | 0.005–0.01 miu |
| Vasopressin (Arginine Vasopressin) | 0.2–2 ng |
| Thyrocalcitonin | 0.2–1 ng |
| Angiotensin II | 0.1–3 ng |
| Insulin | 0.15-1 miu |

Procedure:

1. Step-by-step, add each active substance to solvent.

2. Mix thoroughly on a magnetic stirrer or on low speed mixer not less than 4 hours.

3. Store in a refrigerator.

| Steroid - Catecholamine Biocomplex for Shock Condition | |
| --- | --- |
| Ingredient | Amount/Usage Per Dose |
| Phosphate Buffer, pH 7.4 | 1 ml |
| HPBC | 0.2 g |
| Hydrocortisone - Water Soluble (Balanced in 2-HPBC) | 0.7–1.2 μg |
| Corticosterone-21-Sulfate Potassium Salt | 20–30 ng |
| Cortisol | 15–25 ng |
| d-Aldosterone-21-Hemisuccinate | 1–5 ng |
| Cholecalciferol Sulfate Sodium Salt | 2.5–4 ng |
| Dopamine | 4–8 ng |
| Epinephrine Hydrochloride (Adrenalin) | 5–10 ng |
| Arterenol Hydrochloride (Noradrenalin) | 5–10 ng |

Procedure:

1. Step-by-step, add each active substance to solvent.

2. Mix thoroughly on a magnetic stirrer or on low speed mixer not less than 4 hours.

3. Store in a refrigerator.

Intracellular Transmitters—Nucleotide Coenzymes Prostaglandins Biocomplex for Shock Condition

| Ingredient | Amount/Usage Per Dose |
| --- | --- |
| Phosphate Buffer, pH 7.4 | 1 ml |
| HPBC | 0.25 g |
| ATP; Adenosine 5'-Triphosphate | 0.25–1.2 mg |
| GTP; Guanosine 5'-Triphosphate | O.02–0.1 mg |
| Phosphainositides Sodium Salt | 0.01–0.06 mg |
| Phosphatidylinozitol-4,5-Diphosphate | 0.01–005 mg |
| 3'5'-AMP; Cyclic Adenosinmonophosphate | 0.08–2 mg |
| 3'5'-GMP; Guanosine 3'5'-Cyclic Monophosphate | 0.03–0.7 mg |
| 1,2-Diacylglycerol | 0.05–0.08 mg |
| d-myo-Inositol 1,4,5-Triphosphate | 0.001–0.002 mg |
| Calmoduline; Phosphodiesterase 3'5'-Cyclic Nucleotide Activator | 14–50 Units |
| Calmoduline; Crude | 0.001–0.01 mg |
| Protein Kinase | 0.0012–0.006 mg |
| Coenzyme A | 0.02–0.06 mg |
| β-Nicotinamide Adenine Dinucleotide Phosphate | 0.2–0.8 mg |

-continued

| Ingredient | Amount/Usage Per Dose |
|---|---|
| β-Nicotinamide Adenine Dinucleotide | 2–8 mg |
| Heparin Sulfate | 20–150 Units |
| Prostaglandin $F_{2\alpha}$ | 0.2–1 ng |
| Prostaglandin $D_2$ | 0.2–0.8 ng |
| Prostaglandin $I_2$ | 0.4–2 ng |
| Prostaglandin $F_{1\alpha}$ | 0.3–0.7 ng |

Procedure:

1. Step-by-step, add active substances to solvent.
2. Mix thoroughly on a magnetic stirrer or on low, speed.
3. Store in a refrigerator.

Example 13

Example of Bioactive Complexes Modeling (BCM)—Version 1

The following is a formulation of self-tanning biocomplex, which consists of three parts:

dihydroacetone (DHA)

juglone vitamins

This biocomplex can be used with or without substitute cell membrane (SCM) delivery system—see Example D of delivery system.

| DHA Part of Self-tanning Biocomplex | |
|---|---|
| Ingredient | Amount/1 kg Cream |
| Aqueous media comprising: | |
| Distilled Water | 85 ml |
| Phosphate-citrate buffer, pH 5 | 18 ml |
| EDTA No. 1 | 0.1 g |
| HPBC | 52 g |
| DHA | 30 g |
| D-Trehalose | 1 g |
| Sucrose | 5.8 g |
| Germaben 2E | 0.8 g |

Procedure:

1. Mix all compounds.
2. Mix on a magnetic stirrer or low speed mixer not less than 5–6 hours.

| Juglone Part of Self-Tanning Biocomplex | |
|---|---|
| Ethyl alcohol | 17 ml |
| Juglone | 10.1 g |
| Vitamins Part of Self-Tanning Biocomplex | |
| Part I | |
| Distilled Water | 11 ml |
| HPBC | 2 g |
| D-Trehalose | 0.06 g |
| Sucrose | 0.19 g |
| Germaben 2E | 0.2 ml |
| Tween 20 | 2 ml |
| Tween 80 | 2 ml |
| Part II - melting everything together thoroughly on a magnetic stirrer or on a homogenizer | |
| Retinol palmitate (1,600,000 USP/g) | 1 g |
| α-Tocopherol acetate (1360 IU/g) | 0.3 g |
| Ergocalciferol (4–$10^6$ IU/g) | 0.0014 g |
| β-carotene (1,600,000 of Vit. A per gram) | 0.04 g |
| Antioxidant mixture | 1.6 ml |
| Span 20 | 0.4 ml |
| Span 80 | 0.2 ml |

Procedure:

1. Prepare each part separately. Part II must be melted thoroughly on a magnetic stirrer or on a homogenizer.
2. Slowly add Part I to Part II by mixing on a homogenizer with a G45 knife, until emulsion forms. Then, slowly increase the rate of addition of Part I to Part II.
3. Mix on a homogenizer not less than 40 minutes.
4. For full encapsulation, continue mixing on a magnetic stirrer or low speed mixer not less than 3 hours.

EXAMPLES OF NATURAL BIOACTIVE COMPLEXES

Further examples of natural bioactive complexes (NBAs):

LDL—low density lipoproteins for topical applications

HDL—high density lipoproteins for topical applications

VLDL—very low density lipoproteins for topical application

These formulations are used without a delivery system.

Example 14

| LDL Model - Low Density Lipoprotein Model Version 1 | |
|---|---|
| Ingredient | Amount/1 kg Cream |
| Aqueous Media Consisting Of: | |
| Distilled Water | 28.0 ml |
| Hydroxypropyl-β-Cyclodextrin | 5.5 g |
| EDTA-$Na_2$ | 0.04 g |
| Sodium Bisulfite | 0.06 g |
| Tween 20 | 0.5 ml |
| PEG 200 | 0.5 ml |
| Trehalose | 0.16 g |
| Sucrose | 0.32 g |
| Antioxidant Mixture | 0.15 ml |
| Germaben 2E | 0.05 ml |
| Bronopol | 0.02 g |
| Liquid Component: | |
| Unsaturated Fatty Acids: | |
| Linoleic Acid | 1131 ml = 1017.9 mg |
| Linolelaidic Acid | 11 ml = 9.79 mg |
| Linolenic Acid | 30 ml = 27.6 mg |
| Cis-11,14,17 Eicosatrienoic Acid Ethyl Ester | 5 µl = 5 mg |
| Arachidonic Acid Sodium Salt | 15 mg |
| Cis-7,10,13,16-Docosatetraenoic Acid Methyl Ester | 1 µl = 1 mg |
| Cis-4,7,10,13,16,19-Docosahexaenoic Acid Methyl Ester | 5 µl = 5 mg |
| Saturated Fatty Acids: | |
| Stearic Acid | 12 mg |
| Nonadecanoic Acid Methyl Ester | 30 mg |

LDL Model - Low Density Lipoprotein Model
Version 1

| Ingredient | Amount/1 kg Cream |
|---|---|
| Arachidic Acid | 60 mg |
| Heneicosanoic Acid Methyl Ester | 2 mg |
| Cholesterol: | |
| Cholesterol | 130 mg |
| Triacylglycerides With Unsaturated Fatty Acids: | |
| Triolein | 250 µl = 227.5 mg |
| Trilinolein | 20 µl = 20 mg |
| Trilinolenin | 4 ml = 4 g |
| Tri-11-Eicosenoin | 5 µl = 5 mg |
| Trierucin | 5 mg |
| Triacylglycercides With Saturated Fatty Acids: | |
| Trinonodecanoin | 10 mg |
| Triarachidin | 10 mg |
| Tribehenin | 9 mg |
| Phospholipids: | |
| L-α-Phosphatidylcholine (Type X-E; ~60%) | 321 mg |
| L-α-Phosphatidylcholine (Type XV-E; ~60%) | 321 mg |
| L-α-Phosphatidylcholine (Type XII-E; ~60%) | 321 mg |
| Proteins: | |
| Albumin | 172 mg |
| Collagen (Water-Soluble) | 150 mg |
| Collagen Type 1 (Insouble from Bovine) | 100 mg |
| Collagen Type 2 (Insoluble from Bovine) | 150 mg |
| Elastin | 150 mg |

Example 15

VLDL Model - Very Low Density Lipoprotein Model
Version 1

| Ingredient | Amount/1 kg Cream |
|---|---|
| Aqueous Media Consisting Of: | |
| Distilled Water | 29.0 ml |
| Hydroxypropyl-β-Cyclodextrin | 5.5 g |
| EDTA - Na$_2$ | 0.04 g |
| Sodium Bisulfite | 0.06 g |
| Tween 20 | 0.5 ml |
| PEG 200 | 0.5 ml |
| Trehalose | 0.13 g |
| Sucrose | 0.26 g |
| Antioxidant Mixture | 0.15 ml |
| Germaben 2E | 0.05 ml |
| Bronopol | 0.02 g |
| Unsaturated Fatty Acids: | |
| Linoleic Acid | 242 µl = 217.8 mg |
| Linolelaidic Acid | 11 µl = 9.79 mg |
| Linolenic Acid | 30 µl = 27.6 mg |

VLDL Model - Very Low Density Lipoprotein Model
Version 1

| Ingredient | Amount/1 kg Cream |
|---|---|
| Cis-11,14,17 Eicosatrienoic Acid Ethyl Ester | 5 µl = 5 mg |
| Arachidonic Acid Sodium Salt | 15 mg |
| Cis-4,7,10,13,16,19-Docosahexaenoic Acid Methyl Ester | 5 µl = 5 mg |
| Saturated Fatty Acids: | |
| Stearic Acid | 11 mg |
| Nonadecanoic Acid Methyl Ester | 11 mg |
| Arachidic Acid | 11 mg |
| Heneicosanoic Acid Methyl Ester | 2 mg |
| Cholesterol: | |
| Cholesterol | 35 mg |
| Triacylglycerides With Unsaturated Fatty Acids: | |
| Triolein | 1154 µl = 1095.5 mg |
| Trilinolein | 20 µl = 20 mg |
| Trilinolenin | 4 µl = 4 mg |
| Tri-11-Eicosenoin | 5 µl = 5 mg |
| Trierucin | 5 µl = 5 mg |
| Triacylglycerides With Saturated Fatty Acids: | |
| Tristearin | 84 mg |
| Trinonodecanoin | 10 mg |
| Triarachidin | 15 mg |
| Tribehenin | 10 mg |
| Prospholipids: | |
| L-β-Phosphatidylcholine (Type X-E; ~60%) | 195 mg |
| L-α-Phosphatidylcholine (Type XV-E; ~60%) | 195 mg |
| L-α-Phosphatidylcholine (Type XII-E; ~60%) | 195 mg |
| Proteins: | |
| Albumin | 70 mg |
| Collagen (Water-Soluble) | 70 mg |
| Collagen Type 1 (Insoluble from Bovine) | 70 mg |
| Collagen Type 2 (Insoluble from Bovine) | 70 mg |
| Elastin | 70 mg |

Example 16

HDL Model- High Density Lipoprotein Model
Version 1

| Ingredient | Amount/1 kg Cream |
|---|---|
| Aqueous Media Consisting of: | |
| Distilled Water | 30 ml |
| Hydroxypropyl-β-Cyclodextrin | 5.5 g |
| EDTA - Na$_2$ | 0.04 g |
| Sodium Bisulfite | 0.06 g |
| Tween 20 | 0.5 ml |
| PEG 200 | 0.5 ml |
| Trehalose | 0.170 g |
| Sucrose | 0.340 g |

-continued

| HDL Model- High Density Lipoprotein Model Version 1 | |
|---|---|
| Ingredient | Amount/1 kg Cream |
| Antioxidant Mixture | 0.15 ml |
| Germaben | 0.05 ml |
| Bronopol | 0.02 g |
| Unsaturated Fatty Acids: | |
| Linoleic Acid | 423 µl = 380.7 mg |
| Linolelaidic Acid | 11 µl = 9.79 mg |
| Linolenic Acid | 30 µl = 27.6 mg |
| Cis-6,9,12,15-Octadecatetraenoic Acid | 0.5 mg |
| Cis-11,14,17 Eicosatrienoic Acid Ethyl Ester | 5 µl = 5 mg |
| Arachidonic Acid Sodium Salt | 15 mg |
| Cis-5,8,11,14,17-Eicosapentaenoic Acid | 0.2 mg |
| Cis-13,16,19-Docosatrienoic Acid | 0.8 mg |
| Cis-7,10,13,16-Docosatetranoic Acid | 0.8 mg |
| Cis-4,7,10,13,16,19-Docosahexaenoic Acid Methyl Ester | 10 µl = 10 mg |
| Cholesterol: | |
| Cholesterol | 50 mg |
| Triacylglycerides With Unsaturated Fatty Acids: | |
| Triolein | 60 µl = 54.6 mg |
| Trilinolein | 20 µl = 20 mg |
| Trilinolenin | 4 µl = 4 mg |
| Tri-11-Eicosenoin | 5 µl = 5 mg |
| Trierucin | 5 mg |
| Prospholipids: | |
| L-α-Phosphatidylcholine (Type X-E; ~60%) | 490 mg |
| L-α-Phosphatidylcholine (Type XV-E; ~60%) | 490 mg |
| L-α-Phosphatidylcholine (Type XII-E; 60%) | 490 mg |
| Proteins: | |
| Albumin | 535 mg |
| Collagen (Water-Soluble) | 535 mg |
| Collagen Type 1 (Insoluble from Bovine) | 100 mg |
| Collagen Type 2 (Insoluble from Bovine) | 150 mg |
| Elastin | 150 mg |

Example 17

EXAMPLE OF VITAMIN AND COENZYME BIOCOMPLEXES (VCB) Version 1

| Full Vitamin and Coenzyme Biocomplex | |
|---|---|
| Ingredient | Amount 1/kg Cream |
| Aqueous Media Consisting Of: | |
| Distilled Water | 22 ml |
| HPBC | 10 g |
| EDTA - Na$_2$ | 0.018 g |

-continued

| Full Vitamin and Coenzyme Biocomplex | |
|---|---|
| Ingredient | Amount 1/kg Cream |
| Glutation | 0.1 g |
| Trehalose | 0.5 g |
| Sucrose | 2.0 g |
| PEG 200 | 1.0 ml |
| Germaben 2E | 0.26 ml |
| Bronopol | 0.13 g |
| Bioactive Agents Part I: | |
| Thiamine Hydrochloride (Vitamin B$_1$) | 0.15 g |
| Cocarboxylase | 0.05 g |
| Flavin Mononucleotide Sodium Salt | 0.05 g |
| Nicotinamide (Niacinamide) | 1 g |
| Nicotinamide Adenine Dinucleotide Sodium Salt | 0.015 g |
| Nicotinamide Adenine Dinucleotide Phosphate Sodium Salt | 0.002 g |
| Pantothenic Acid Hemicalcium Salt | 0.8 g |
| Coenzyme A (COA) | 0.0005 g |
| Pyridoxine Hydrochloride (Vitamin B$_6$) | 0.15 g |
| Pyridoxal-5-Phosphate (Codecarboxylase) | 0.04 g |
| Ascorbic Acid (Vitamin C) | 5 g |
| Bioactive Agents Part II: (pH adjusted to 4.5–5.0) | |
| 2 M Sodium Hydroxide | 3.8 ml |
| Rutin Hydrate (Vitamin P) | 0.7 g |
| Quercetin (Vitamin P) | 0.15 g |
| Folic Acid (Pteroylglutamic Acid) | 0.03 g |
| Tetrahydrofolic Acid | 0.001 g |
| Biotin | 0.015 g |
| Bioactive Agents Part III: (pH adjusted to 4.5–5.0): | |
| Distilled Water | 15 ml |
| Tween 20 | 3 ml |
| Tween 80 | 3 ml |
| Retinol Palmitate (On Gelatin Matrix with Antiox) | 1.2 g |
| Ergocalciferol (Vitamin D$_2$) | 0.001 g |
| Cholecalciferol Sulfate (Vitamin D$_3$) | 0.00025 g |
| Tocopherol Acetate (Vitamin e) (Does not air oxidize) | 1.5 g |
| Antioxidant Mixture (Prepared on Ethyl Alcohol) | 2.0 ml |
| Span 20 | 0.6 ml |
| Span 80 | 0.3 ml |

Procedure: Prepare all three parts separately.
Part I:
  1. Add all active ingredients of Part I to Aqueous Media by mixing on a magnetic stirrer or on a homogenizer.
  2. Adjust pH of the Part I up to 4.5–5.0.
Part II:
  1. Add all active ingredients of Part II to 2M NaOH by mixing on a magnetic stirrer.
Part III:
  1. Mix together the distilled water, Tween 20 and Tween 80.
  2. Mixing all remaining components of this part on a magnetic stirrer or on a homogenizer until they mix uniformly.
  3. Slowly add the distilled water/Tween mixture to the Step 2 mixture by mixing on a homogenizer until emulsion forms. Then, increase the speed of adding distilled water/Tween mixture to the Step 2 mixture.
  4. Mix on a homogenizer not less than 30 minutes.
Final Biocomplex Preparation Procedure
  1. Slowly add Part II to Part I by mixing on a magnetic stirrer or on a homogenizer. Mix thoroughly.

2. Slowly add the mixture of Part I and II to Part III (i.e., phase) by mixing on a homogenizer.

3. Adjust final pH up to ~4.5–5.0.

4. Mix on a homogenizer with G45 knife not less than 45 minutes.

5. For full encapsulation, continue mixing on a magnetic stirrer or low speed mixer not less than 3–4 hours.

What is claimed is:

1. A method for treating the skin of a patient with abnormal skin cell metabolism to correct the abnormal skin cell metabolism and promote the resumption of normal skin cell metabolism comprising applying to the portions of the skin of such patient which have abnormal skin cell metabolism a composition containing a bioactive agent and a biologically acceptable carrier therefor, the amount of the bioactive agent being sufficient to correct the abnormal skin cell metabolism but less than the buffering amount of said agent, wherein the composition comprises:

adenosine-5-triphosphate;

guanosine-5-triphosphate;

phosphoinositedes containing:
1) 15–20% phosphatidylinositol 4,5-diphosphate and phosphatidylinositol 4-monophosphate;
2) the remainder is a mixture of phosphatidylinositol and phosphatidylserine;

Type I brain exract containing 10–20% phosphatidylinosides, 50–60% phosphatidylserines;

adenosine 3'5'-cyclic monophosphate sodium salt;

guanosine 3'5'-cyclic monophosphate;

d-myo-Inositol triphosphate; and calmodulin.

2. The method of claim 1 wherein the composition comprises by weight per 1 kg of formulated product:

1–50 mg adenosine-5-tiphosphate;

1–30 mg guanosine-5-triphosphate;

10–100 $\mu$g phosphoinositedes containg:
1) 15–20% phosphotidyl inositol 4,5-diphosphate and phosphatidylinositol 4-monophosphate;
2) the remainder is a mixture of phosphatidylinositol and phosphotidylserine;

0.5–10 mg Type 1 brain extract containing 10–20% phosphatidyhinosilides, 50–60% phosphatidylserines;

1–10 mg adenosine 3'5'-cyclic monophosphate sodium salt;

0.1–5 mg guanosine 3'5'-cyclic monophosphate;

1–66 $\mu$g d-myo-Inositol triphosphate; and

1–20 $\mu$g calmodulin.

3. The method of claim 1 wherein the composition also comprises at least one component selected from the group consisting of adrenocorticotropic hormone; β-lipotropin; β-endotphin; somatotropin; follicle-stimulatirng hormone; luteinizing hormone; thyrotropic hormone; vasopressin; patathyroid hormone; thyrocalcitonin; angiotensin II; glucagon; vasoactive intestinal peptide; gastric inhibitory polypeptide; and insulin.

4. The method of claim 3 wherein the components listed in claim 3, when present in the composition, comprise by weight per 1 kg of formulated product:

2–120 ng adrenocorticotropic hormone;

1–10 $\mu$β-lipotropin β-endorphin;

1–10 $\mu$g somatotropin;

0.01–1.0 $\mu$g follicle-stimulating hormone;

0.05–0.5 $\mu$g luteinizing hormone;

0.05–0.15 $\mu$g thyrotropic hormone;

0.02–1.0 $\mu$g vasopressin;

0.5–2.0 parathyroid hormone;

20–120 ng vasoactive intestinal peptide; and 0.5–5 $\mu$g insulin.

5. The method of claim 1 wherein the composition also comprises at least one component selected from the group consisting of hydrocortisone; corticosterone-21-sulfate; progesterone; β-estradiol; estriol-3-sulfate sodium salt; cholecalciferol sulfate; epinephrine hydrochloride; arterenol hydrochloride; and aldosterone.

6. The method of claim 5 wherein the components listed in claim 5, when present in the composition, comprise by weight per 1 kg of formulated product:

25–250 $\mu$g hydrocortisone;

1–30 $\mu$g corticosterone-21-sulfate;

2–10 $\mu$g progesterone;

50–500 ng β-estradiol;

200–700 ng estriol-3-sulfate sodium salt;

200–700 ng epinephrine hydrochloride;

300–900 ng arterenol hydrochloride; and

10–600 ng α-aldosterone-21-hemisuccinate.

7. The method of claim 1 wherein the composition also comprises at least one component selected from the group consisting of prostaglandin $D_2$, prostaglandin $E_1$, prostaglandin $E_2$, prostaglandin $F_{2\alpha}$ and prostaglndin $I_2$.

8. The method according to claim 7 wherein the components listed in claim 7, when present in the composition, comprise by weight per 1 kg of formulated product:

1–5 $\mu$g prostaglandin $D_2$,

1–5 $\mu$g prostaglandin $E_1$,

1–5 $\mu$g prostaglandin $E_2$, 0.5–3 $\mu$g prostaglandin $F_{2\alpha}$, and

1–5 $\mu$g prostaglandin $I_2$.

9. A method for treating the skin of a patient with abnomial skin cell metabolism to correct the abnormal skin cell metabolism and promote the resumption of normal skin cell metabolism comprising applying to the portions of the skin of such patient which have abnormal skin cell metabolism a composition containing a bioactive agent and a biologically acceptable carrier therefor, the amount of the bioactive agent being sufficient to correct the abnormal skin cell metabolism but less than the buffering amount of said agent, wherein the composition comprises:

adenosine-5-triphosphate;

guanosine-5-triphosphate;

phosphoinositedes containing:
1) 15–20% phosphotidyl inositol 4,5-diphosphate and phosphatidylinositol 4-monophosphate;
2) the remainder is a mixture of phosphotidylinositol and phosphotidylserine;

Type I brain extract containing 10–20% phosphotidylinosilides, 50–60% phosphatidylserines, and other brain lipids;

adenosine 3'5'-cyclic monophosphate sodium salt;

guanosine 3'5'-cyclic monophosphate;

d-myo-Inositol triphosphate;

protein kinase;

coenzyme A;

β-nicotinamide adenine dinucleotide;

β-nicotinamide adenine dinucleotide phosphate; and calmodulin;

wherein the composition further comprises a protein-peptide biocomplexbioactive agent selected from the group comprising somatotropin; follicle-stimulating hormone; luteinizig hormone; vasopressin; thyrocalcitonin; angiotensin; glucagon; vasoactive intestinal peptide; gastric inhibitory polypeptide; and mixtures thereof;

wherein the composition further comprises a second bioactive agent selected from the group comprising hydrocortisone; corticosterone-21-sulfate; progesterone; β-estradiol; estriol-3-sulfate sodium salt; epinephrine hydrochloride; arterenol hydrochloride; aldosterone and mixtures thereof; and wherein the composition further comprises a third bioactive agent selected from the group comprising prostaglandin $D_2$, prostaglandin $E_1$, prostaglandin $E_2$, prostaglandin $F_{2\alpha}$ prostaglandin $I_2$, and mixtures thereof.

* * * * *